(12) United States Patent
Seo et al.

(10) Patent No.: US 9,419,239 B2
(45) Date of Patent: Aug. 16, 2016

(54) COMPOSITE MATERIAL, LIGHT-EMITTING ELEMENT, LIGHT-EMITTING DEVICE, ELECTRONIC DEVICE, LIGHTING DEVICE, AND ORGANIC COMPOUND

(75) Inventors: Hiromi Seo, Kanagawa (JP); Harue Osaka, Kanagawa (JP); Satoshi Seo, Kanagawa (JP); Masato Suzuki, Kanagawa (JP); Nobuharu Ohsawa, Tochigi (JP)

(73) Assignee: SEMICONDUCTOR ENERGY LABORATORY CO., LTD., Kanagawa-ken (JP)

(*) Notice: Subject to any disclaimer, the term of this patent is extended or adjusted under 35 U.S.C. 154(b) by 648 days.

(21) Appl. No.: 13/539,983

(22) Filed: Jul. 2, 2012

(65) Prior Publication Data

US 2013/0009138 A1    Jan. 10, 2013

(30) Foreign Application Priority Data

Jul. 8, 2011    (JP) ................... 2011-151536

(51) Int. Cl.
| | |
|---|---|
| H01L 51/54 | (2006.01) |
| C09K 11/06 | (2006.01) |
| H01L 51/50 | (2006.01) |
| C07F 15/00 | (2006.01) |
| C07F 7/08 | (2006.01) |
| H01L 51/00 | (2006.01) |

(52) U.S. Cl.
CPC .......... *H01L 51/5088* (2013.01); *C07F 7/0809* (2013.01); *C07F 15/0033* (2013.01); *H01L 51/0052* (2013.01); *H01L 51/0072* (2013.01); *H01L 51/0094* (2013.01); *H01L 51/0085* (2013.01)

(58) Field of Classification Search
None
See application file for complete search history.

(56) References Cited

U.S. PATENT DOCUMENTS

| | | | |
|---|---|---|---|
| 5,989,737 A | 11/1999 | Xie et al. | |
| 6,013,384 A | 1/2000 | Kido et al. | |
| 6,310,231 B1 | 10/2001 | Igarashi et al. | |
| 6,361,886 B2 * | 3/2002 | Shi et al. ............... | 428/690 |
| 6,423,429 B2 | 7/2002 | Kido et al. | |
| 6,486,601 B1 | 11/2002 | Sakai et al. | |
| 6,589,673 B1 | 7/2003 | Kido et al. | |
| 6,905,787 B2 | 6/2005 | Ise | |
| 6,936,961 B2 | 8/2005 | Liao et al. | |
| 7,158,161 B2 | 1/2007 | Gyoutoku et al. | |
| 7,646,010 B2 | 1/2010 | Kawakami et al. | |
| 7,732,808 B2 | 6/2010 | Ikeda et al. | |
| 7,893,427 B2 | 2/2011 | Kumaki et al. | |
| 7,902,742 B2 | 3/2011 | Suzuki et al. | |
| 8,026,531 B2 | 9/2011 | Seo et al. | |
| 8,314,548 B2 | 11/2012 | Suzuki et al. | |
| 8,558,451 B2 | 10/2013 | Kido et al. | |
| 8,586,197 B2 * | 11/2013 | Yamazaki et al. ............ | 428/690 |
| 8,587,193 B2 | 11/2013 | Suzuki et al. | |
| 8,680,562 B2 | 3/2014 | Seo et al. | |
| 8,786,183 B2 | 7/2014 | Suzuki et al. | |
| 8,889,268 B2 | 11/2014 | Takada et al. | |
| 8,890,204 B2 | 11/2014 | Seo et al. | |
| 8,890,402 B2 | 11/2014 | Mori et al. | |
| 9,000,419 B2 | 4/2015 | Iizumi et al. | |
| 9,041,282 B2 | 5/2015 | Suzuki et al. | |
| 2002/0180349 A1 | 12/2002 | Aziz et al. | |
| 2003/0189401 A1 | 10/2003 | Kido et al. | |
| 2004/0227460 A1 | 11/2004 | Liao et al. | |
| 2005/0067951 A1 | 3/2005 | Richter et al. | |
| 2005/0084712 A1 | 4/2005 | Kido et al. | |
| 2005/0084713 A1 | 4/2005 | Kido et al. | |
| 2005/0098207 A1 | 5/2005 | Matsumoto et al. | |
| 2005/0106419 A1 | 5/2005 | Endoh et al. | |
| 2005/0170208 A1 | 8/2005 | Yatsunami et al. | |
| 2005/0218396 A1 | 10/2005 | Tsuchiya et al. | |
| 2006/0008740 A1 | 1/2006 | Kido et al. | |
| 2006/0141285 A1 * | 6/2006 | Ogasawara ................... | 428/690 |
| 2006/0292394 A1 * | 12/2006 | Iwaki et al. .................. | 428/690 |
| 2007/0007516 A1 | 1/2007 | Seo et al. | |
| 2007/0182317 A1 | 8/2007 | Kido et al. | |

(Continued)

FOREIGN PATENT DOCUMENTS

| | | |
|---|---|---|
| CN | 101800241 A | 8/2010 |
| EP | 1 351 558 A | 10/2003 |

(Continued)

OTHER PUBLICATIONS

Lee et al. "Low-voltage, high-efficiency blue phosphorescent organic light-emitting devices" Applied Physics Letters 2008, 92, 173305. Date of online publication: May 2, 2008.*

(Continued)

*Primary Examiner* — Andrew K Bohaty

(74) *Attorney, Agent, or Firm* — Robinson Intellectual Property Law Office; Eric J. Robinson

(57) ABSTRACT

A composite material including an organic compound and an inorganic compound, which has a high carrier-transport property; a composite material having an excellent property of carrier injection to an organic compound; a composite material in which light absorption due to charge transfer interaction is unlikely to occur; and a composite material having a high visible-light-transmitting property are provided. A composite material which includes an organic compound and an inorganic compound exhibiting an electron-accepting property with respect to the organic compound, in which the rings of the organic compound are all benzene rings and the number of the benzene rings of the organic compound is greater than or equal to 4 and less than or equal to 25, is provided.

24 Claims, 31 Drawing Sheets

(56) References Cited

U.S. PATENT DOCUMENTS

| | | |
|---|---|---|
| 2007/0200125 A1 | 8/2007 | Ikeda et al. |
| 2008/0136325 A1* | 6/2008 | Yamazaki et al. ............ 313/506 |
| 2008/0303003 A1* | 12/2008 | Heil et al. ................ 252/301.16 |
| 2008/0303019 A1 | 12/2008 | Nakagawa et al. |
| 2009/0026922 A1 | 1/2009 | Iwaki et al. |
| 2009/0131670 A1 | 5/2009 | Cheng et al. |
| 2009/0189519 A1 | 7/2009 | Lee et al. |
| 2009/0230847 A1 | 9/2009 | Iwaki et al. |
| 2010/0096627 A1 | 4/2010 | Ikeda et al. |
| 2010/0207518 A1 | 8/2010 | Ikeda et al. |
| 2011/0031476 A1 | 2/2011 | Oda et al. |
| 2011/0031877 A1 | 2/2011 | Takada et al. |

FOREIGN PATENT DOCUMENTS

| | | |
|---|---|---|
| EP | 1 478 025 A | 11/2004 |
| EP | 1 524 706 A | 4/2005 |
| EP | 1 617 493 A | 1/2006 |
| EP | 1 351 558 B | 7/2006 |
| EP | 1876659 A | 1/2008 |
| EP | 2090637 A | 8/2009 |
| EP | 2117063 A | 11/2009 |
| EP | 2214223 A | 8/2010 |
| EP | 2256841 A | 12/2010 |
| EP | 2284921 A | 2/2011 |
| EP | 2423994 A | 2/2012 |
| JP | 02-288092 A | 11/1990 |
| JP | 03-274695 A | 12/1991 |
| JP | 09-063771 A | 3/1997 |
| JP | 11-307259 A | 11/1999 |
| JP | 11-307264 A | 11/1999 |
| JP | 2000-351966 A | 12/2000 |
| JP | 2003-272860 A | 9/2003 |
| JP | 2004-103577 A | 4/2004 |
| JP | 2005-026121 A | 1/2005 |
| JP | 2005-150084 A | 6/2005 |
| JP | 2005-516059 | 6/2005 |
| JP | 2005-251587 A | 9/2005 |
| JP | 2006-089464 A | 4/2006 |
| JP | 2006-302870 A | 11/2006 |
| JP | 2007-043062 A | 2/2007 |
| JP | 2007-234514 A | 9/2007 |
| JP | 2007-234555 A | 9/2007 |
| JP | 2009-179627 A | 8/2009 |
| JP | 2010-186983 A | 8/2010 |
| JP | 2010-212489 A | 9/2010 |
| JP | 2011-034917 A | 2/2011 |
| TW | 200524477 | 7/2005 |
| TW | 201041435 | 11/2010 |
| TW | 201119495 | 6/2011 |
| WO | WO-03/064373 | 8/2003 |
| WO | WO-2006/093171 | 9/2006 |
| WO | WO-2008/102644 | 8/2008 |

OTHER PUBLICATIONS

Yang.Y et al., "Polyaniline as a Transparent Electrode for Polymer Light-Emitting Diodes: Lower Operating Voltage and Higher Effciency," Appl. Phys. Lett. (Applied Physics Letters), Mar. 7, 1994, vol. 64, No. 10, pp. 1245-1247.

Tokito.S et al., "Metal Oxides as a Hole-Injecting Layer for an Organic Electroluminescent Device," J. Phys. D: Appl. Phys. (Journal of Physics D: Applied Physics), 1996, vol. 29, No. 11, pp. 2750-2753.

Tao.S et al., "Anthracene Derivative for a Non-Doped Blue-Emitting Organic Electroluminescence Device With Both Excellent Color Purity and High Efficiency," Chem. Phys. Lett. (Chemical Physics Letters), 2004, vol. 397, pp. 1-4.

Taiwanese Office Action (Application No. 101124230) Dated Jan. 28, 2016.

\* cited by examiner

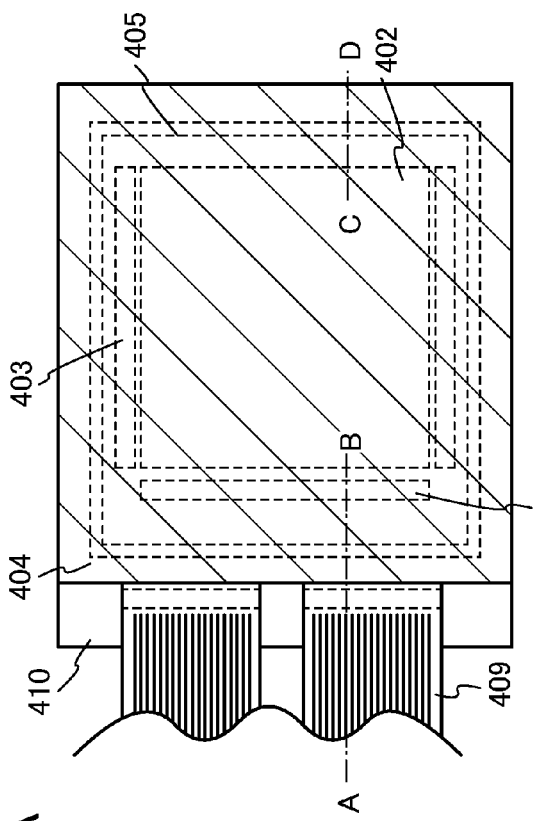
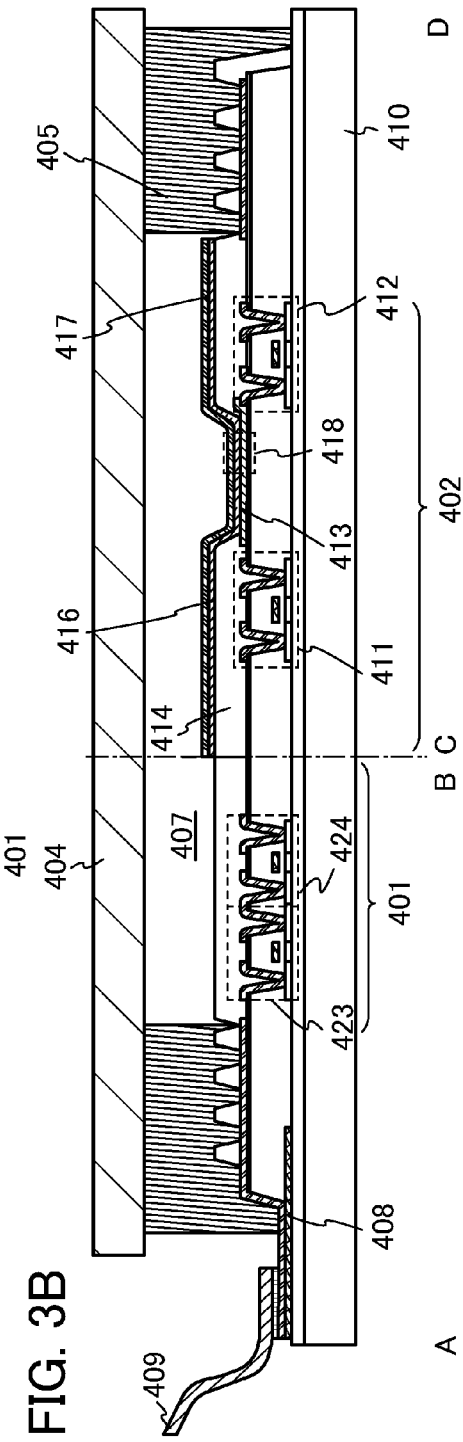
FIG. 3A
FIG. 3B

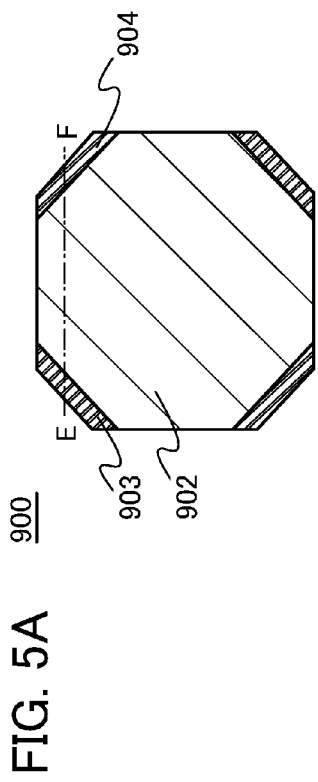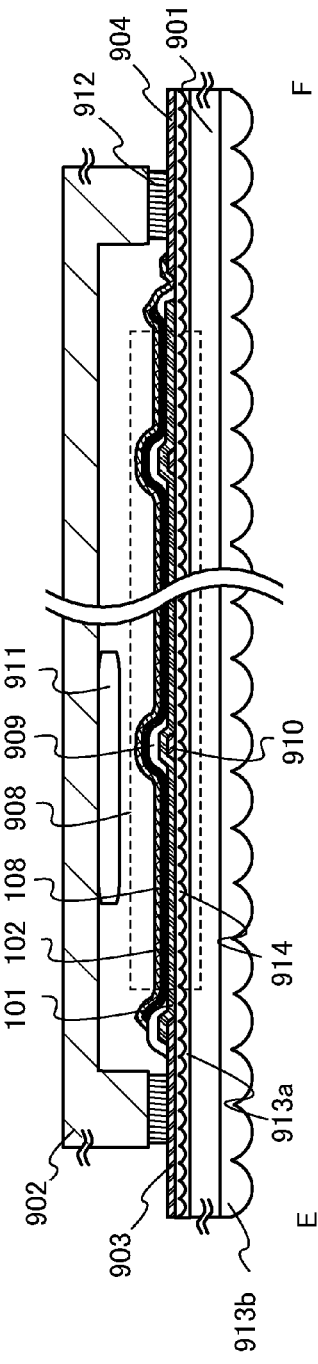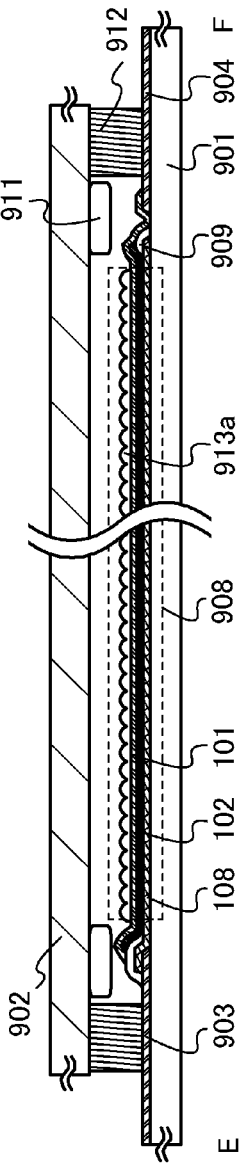

COMPOSITE MATERIAL, LIGHT-EMITTING ELEMENT, LIGHT-EMITTING DEVICE, ELECTRONIC DEVICE, LIGHTING DEVICE, AND ORGANIC COMPOUND

BACKGROUND OF THE INVENTION

1. Field of the Invention

The present invention relates to a composite material including an organic compound and an inorganic compound, a light-emitting element, a light-emitting device, an electronic device, and a lighting device. The present invention also relates to an organic compound that can be used for the composite material.

2. Description of the Related Art

In recent years, research and development have been extensively conducted on light-emitting elements using organic electroluminescence (EL). The light-emitting elements have a basic structure in which a layer containing a light-emitting organic compound is interposed between a pair of electrodes. By applying voltage to this element, light can be emitted from the light-emitting organic compound.

Since such a light-emitting element is of self-light-emitting type, it is considered that the light-emitting element has advantages over a liquid crystal display in that visibility of pixels is high, backlight is not required, and so on and is therefore suitable as a flat panel display element. In addition, it is also a great advantage that the light-emitting element can be manufactured as a thin and lightweight element. Furthermore, very high speed response is also one of the features of the light-emitting element.

Furthermore, since such light-emitting elements can be formed in a film form, they make it possible to easily form a large-area element. This feature is difficult to obtain with point light sources typified by incandescent lamps and LEDs or linear light sources typified by fluorescent lamps. Thus, light-emitting elements also have great potential as planar light sources applicable to lighting devices and the like.

As described above, application of light-emitting elements using organic EL to light-emitting devices, lighting devices, or the like is expected. At the same time, there are many issues regarding light-emitting elements using organic EL. One of the issues is a reduction in power consumption. In order to reduce power consumption, it is important to reduce driving voltage for the light-emitting element. The emission intensity of the light-emitting element using organic EL is determined by the amount of electric current flowing therein. Therefore, in order to reduce the driving voltage, it is necessary to feed a large amount of current at low voltage.

Previously, as a method of reducing driving voltage, an approach of providing a buffer layer between an electrode and the layer containing a light-emitting organic compound has been attempted. For example, it is known that driving voltage can be reduced by providing a buffer layer which includes polyaniline (PANI) doped with camphorsulfonic acid, between indium tin oxide (ITO) and a light-emitting layer (e.g., see Non-Patent Document 1). It is explained that this is because PANI has an excellent property of injecting carriers into the light-emitting layer. Note that in Non-Patent Document 1, PANI, which is used for the buffer layer, is also regarded as part of the electrode.

SUMMARY OF THE INVENTION

However, as described in the Non-Patent Document 1, PANI has a problem that transmittance becomes lower when a film thickness becomes thick. Specifically, it is reported that at a film thickness of about 250 nm, the transmittance is less than 70%. In other words, the problem lies in the transparency of the material itself that is used for the buffer layer; thus, light generated within the element cannot be extracted efficiently.

Also, according to Patent Document 1, an approach of serially connecting light-emitting elements (called light-emitting units in Patent Document 1) to improve luminance per a certain current density, that is, current efficiency, has been attempted. In Patent Document 1, for a connecting portion of serially connected light-emitting elements, a mixed layer of an organic compound and a metal oxide (specifically, vanadium oxide or rhenium oxide) is used, and this layer is considered capable of injecting holes and electrons into light-emitting units.

However, as apparent from an embodiment, for the mixed layer of an organic compound and a metal oxide that is disclosed in Patent Document 1, a high absorption peak is observed not only in the infrared region but also in the visible light region (around 500 nm), and a problem in transparency occurs. This is due to the effect of an absorption band generated by charge transfer interaction. Therefore, as expected, light generated within the element cannot be extracted efficiently, and the light emission efficiency of the element is degraded.

REFERENCE

[Patent Document 1] Japanese Published Patent Application No. 2003-272860
[Non-Patent Document] Y. Yang et. al., Applied Physics Letters, Vol. 64 (10), 1245-1247 (1994)

In view of the above, an object of one embodiment of the present invention is to provide a composite material including an organic compound and an inorganic compound and having a high carrier-transport property. Another object is to provide a composite material having an excellent property of carrier injection to an organic compound. Another object is to provide a composite material in which light absorption due to charge transfer interaction is unlikely to occur. Another object is to provide a composite material having a high visible-light-transmitting property.

Further, another object of one embodiment of the present invention is to provide a light-emitting element having high emission efficiency by application of the above composite material to the light-emitting element. Another object is to provide a light-emitting element with low driving voltage. Another object is to provide a light-emitting element with a long lifetime. Another object is to provide a light-emitting device including the light-emitting element, an electronic device including the light-emitting device, or a lighting device including the light-emitting device.

Note that an object of the invention to be disclosed below is to achieve at least one of the above-described objects.

One embodiment of the present invention is a composite material which includes an organic compound and an inorganic compound exhibiting an electron-accepting property with respect to the organic compound. The rings of the organic compound are all benzene rings. The number of the benzene rings of the organic compound is greater than or equal to 4 and less than or equal to 25. Note that the ring (benzene ring) of the organic compound included in the composite material of one embodiment of the present invention may be substituted or unsubstituted unless otherwise specified.

Another embodiment of the present invention is a composite material which includes an organic compound having a molecular weight greater than or equal to 350 and less than or equal to 2000 and an inorganic compound exhibiting an electron-accepting property with respect to the organic compound. The rings of the organic compound are all benzene rings.

Another embodiment of the present invention is a composite material which includes an organic compound and a transition metal oxide. The rings of the organic compound are all benzene rings. The number of the benzene rings of the organic compound is greater than or equal to 4 and less than or equal to 25.

Another embodiment of the present invention is a composite material which includes an organic compound having a molecular weight greater than or equal to 350 and less than or equal to 2000 and a transition metal oxide. The rings of the organic compound are all benzene rings.

The above composite material has a high carrier-transport property. The above composite material also has an excellent property of carrier injection to an organic compound. Further, in the composite material, light absorption due to charge-transfer interaction is unlikely to occur. Furthermore, the composite material has a high visible-light-transmitting property (hereinafter, simply referred to as light-transmitting property).

The absorption peak of the organic compound included in the composite material of one embodiment of the present invention appears at a shorter wavelength than the visible-light wavelengths (380 nm to 760 nm).

In the above composite material, the occurrence of light absorption due to charge-transfer interaction can be suppressed and an absorption peak of the organic compound itself can also be controlled so as to appear at a shorter wavelength than the visible-light wavelengths (380 nm to 760 nm). Thus, the composite material can have a high light-transmitting property.

The molecular weight of the organic compound is preferably greater than or equal to 350, in which case the film quality of the composite material is stable. The molecular weight is more preferably greater than or equal to 450. Although there is no particular limitation on the maximum molecular weight, the molecular weight is preferably less than or equal to 2000 in consideration of evaporativity in the case where the composite material is subjected to heating evaporation.

The organic compound may include an alkyl group having 1 to 6 carbon atoms as a substituent. The organic compound may contain silicon. For example, the organic compound may have benzene rings cross-linked with silicon. When one benzene ring is bonded to another benzene ring with silicon therebetween, a conjugated system is difficult to extend between these benzene rings, which is effective in terms of a light-transmitting property.

The organic compound may include a trialkylsilyl group as a substituent. When the organic compound includes a trialkylsilyl group which is a bulky substituent, the amorphous property of a single film of the organic compound can be increased. Thus, in one embodiment of the present invention, an organic compound which has a high molecular weight, high heat resistance, and a high amorphous property of a film as well as a high singlet excitation energy level (S1 level), a high triplet excitation energy level (T1 level), and a high light-transmitting property can be used.

It is preferable that two or more benzene rings be joined by a single bond (e.g., a biphenyl group or the like is preferably included) in terms of a carrier-transport property. Further, in terms of a thermophysical property, in the case where a large number of benzene rings are joined by a single bond in order to increase molecular weight, the benzene rings are preferably joined at the ortho position or the meta position, or cross-linked with silicon so that a conjugated system does not extend too much.

Although there is no particular limitation on the highest occupied molecular orbital level (HOMO level) of the organic compound used in the above composite material, the organic compound used in one embodiment of the present invention has a relatively deep HOMO level (specifically, lower than or equal to −5.7 eV). Accordingly, the occurrence of light absorption due to charge-transfer interaction can be suppressed. Therefore, the HOMO level of the organic compound used in the above composite material is preferably lower than or equal to −5.7 eV when measured by photoelectron spectroscopy.

It is preferable that the transition metal oxide included in the above composite material be one or a plurality of oxides selected from titanium oxide, vanadium oxide, molybdenum oxide, tungsten oxide, rhenium oxide, ruthenium oxide, chromium oxide, zirconium oxide, hafnium oxide, tantalum oxide, and silver oxide.

Another embodiment of the present invention is a light-emitting element including a layer containing a light-emitting substance (hereinafter, also referred to as EL layer) between a pair of electrodes. The layer containing a light-emitting substance includes a layer containing the above composite material.

In the above light-emitting element, it is preferable that the layer containing the composite material be in contact with one of the pair of electrodes which serves as an anode. It is also preferable that the layer containing the composite material be in contact with one of the pair of electrodes which serves as a cathode.

The above light-emitting element may include two layers containing the composite material, and it is preferable that one of the two layers containing the composite material be in contact with one of the pair of electrodes which serves as an anode and the other of the two layers be in contact with the other of the pair of electrodes which serves as a cathode.

As described above, the organic compound used in one embodiment of the present invention has a relatively deep HOMO level (specifically, lower than or equal to −5.7 eV). Thus, even when an organic compound used in a layer in contact with the cathode side of the layer containing the composite material (an organic compound used in a layer which is provided between the cathode and the layer containing the composite material and is in contact with the layer containing the composite material) (an organic compound used in a hole-transport layer, a light-emitting layer, or the like) has a relatively deep HOMO level (e.g., −6.0 eV), holes can be efficiently injected from the composite material to the organic compound. Needless to say, even when the organic compound has a shallow HOMO level (e.g., −5.0 eV), holes can be efficiently injected from the composite material to the organic compound. Therefore, the HOMO level of the organic compound contained in the layer (hereinafter, referred to as first layer) which is in contact with the cathode side of the layer containing the composite material (which is provided between the cathode and the layer containing the composite material and is in contact with the layer containing the composite material) is preferably higher than or equal to −6.0 eV and lower than or equal to −5.0 eV.

The difference in HOMO level between the composite material and the organic compound is preferably small and preferably within 0.2 eV. In view of reducing the difference in the HOMO level between the organic compound used in the first layer and the organic compound used in the composite material as described above, an organic compound, the rings of which are all benzene rings (the number of the benzene rings is greater than or equal to 4 and less than or equal to 25, or the molecular weight is greater than or equal to 350 and less than or equal to 2000), is preferably used as the organic compound used in the first layer. For example, the same organic compound as the composite material may be used in the first layer. In particular, the plurality of benzene rings of the organic compound are preferably bonded at the ortho position or the meta position, in which case the amorphous property of a film is high; thus, the organic compound can be suitably used in the first layer. In addition, the organic compound has a high T1 level, and thus can be suitably used in a first layer especially in an element emitting phosphorescence.

From the same point of view, a light-emitting layer which is in contact with the first layer preferably contains an organic compound (particularly as a host material), the rings of which are all benzene rings (the number of the benzene rings is greater than or equal to 4 and less than or equal to 25, or the molecular weight of the organic compound is greater than or equal to 350 and less than or equal to 2000). For example, the same organic compound as the composite material may be used. In particular, the plurality of benzene rings of the organic compound are preferably bonded at the ortho position or the meta position, in which case the amorphous property of a film is high; thus, the organic compound can be suitably used (as a host material) in the light-emitting layer. In addition, the organic compound has a high T1 level, and thus can be suitably used (as a host material) in a light-emitting layer especially in an element emitting phosphorescence.

In other words, another embodiment of the present invention is a light-emitting element which includes a layer containing a light-emitting substance between a pair of electrodes. The layer containing a light-emitting substance includes, from the anode side, a layer containing the composite material, a first layer, and a light-emitting layer. The layer containing the composite material, the first layer, and the light-emitting layer each contain an organic compound, the rings of which are all benzene rings (the number of the benzene rings is greater than or equal to 4 and less than or equal to 25, or the molecular weight of the organic compound is greater than or equal to 350 and less than or equal to 2000).

The organic compounds contained in the layer containing the composite material, the first layer, and the light-emitting layer are preferably the same, in which case hole injection among these layers are efficient and synthesis costs can be cut down.

In the light-emitting layer, a first organic compound is dispersed in a second organic compound. The rings of the second organic compound are all benzene rings. The number of the benzene rings of the second organic compound is preferably greater than or equal to 4 and less than or equal to 25.

Another embodiment of the present invention is a light-emitting element which includes a first EL layer to an n-th EL layer (n is a natural number greater than or equal to 2) between a pair of electrodes and includes a layer containing the composite material between a k-th EL layer (k is a natural number greater than or equal to 1 and less than n) and a (k+1)-th EL layer. In other words, the composite material can be used for an intermediate layer (also referred to as charge-generation layer) in an organic EL light-emitting element including a stack of a plurality of light-emitting units (tandem organic EL light-emitting element). In that case, it is preferable to provide a layer containing an organic compound, the rings of which are all benzene rings (the number of the benzene rings is greater than or equal to 4 and less than or equal to 25, or the molecular weight of the organic compound is greater than or equal to 350 and less than or equal to 2000), so as to be in contact with the cathode side of the layer containing the composite material.

Another embodiment of the present invention is a light-emitting device including the above light-emitting element. Another embodiment of the present invention is an electronic device including the above light-emitting device in a display portion. Another embodiment of the present invention is a lighting device including the above light-emitting device in a light-emitting portion.

An organic compound represented by Structural Formula (112) which can be used for the composite material of one embodiment of the present invention is a novel substance, and thus is also included in the present invention. Therefore, another embodiment of the present invention is an organic compound represented by Structural Formula (112).

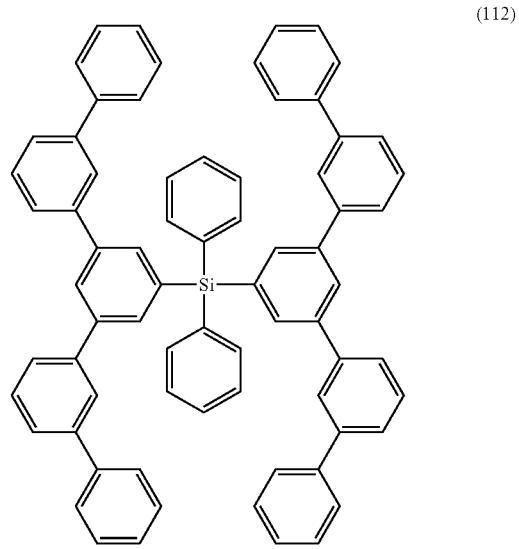 [SMILES: c1ccc(-c2cccc(-c3cc(-c4cccc(-c5ccccc5)c4)cc([Si](c4ccccc4)(c4ccccc4)c4cc(-c5cccc(-c6ccccc6)c5)cc(-c5cccc(-c6ccccc6)c5)c4)c3)c2)cc1]

(112)

According to one embodiment of the present invention, it is possible to provide a composite material which includes an organic compound and an inorganic compound and has a high carrier-transport property. It is also possible to provide a composite material which has an excellent property of carrier injection to an organic compound. It is also possible to provide a composite material in which light absorption due to charge transfer interaction is unlikely to occur. It is also possible to provide a composite material which has a high visible-light-transmitting property.

According to one embodiment of the present invention, it is possible to provide a light-emitting element which has high emission efficiency by application of the above composite material to the light-emitting element. It is also possible to provide a light-emitting element with low driving voltage. It is also possible to provide a light-emitting element with a long lifetime. It is possible to provide a light-emitting device including the light-emitting element, an electronic device including the light-emitting device, or a lighting device including the light-emitting device.

BRIEF DESCRIPTION OF THE DRAWINGS

FIGS. 3A and 3B illustrate a light-emitting device of one embodiment of the present invention.

FIGS. 5A to 5C illustrate a light-emitting device of one embodiment of the present invention.

DETAILED DESCRIPTION OF THE INVENTION

Figure 1A:
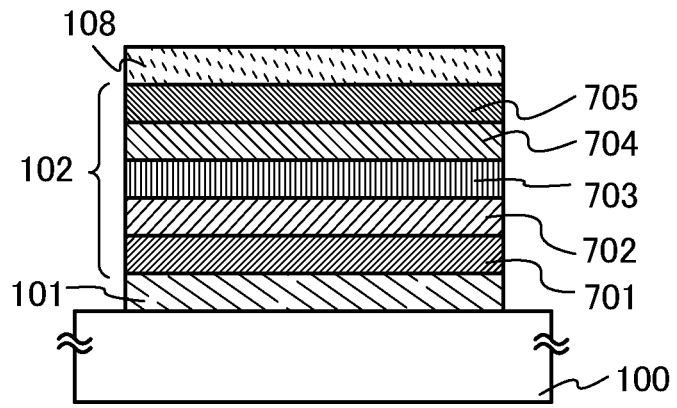
FIGS. 1A to 1C each illustrate a light-emitting element of one embodiment of the present invention.

Embodiments will be described in detail with reference to the drawings. Note that the present invention is not limited to the description below, and it is easily understood by those skilled in the art that various changes and modifications can be made without departing from the spirit and scope of the present invention. Therefore, the present invention should not be construed as being limited to the description in the embodiments below. Note that in the structures of the invention described below, the same portions or portions having similar functions are denoted by the same reference numerals in different drawings, and description of such portions is not repeated.

First, a difference between the background art of the present invention and the present invention will be briefly described. As disclosed in Patent Document 1, it is interpreted that in a composite material in which an aromatic amine and an electron-accepting inorganic compound are mixed, the electron-accepting inorganic compound takes electrons from the aromatic amine, and accordingly, holes and electrons are generated in the aromatic amine and the inorganic compound, respectively. In other words, it is interpreted that in such a composite material, the aromatic amine and the electron-accepting inorganic compound form a charge-transfer complex. Some composite materials utilizing such a phenomenon and having excellent carrier-transport and/or carrier-injection properties have been reported so far.

However, it is generally known that an absorption band based on charge-transfer interaction is generated in such composite materials. This absorption band is said to be generated in the deep-red to near-infrared region; in fact, in many cases, an absorption band is also generated in the visible light region. For example, a composite material including a mixture of 4,4'-bis[N-(1-naphthyl)-N-phenylamino]biphenyl (abbreviation: NPB or α-NPD) and vanadium oxide or a mixture of NPB and molybdenum oxide has an absorption band at around 500 nm, in addition to an absorption band at around 1300 nm. This is a great disadvantage for optical devices such as light-emitting elements.

The present inventors have found out that by mixing an organic compound, the rings of which are all benzene rings (the number of the benzene rings is greater than or equal to 4 and less than or equal to 25, or the molecular weight of the organic compound is greater than or equal to 350 and less than or equal to 2000) and a transition metal oxide or an inorganic compound exhibiting an electron-accepting property with respect to the organic compound, an excellent carrier-transport property and/or an excellent carrier-injection property can be obtained with no (almost no) light absorption due to charge-transfer interaction observed. Holes and electrons generated due to charge-transfer interaction have been considered to be factors for exhibiting a carrier-transport property and/or a carrier-injection property. Therefore, it can be said that the present invention, which can provide an excellent carrier-transport property and/or an excellent carrier-injection property with no clear light absorption due to charge-transfer interaction observed, contradicts the general theory and provides an unexpected, remarkable function.

As described above, the rings of the organic compound used in one embodiment of the present invention are all benzene rings. Benzene has a large energy gap between the HOMO level and the LUMO level. In addition, benzene has a high S1 level and a high T1 level. Therefore, when the rings of the organic compound are all the benzene rings, the organic compound can be designed so as not to have an absorption peak in the visible light region (so as to have little absorption in the visible light region). Accordingly, there is a great advantage in terms of improving a light-transmitting property.

Further, the HOMO level of benzene is very low. Therefore, the organic compound used in one embodiment of the present invention by itself is considered to have difficulty in receiving holes from a conductive material typified by Al or ITO (having a work function of approximately 3 eV to 5 eV) in spite of having an excellent property of hole injection to another organic compound. However, formation of a composite material as in one embodiment of the present invention enables the problem in hole injection from an electrode to be overcome while maintaining an excellent property of hole injection to another organic compound. When the composite material is used for a light-emitting element, such a property of the composite material contributes to a reduction in driving voltage. In addition, the high light-transmitting property of the composite material enables emission efficiency to be increased. Furthermore, a deep HOMO level is likely to prevent carrier accumulation in a light-emitting element, thus leading to a longer lifetime.

Embodiments of the present invention will be described below with specific examples.

Embodiment 1

In this embodiment, a composite material of one embodiment of the present invention will be described.

A composite material of one embodiment of the present invention is a composite material of an organic compound having a particular skeleton and an inorganic compound. There is no limitation on a method of preparing the composite material of one embodiment of the present invention; for example, it can be formed by a co-evaporation method in which the organic compound and the inorganic compound are deposited at the same time. The mixing ratio, in mass ratio, of the organic compound to the inorganic compound in the composite material of one embodiment of the present invention is preferably approximately 8:1 to 1:2 (=Organic compound: inorganic compound), and more desirably, 4:1 to 1:1 (=Organic compound: inorganic compound). When the composite material is formed by a co-evaporation method, the mixing ratio can be controlled by separately adjusting the deposition rates for the organic compound and the inorganic compound.

An organic compound that can be used for the composite material of one embodiment of the present invention is an organic compound, the rings of which are all benzene rings and which has greater than or equal to 4 and less than or equal to 25 benzene rings. An organic compound that can be used for the composite material of one embodiment of the present invention is an organic compound, the rings of which are all benzene rings and which has a molecular weight greater than or equal to 350 and less than or equal to 2000.

The organic compound may include an alkyl group having 1 to 6 carbon atoms or a trialkylsilyl group as a substituent. The organic compound may have benzene rings cross-linked with silicon.

The composite material including the organic compound has a high carrier-transport property. The above-described composite material also has a good property of carrier injection to an organic compound. Further, in the composite material, light absorption due to charge-transfer interaction with an inorganic compound is unlikely to occur. Furthermore, the composite material has a high light-transmitting property.

In the composite material including the organic compound, the occurrence of light absorption due to charge-transfer interaction can be suppressed and an absorption peak of the organic compound itself can also be controlled so as to appear at a shorter wavelength than visible-light wavelengths. Accordingly, the composite material can have a high light-transmitting property.

Benzene is an aromatic hydrocarbon and thus is an important conjugated ring in exhibiting a carrier-transport property (especially hole-transport property). At the same time, benzene is a conjugated ring with a wide energy gap. Accordingly, when the rings of the organic compound are all benzene rings, it is possible not only to suppress the occurrence of light absorption due to charge transfer interaction but also to control an absorption peak of the organic compound so that the absorption peak appears at a shorter wavelength than the visible-light wavelengths. Thus, with the use of the organic compound, the composite material can have a high light-transmitting property.

Although there is no particular limitation on the method of forming the composite material, it is preferable that the organic compound and an inorganic compound be co-evaporated. In that case, it is desirable that the organic compound vaporize easily. Therefore, in terms of molecular weight, the molecular weight of the organic compound is preferably less than or equal to 2000. When an alkyl chain or the like is bonded to the organic compound and the composite material is prepared through a wet process (a method in which a solution is used to form a film) or the like, the molecular weight may be greater than or equal to 2000.

The results of experiments and studies conducted by the present inventors have shown that when the mixing ratio of an inorganic compound to an aromatic hydrocarbon compound (e.g., an anthracene compound) is high, crystallization of a composite material formed by mixing the inorganic compound and the aromatic hydrocarbon compound can be suppressed, but a small absorption peak due to charge-transfer interaction between the inorganic compound and the skeleton of the aromatic hydrocarbon compound (e.g., anthracene skeleton) becomes large in some cases. In contrast, as described in one embodiment of the present invention, in the case of using an organic compound, the rings of which are all benzene rings (the number of the benzene rings is greater than or equal to 4 and less than or equal to 25, or the molecular weight of the organic compound is greater than or equal to 350 and less than or equal to 2000), even when the ratio of an inorganic compound to the organic compound is high, an additional absorption peak is unlikely to occur. Thus, with transmittance kept high, the crystallization of the composite material is suppressed and the film quality thereof is stabilized. Thus, in the case of using the composite material of one embodiment of the present invention, even when the ratio of an inorganic compound to an organic compound is made high in order to suppress crystallization, the ratio is not limited, and an absorption peak due to charge-transfer interaction can be prevented from being observed in the visible light region.

Thus, a film formation process can be simplified. In the case of the composite material of one embodiment of the present invention, specifically, even in a film having a mass ratio of the organic compound to the inorganic compound of 4:2, light absorption due to charge-transfer interaction is unlikely to occur, and almost no significant absorption peak is observed in regions ranging from the visible light region to the infrared region.

It is preferable that the HOMO level of the organic compound included in the above composite material of one embodiment of the present invention be lower than or equal to −5.7 eV when measured by photoelectron spectroscopy. As described above, benzene has a very low HOMO level. Thus, the organic compound, which is used in one embodiment of the present invention, by itself can easily have a low HOMO level lower than or equal to −5.7 eV.

In the case where the organic compound has a low HOMO level, it can be considered that the heterocyclic compound has an excellent hole-injection property to another organic compound, but has difficulty receiving holes from a conductive material typified by Al or ITO (having a work function of approximately 3 eV to 5 eV). On the other hand, by formation of such a composite material as in one embodiment of the present invention, it becomes possible to overcome the problem of a hole-injection property from an electrode while maintaining an excellent hole-injection property to another organic compound. Such properties of the composite material contribute to a reduction in driving voltage when the composite material is used for a light-emitting element. Its high light-transmitting property enables emission efficiency to increase. Furthermore, the deep HOMO level probably can prevent carrier accumulation in a light-emitting element, leading to a longer lifetime.

Examples of organic compounds that can be used for the composite material of one embodiment of the present invention are represented by the following structural formulae (100) to (112).

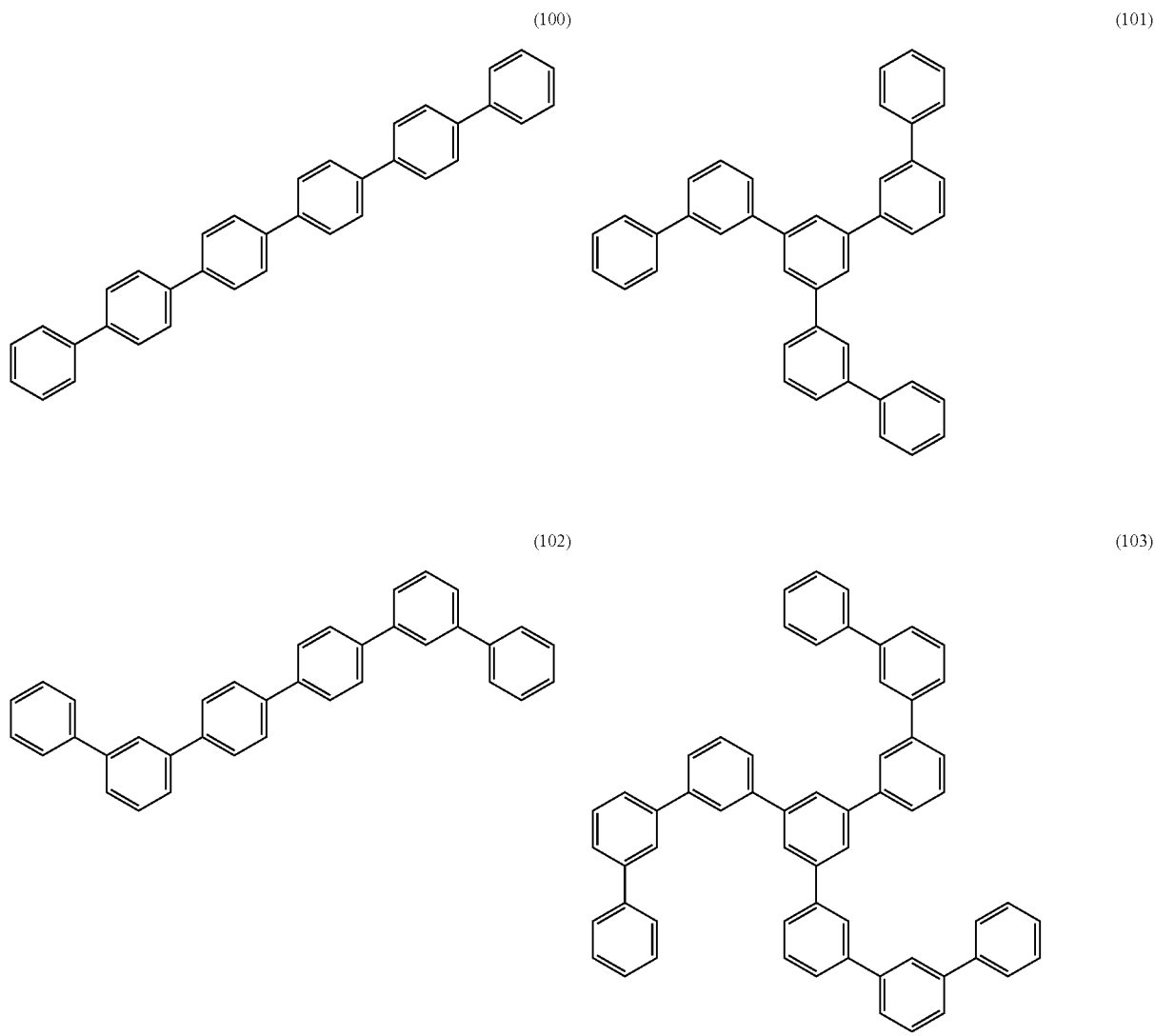

-continued
(104)
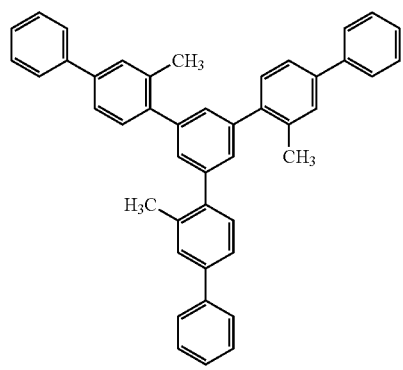
(105)
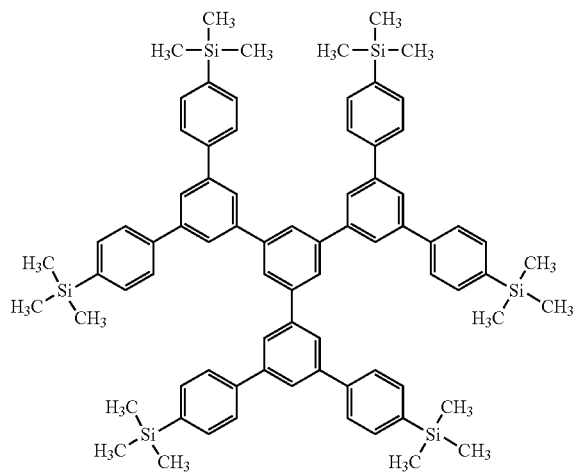
(106)
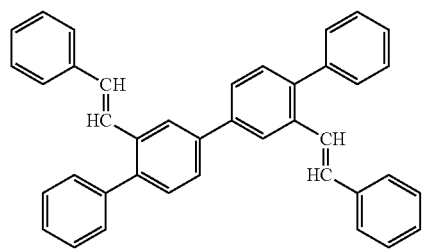
(107)
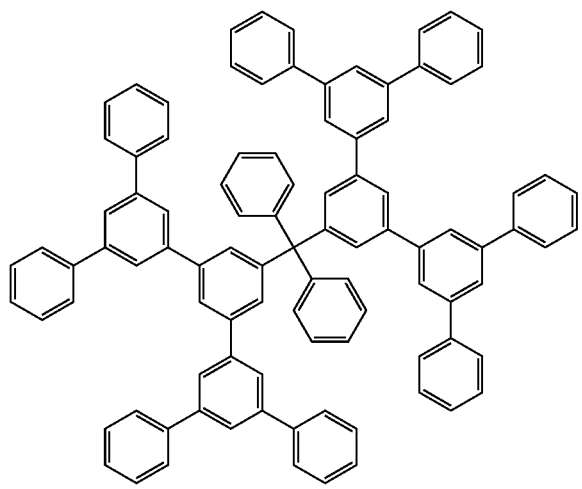
(108)
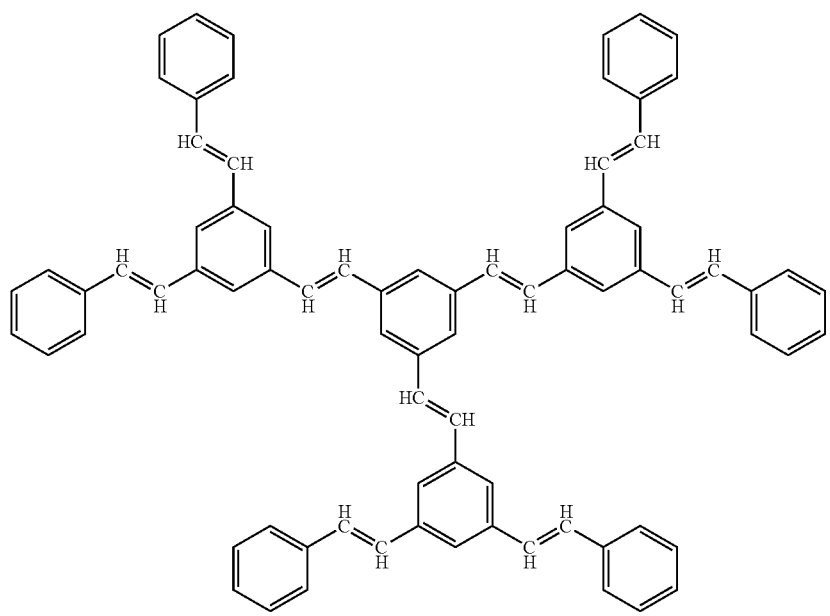

-continued (109)
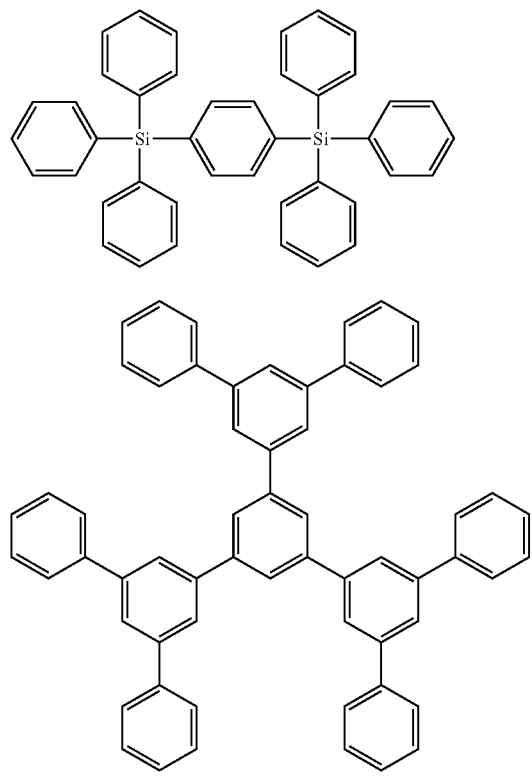

(110)
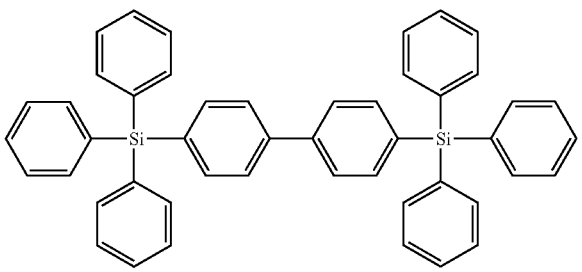

(111)
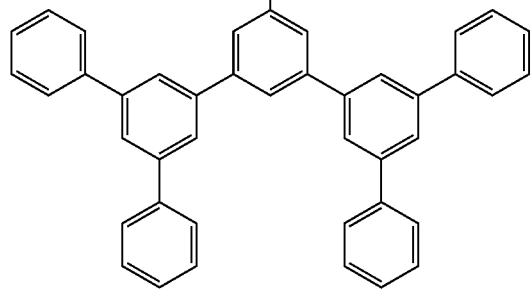

(112)
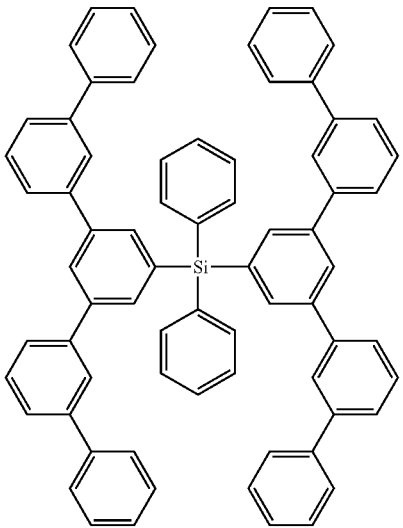

Next, an inorganic compound that can be used for the composite material of one embodiment of the present invention will be described.

An inorganic compound exhibiting an electron-accepting property with respect to the organic compound used for the composite material of one embodiment of the present invention can be used. Iron(III) chloride, aluminum chloride, and the like are examples of inorganic compounds having a high electron-accepting property.

Alternatively, a transition metal oxide can be used as an inorganic compound for the composite material of one embodiment of the present invention. Preferably, it is desirable to use an oxide of a metal belonging to group 4 to 8 of the periodic table. It is particularly preferable to use titanium oxide, vanadium oxide, tantalum oxide, molybdenum oxide, tungsten oxide, rhenium oxide, ruthenium oxide, chromium oxide, zirconium oxide, hafnium oxide, or silver oxide. Molybdenum oxide is particularly easy to handle among them, because it is easily deposited by evaporation, has a low hygroscopic property, and is stable.

A transition metal oxide is considered not to have a very high electron-accepting property (considered to have low reactivity), as compared to a strong Lewis acid such as iron (III) chloride mentioned above. In the composite material of one embodiment of the present invention, as described above, absorption due to charge-transfer interaction less occurs (or light absorption hardly occurs). It is difficult to prove from these that a transition metal oxide acts as an electron acceptor in a general sense in the present invention. On the other hand, as described in the following Examples, there is an experimental fact that the composite material in this embodiment conducts a larger amount of current than the organic compound alone can do, when an electric field is applied. Thus, it is probable that in the composite material of one embodiment of the present invention, use of a transition metal oxide facilitates carrier generation at least with an assistance of application of an electric field. Therefore, in this specification, an inorganic compound (such as a transition metal oxide mentioned above) in the composite material is regarded as having an electron-accepting property as long as carriers are generated at least with an assistance of application of an electric field.

As described above, the composite material of one embodiment of the present invention is a material having a low HOMO level and a high carrier-transport property. In addition, the composite material of one embodiment of the present invention is a material having an excellent property of carrier injection to an organic compound. Further, the composite material of one embodiment of the present invention is a material in which absorption due to charge-transfer interaction is unlikely to occur. Furthermore, the composite material of one embodiment of the present invention is a material having a high light-transmitting property.

Therefore, the composite material of one embodiment of the present invention can be used for a light-emitting element or a semiconductor element such as a photoelectric conversion element or a transistor.

Furthermore, the composite material of one embodiment of the present invention has excellent properties of carrier-transport and carrier injection to an organic compound and can accordingly achieve low driving voltage when used for a light-emitting element or the like.

The composite material of one embodiment of the present invention has a light-transmitting property and can accordingly achieve high emission efficiency when used for a light-emitting element or the like.

The composite material of one embodiment of the present invention suppresses charge accumulation and can accordingly achieve an element having a long lifetime when used for a light-emitting element or the like.

Further, the composite material of one embodiment of the present invention can be used for an organic thin-film solar cell. The composite material of one embodiment of the present invention has an excellent carrier-transport property, and thus can be used for a carrier-transport layer, a carrier-injection layer, or a charge-generation layer.

Note that this embodiment can be freely combined with any of the other embodiments as appropriate.

Embodiment 2

In this embodiment, a light-emitting element of one embodiment of the present invention will be described with reference to FIGS. 1A to 1C.

In a light-emitting element of this embodiment, an EL layer (a layer containing a light-emitting substance) is interposed between a pair of electrodes. The EL layer includes at least a layer containing the composite material of one embodiment of the present invention described in Embodiment 1 and a light-emitting layer. The EL layer may additionally include another layer. For example, the EL layer may include a layer containing a substance having a high carrier-injection property or a layer containing a substance having a high carrier-transport property so that a light-emitting region is formed in a region away from the electrodes, that is, so that carriers recombine in a region away from the electrodes. In this specification, the layer containing a substance having a high carrier-injection or a high carrier-transport property is also referred to as functional layer which functions, for instance, to inject or transport carriers. As the functional layer, a hole-injection layer, a hole-transport layer, an electron-injection layer, an electron-transport layer, or the like can be used. Note that in this embodiment, the layer containing the composite material of one embodiment of the present invention is used as a hole-injection layer.

It is preferable that one or more layers (such as a hole-transport layer) be provided between the layer containing the composite material of one embodiment of the present invention and the light-emitting layer. Accordingly, it is possible to suppress quenching (a decrease in efficiency) caused by transfer of excitation energy generated in the light-emitting layer to the layer containing the composite material, and it is possible to obtain a more efficient element.

In the light-emitting element illustrated in FIG. 1A, an EL layer 102 is provided between a first electrode 101 and a second electrode 108. In the EL layer 102, a hole-injection layer 701, a hole-transport layer 702, a light-emitting layer 703, an electron-transport layer 704, and an electron-injection layer 705 are stacked in this order over the first electrode 101. Note that, in the light-emitting element described in this embodiment, the first electrode 101 functions as an anode and the second electrode 108 functions as a cathode.

As a support of the light-emitting element (see a substrate 100 in FIG. 1A), a glass substrate, a quartz substrate, a plastic substrate, or the like can be used, for example. Furthermore, a flexible substrate may be used. A flexible substrate is a substrate that can be bent (is flexible); examples of the flexible substrate include a plastic substrate made of a polycarbonate, a polyarylate, or a polyethersulfone, and the like. Alternatively, a film (made of polypropylene, polyester, polyvinyl fluoride, polyvinyl chloride, or the like), a film on which an inorganic substance is deposited, or the like can be used. Note that materials other than these can be used as long as they can function as a support of the light-emitting element.

For the first electrode 101, any of a variety of metals, alloys, conductive compounds, mixtures thereof, and the like can be used. Examples include ITO, indium oxide-tin oxide containing silicon or silicon oxide, indium oxide-zinc oxide (indium zinc oxide), indium oxide containing tungsten oxide and zinc oxide (IWZO), and the like. Films of these conductive metal oxides are usually formed by sputtering; however, a sol-gel method or the like may also be used. For example, a film of indium zinc oxide can be formed by a sputtering method using a target in which zinc oxide is added to indium oxide at 1 wt % to 20 wt %. An IWZO film can be formed by a sputtering method using a target in which tungsten oxide is added to indium oxide at 0.5 wt % to 5 wt % and zinc oxide is added to indium oxide at 0.1 wt % to 1 wt %. Other examples include platinum, nickel, tungsten, chromium, molybdenum, iron, cobalt, copper, palladium, nitrides of metal materials (e.g., titanium nitride), and the like.

As a material of the first electrode 101, it is preferable to use a material having a high work function (a work function higher than or equal to 4.0 eV). Note that in a light-emitting element having a structure in which the first electrode 101 and the layer containing the composite material of one embodiment of the present invention are in contact with each other, a material used for the first electrode 101 is not limited to a material having a high work function and can be a material having a low work function. For example, aluminum, silver, an alloy containing aluminum (e.g., Al—Si), or the like can also be used.

The hole-injection layer 701 is a layer containing the composite material of one embodiment of the present invention.

The organic compound (see Embodiment 1) used for the composite material of one embodiment of the present invention has a low HOMO level and an excellent hole-injection property into the hole-transport layer 702 and the light-emitting layer 703. On the other hand, an injection barrier is generated between the first electrode 101 and the heterocyclic compound, and holes are not easily injected from the first electrode 101.

However, in the light-emitting element of one embodiment of the present invention, the composite material of one embodiment of the present invention is used for the hole-injection layer 701; thus, the injection barrier between the first electrode 101 and the hole-injection layer 701 can be reduced. Therefore, it is possible to obtain an element having a low injection barrier from the first electrode 101 to the light-emitting layer 703 and a high carrier-injection property, and it is possible to provide a light-emitting element having low driving voltage.

Furthermore, the composite material of one embodiment of the present invention has high carrier-generation efficiency and a high carrier-transport property. Therefore, with the use of the composite material of one embodiment of the present invention, it is possible to obtain a light-emitting element with high emission efficiency.

In addition, with the organic compound, a high absorption peak is not generated in the visible light region. Furthermore, the organic compound has a low HOMO level, and absorption due to charge-transfer interaction with the inorganic compound is unlikely to occur. Thus, the composite material of one embodiment of the present invention is unlikely to exhibit an absorption peak in the visible light region, and has a high light-transmitting property. Therefore, this also shows that with the use of the composite material of one embodiment of the present invention, it is possible to obtain a light-emitting element with high emission efficiency.

The composite material of one embodiment of the present invention can suppress charge accumulation; therefore, a light-emitting element having a long lifetime can be provided.

There is no limitation on the emission color of a light-emitting element to which the composite material of one embodiment of the present invention is applied. In addition, it does not matter whether a light-emitting element to which the composite material of one embodiment of the present invention is applied exhibits fluorescence or phosphorescence. In any light-emitting element, the composite material of one embodiment of the present invention hardly causes absorption of emission energy and reduction of efficiency, and thus can be suitably used for a hole-injection layer.

The hole-transport layer 702 is a layer which contains a substance with high hole-transport properties. As a material of the hole-transport layer 702, the organic compound used for the composite material of one embodiment of the present invention may be used. Other examples of the substance having a high hole-transport property are aromatic amine compounds such as 4,4'-bis[N-(1-naphthyl)-N-phenylamino]biphenyl (abbreviation: NPB or α-NPB), N,N'-bis(3-methylphenyl)-N,N'-diphenyl-[1,1'-biphenyl]-4,4'-diamine (abbreviation: TPD), 4-phenyl-4'-(9-phenylfluoren-9-yl)triphenylamine (abbreviation: BPAFLP), 4,4'-bis[N-(9,9-dimethylfluoren-2-yl)-N-phenylamino]biphenyl (abbreviation: DFLDPBi), and 4,4'-bis[N-(spiro-9,9'-bifluoren-2-yl)-N-phenylamino]biphenyl (abbreviation: BSPB). The substances mentioned here are mainly ones that have a hole mobility of $10^{-6}$ cm$^2$V/s or higher. However, other substances than the above materials may also be used as long as the substances have higher hole-transport properties than electron-transport properties. Note that the layer containing a substance having a high hole-transport property is not limited to a single layer and may be a stack of two or more layers containing any of the above substances.

For the hole-transport layer 702, a carbazole derivative such as 4,4'-di(N-carbazolyl)biphenyl (abbreviation: CBP), 9-[4-(10-phenyl-9-anthryl)phenyl]-9H-carbazole (abbreviation: CzPA), or 9-phenyl-3-[4-(10-phenyl-9-anthryl)phenyl]-9H-carbazole (abbreviation: PCzPA) or an anthracene derivative such as 2-tert-butyl-9,10-di(2-naphthyl)anthracene (abbreviation: t-BuDNA), 9,10-di(2-naphthyl)anthracene (abbreviation: DNA), or 9,10-diphenylanthracene (abbreviation: DPAnth) may be used.

In particular, the organic compound in the composite material of one embodiment of the present invention has a low HOMO level; therefore, a material having a low HOMO level can be used also for the hole-transport layer. With such a structure, it is possible to prevent charge accumulation at the interface between the light-emitting layer and the hole-transport layer, and it is possible to extend the lifetime of the light-emitting element. Specifically, it is preferable that the HOMO level of the hole-transport layer be lower than or equal to −5.6 eV. From such a point of view, a carbazole derivative, a dibenzothiophene derivative, a dibenzofuran derivative, an anthracene derivative, or the like is preferable as a compound used for the hole-transport layer. The organic compound used for the composite material of one embodiment of the present invention may also be used. In this structure, the organic compound used for the composite material of one embodiment of the present invention is preferably used for the hole-injection layer and the hole-transport layer, in which case the HOMO levels are close to each other to reduce carrier injection barrier. In particular, the organic compound used for the composite material of one embodiment of the present invention which is used for the hole-injection layer and the organic compound used for the hole-transport layer are preferably the same materials, in which case hole injection between these layers is efficient.

Note that for the hole-transport layer 702, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD) can also be used.

The light-emitting layer 703 is a layer containing a light-emitting organic compound. As the light-emitting organic compound, for example, a fluorescent compound which exhibits fluorescence or a phosphorescent compound which exhibits phosphorescence can be used.

As the fluorescent compound that can be used for the light-emitting layer 703, a material for blue light emission, a material for green light emission, a material for yellow light emission, and a material for red light emission are given. As examples of the material for blue light emission, the following are given: N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(10-phenyl-9-anthryl)-4'-(9-phenyl-9H-carbazol-3-yl)triphenylamine (abbreviation: PCBAPA), and the like. As examples of the material for green light emission, the following are given: N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), and the like. As examples of the material for yellow light emission, rubrene, 5,12-bis(1,1'-biphenyl-4-yl)-6,11-diphenyltetracene (abbreviation: BPT), and the like are given. As examples of the material for red light emission, N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), and the like are given.

The organic compound used for the composite material of one embodiment of the present invention exhibits purple to blue fluorescence. Therefore, the organic compound used for the composite material of one embodiment of the present invention can be used as a fluorescent compound in the light-emitting layer 703.

As the phosphorescent compound that can be used for the light-emitting layer 703, a material for blue light emission, a material for green light emission, a material for yellow light emission, a material for orange light emission, and a material for red light emission are given. As examples of the material for blue light emission, the following are given: bis[2-(4',6'-difluorophenyl)pyridinato-N,C$^{2'}$]iridium(III)tetrakis(1-pyrazolyl)borate (abbreviation: FIr6); bis[2-(4',6'-difluorophenyl)pyridinato-N,C$^{2'}$]iridium(III)picolinate (abbreviation: FIrpic); bis{2-[3',5'-bis(trifluoromethyl)phenyl]pyridinato-N,C$^{2'}$}iridium(III)picolinate (abbreviation: [Ir(CF$_3$ppy)$_2$(pic)]); bis[2-(4',6'-difluorophenyl)pyridinato-N, C$^{2'}$]iridium(III)acetylacetonate (abbreviation: FIr(acac));

and the like. As examples of the material for green light emission, the following are given: tris(2-phenylpyridinato-N, $C^{2'}$)iridium(III) (abbreviation: [Ir(ppy)$_3$]), bis[2-phenylpyridinato-N, $C^{2'}$]iridium(III)acetylacetonate (abbreviation: [Ir(ppy)$_2$(acac)]), bis(1,2-diphenyl-1H-benzimidazolato) iridium(III)acetylacetonate (abbreviation: [Ir(pbi)$_2$(acac)]), bis(benzo[h]quinolinato)iridium(III)acetylacetonate (abbreviation: [Ir(bzq)$_2$(acac)]), tris(benzo[h]quinolinato)iridium (III) (abbreviation: [Ir(bzq)$_3$]), and the like. As examples of the material for yellow light emission, the following are given: bis(2,4-diphenyl-1,3-oxazolato-N, $C^{2'}$)iridium(III) acetylacetonate (abbreviation: [Ir(dpo)$_2$(acac)]), bis[2-(4'-perfluorophenylphenyl)pyridinato]iridium(III)acetylacetonate (abbreviation: [Ir(p-PF-ph)$_2$(acac)]), bis(2-phenylbenzothiazolato-N,$C^{2'}$)iridium(III)acetylacetonate (abbreviation: [Ir(bt)$_2$(acac)]) (acetylacetonato)bis[2,3-bis(4-fluorophenyl)-5-methylpyrazinato]iridium(III) (abbreviation: [Ir(Fdppr-Me)$_2$(acac)]), (acetylacetonato)bis{2-(4-methoxyphenyl)-3,5-dimethylpyrazinato}iridium(III) (abbreviation: [Ir(dmmoppr)$_2$(acac)]), and the like. As examples of the material for orange light emission, the following are given: tris(2-phenylquinolinato-N,$C^{2'}$)iridium (III) (abbreviation: [Ir(pq)$_3$]), bis(2-phenylquinolinato-N, $C^{2'}$)iridium(III)acetylac etonate (abbreviation: [Ir(pq)$_2$(acac)]), (acetylacetonato)bis(3,5-dimethyl-2-phenylpyrazinato)iridium(III) (abbreviation [Ir(mppr-Me)$_2$(acac)]), (acetylacetonato)bis(5-isopropyl-3-methyl-2-phenylpyrazinato)iridium(III) (abbreviation: [Ir(mppr-iPr)$_2$(acac)]), and the like. As examples of the material for red light emission, organometallic complexes such as bis[2-(2'-benzo[4,5-a]thienyl)pyridinato-N, $C^{3'}$)iridium(III)acetylacetonate (abbreviation: [Ir(btp)$_2$(acac)]), bis(1-phenylisoquinolinato-N,$C^{2'}$) iridium(III)acetylacetonate (abbreviation: [Ir(piq)$_2$(acac)]), (acetylacetonato)bis[2,3-bis(4-fluorophenyl)quinoxalinato] iridium(III) (abbreviation: [Ir(Fdpq)$_2$(acac)]), (acetylacetonato)bis(2,3,5-triphenylpyrazinato)iridium(III) (abbreviation: [Ir(tppr)$_2$(acac)]), (dipivaloylmethanato)bis(2,3,5-triphenylpyrazinato)iridium(III) (abbreviation: [Ir(tppr)$_2$(dpm)]), and (2,3,7,8,12,13,17,18-octaethyl-21H,23H-porphyrin)platinum(II) (abbreviation: PtOEP). In addition, rare-earth metal complexes, such as tris(acetylacetonato) (monophenanthroline)terbium(III) (abbreviation: Tb(acac)$_3$(Phen)), tris(1,3-diphenyl-1,3-propanedionato) (monophenanthroline)europium(III) (abbreviation: Eu(DBM)$_3$(Phen)), and tris[1-(2-thenoyl)-3,3,3-trifluoroacetonato] (monophenanthroline)europium(III) (abbreviation: Eu(TTA)$_3$(Phen)), exhibit light emission from rare-earth metal ions (electron transition between different multiplicities), and thus can be used as phosphorescent compounds.

Note that the light-emitting layer 703 may have a structure in which the above light-emitting organic compound (a guest material) is dispersed in another substance (a host material). A variety of substances can be used as the host material, and it is preferable to use a substance that has a lowest unoccupied molecular orbital level (LUMO level) higher than that of a guest material and has a HOMO level lower than that of the guest material. In the case where the guest material is a fluorescent compound, the host material preferably has a high singlet excitation energy level (S1 level). In the case where the guest material is a phosphorescent compound, the host material preferably has a high triplet excitation energy level (T1 level).

The organic compound used for the composite material of one embodiment of the present invention has a high LUMO level, a low HOMO level, a high S1 level, and a high T1 level. Therefore, the organic compound can be used as a host material for a fluorescent compound which emits visible light or as a host material for a phosphorescent compound which emits visible light.

As specific examples of the host material, the following are given: metal complexes such as tris(8-quinolinolato)aluminum(III) (abbreviation: Alq), tris(4-methyl-8-quinolinolato) aluminum(III) (abbreviation: Almq$_3$), bis(10-hydroxybenzo [h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: Zn(BOX)$_2$), and bis[2-(2-benzothiazolyl)phenolato] zinc(II) (abbreviation: Zn(BTZ)$_2$); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2"-(1,3,5-benzenetriyl)tris(1-phenyl-1H-benzimidazole) (abbreviation: TPBI), bathophenanthroline (abbreviation: BPhen), and bathocuproine (BCP); condensed aromatic compounds such as 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl) diphenanthrene (abbreviation: DPNS2), 3,3',3"-(benzene-1, 3,5-triyl)tripyrene (abbreviation: TPB3), 9,10-diphenylanthracene (abbreviation: DPAnth), and 6,12-dimethoxy-5,11-diphenylchrysene; aromatic amine compounds such as N,N-dipheyl-9-[4-(10-phenyl-9-anthryl) phenyl]-9H-carbazol-3-amine (abbreviation: CzAlPA), 4-(10-phenyl-9-anthryl)triphenylamine (abbreviation: DPhPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), NPB (or α-NPD), TPD, DFLDPBi, and BSPB; and the like Plural kinds of materials can be used as the host material. For example, in order to suppress crystallization, a substance such as rubrene which suppresses crystallization may be further added. In addition, NPB, Alq, or the like may be further added in order to efficiently transfer energy to the guest material.

When a structure in which a guest material is dispersed in a host material is employed, crystallization of the light-emitting layer 703 can be suppressed. Further, concentration quenching due to high concentration of the guest material can be suppressed.

For the light-emitting layer 703, a high molecular compound can be used. Specifically, a material for blue light emission, a material for green light emission, and a material for orange to red light emission are given. As examples of the material for blue light emission, the following are given: poly(9,9-dioctylfluorene-2,7-diyl) (abbreviation: PFO), poly [(9,9-dioctylfluorene-2,7-diyl-co-(2,5-dimethoxybenzene-1, 4-diyl)] (abbreviation: PF-DMOP), poly{(9,9-dioctylfluorene-2,7-diyl)-co-[N,N'-di-(p-butylphenyl)-1,4-diaminobenzene]}(abbreviation: TAB-PFH), and the like. As examples of the material for green light emission, the following are given: poly(p-phenylenevinylene) (abbreviation: PPV), poly[(9,9-dihexylfluorene-2,7-diyl)-alt-co-(benzo[2, 1,3]thiadiazole-4,7-diyl)] (abbreviation: PFBT), poly[(9,9-dio ctyl-2,7-divinylenfluorenylene)-alt-co-(2-methoxy-5-(2-ethylhexyloxy)-1,4-phenylene)], and the like. As examples of the material for orange to red light emission, the following are given: poly[2-methoxy-5-(2'-ethylhexoxy)-1,4-phenylenevinylene] (abbreviation: MEH-PPV), poly(3-butylthiophene-2,5-diyl) (abbreviation: R4-PAT), poly {[9,9-dihexyl-2,7-bis (1-cyanovinylene)fluorenylene]-alt-co-[2,5-bis(N,N'-diphenyl amino)-1,4-phenylene]}, poly{[2-methoxy-5-(2-ethylhexyloxy)-1,4-bis(1-cyanovinylenephenylene)]-alt-co-[2,5-bis(N,N'-diphenylamino)-1,4-phenylene]} (abbreviation: CN—PPV-DPD), and the like.

Further, by providing a plurality of light-emitting layers and making emission colors of the light-emitting layers different, light emission of a desired color can be obtained from the light-emitting element as a whole. For example, the emission colors of first and second light-emitting layers are complementary in a light-emitting element having the two light-emitting layers, whereby the light-emitting element can be made to emit white light as a whole. Note that "complementary colors" refer to colors that produces an achromatic color when mixed. In other words, when lights obtained from substances which emit complementary colors are mixed, white emission can be obtained. This can be applied to a light-emitting element having three or more light-emitting layers.

The electron-transport layer 704 is a layer containing a substance having a high electron-transport property. As the substance having a high electron-transport property, for example, a metal complex having a quinoline skeleton or a benzoquinoline skeleton, such as Alq, Almq$_3$, BeBq$_2$, or BAlq, can be used. A metal complex having an oxazole-based or thiazole-based ligand, such as Zn(BOX)$_2$ or Zn(BTZ)$_2$ can also be used. Besides the metal complexes, PBD, OXD-7, TAZ, BPhen, BCP, or the like can also be used. The substances mentioned here are mainly ones that have an electron mobility of $10^{-6}$ cm$^2$/Vs or higher. The layer containing a substance having a high hole-transport property is not limited to a single layer and may be a stack of two or more layers containing any of the above substances. Further, the electron-transport layer is not limited to a single layer, and may be a stack of two or more layers containing any of the above substances.

The electron-injection layer 705 is a layer containing a substance having a high electron-injection property. For the electron-injection layer 705, an alkali metal, an alkaline earth metal, or a compound thereof, such as lithium, cesium, calcium, lithium fluoride, cesium fluoride, calcium fluoride, or lithium oxide, can be used. In addition, a rare earth metal compound such as erbium fluoride can also be used. Any of the above substances for forming the electron-transport layer 704 can also be used.

Note that the hole-injection layer 701, the hole-transport layer 702, the light-emitting layer 703, the electron-transport layer 704, and the electron-injection layer 705 which are described above can each be formed by a method such as an evaporation method (e.g., a vacuum evaporation method), an ink-jet method, or a coating method.

Figure 2A:
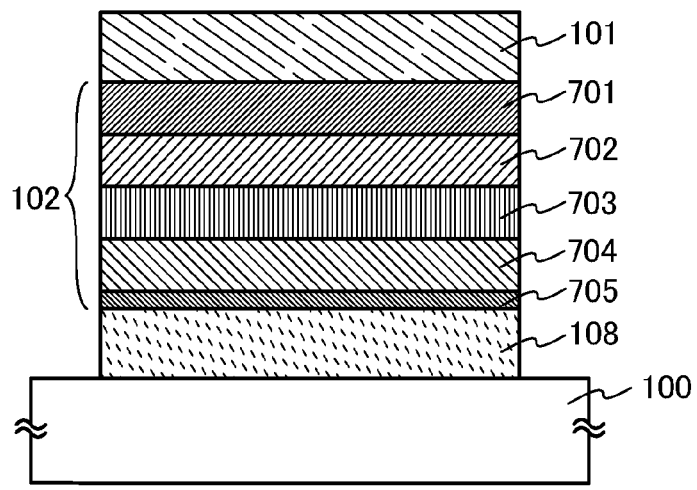
FIGS. 2A and 2B each illustrate a light-emitting element of one embodiment of the present invention.

In a light-emitting element illustrated in FIG. 2A, the EL layer 102 is provided between a pair of electrodes, the first electrode 101 and the second electrode 108, over the substrate 100. The EL layer 102 includes the hole-injection layer 701, the hole-transport layer 702, the light-emitting layer 703, the electron-transport layer 704, and the electron-injection layer 705. The light-emitting element in FIG. 2A includes the second electrode 108 serving as a cathode over the substrate 100, the electron-injection layer 705, the electron-transport layer 704, the light-emitting layer 703, the hole-transport layer 702, and the hole-injection layer 701 which are stacked over the second electrode 108 in this order, and the first electrode 101 provided thereover which serves as an anode.

Further, by forming EL layers to emit light of different colors from each other, a light-emitting element as a whole can provide light emission of a desired color. For example, by forming a light-emitting element having two EL layers such that the emission color of the first EL layer and the emission color of the second EL layer are complementary colors, the light-emitting element as a whole can provide white light emission. This can be applied to a light-emitting element having three or more EL layers.

Figure 1B:
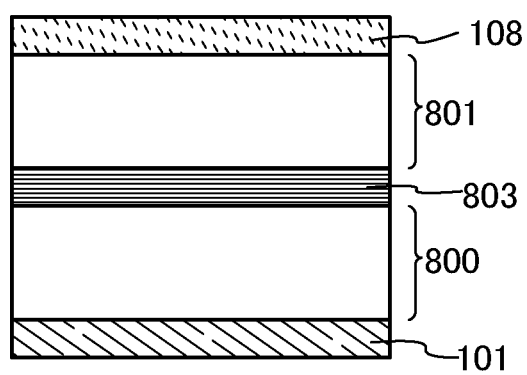

A plurality of EL layers may be stacked between the first electrode 101 and the second electrode 108 as illustrated in FIG. 1B. In that case, a charge-generation layer 803 is preferably provided between a first EL layer 800 and a second EL layer 801 which are stacked. The charge-generation layer 803 can be formed using the composite material of one embodiment of the present invention. The composite material of one embodiment of the present invention has high carrier generation efficiency and a high hole-transport property at the time of voltage application. Therefore, with the use of the composite material of one embodiment of the present invention, it is possible to obtain a light-emitting element with low driving voltage. In addition, it is possible to obtain a light-emitting element with high emission efficiency.

Also in this case, the organic compound used for the composite material of one embodiment of the present invention can be suitably used for the hole-transport layer in contact with the layer containing the composite material of one embodiment of the present invention or for the light-emitting layer in contact with the hole-transport layer.

In addition, the organic compound is unlikely to exhibit an absorption peak in the visible light region. Furthermore, the organic compound has a low HOMO level, and absorption due to charge-transfer interaction with the inorganic compound is unlikely to occur. Thus, the composite material of one embodiment of the present invention is unlikely to exhibit an absorption peak in the visible light region, and has a high light-transmitting property. Therefore, this also shows that with the use of the composite material of one embodiment of the present invention, it is possible to obtain a light-emitting element with high emission efficiency.

Further, the charge-generation layer 803 may have a stacked structure including a layer containing the composite material of one embodiment of the present invention and a layer containing another material. In that case, as the layer containing another material, a layer containing an electron donating substance and a substance with high electron-transport properties, a layer formed of a transparent conductive film, or the like can be used. As for a light-emitting element having such a structure, problems such as energy transfer and quenching hardly occur, and a light-emitting element which has both high emission efficiency and long lifetime can be easily obtained due to expansion in the choice of materials. Moreover, a light-emitting element which provides phosphorescence from one EL layer and fluorescence from another EL layer can be easily obtained. Note that this structure can be combined with any of the above structures of the EL layer.

Figure 2B:
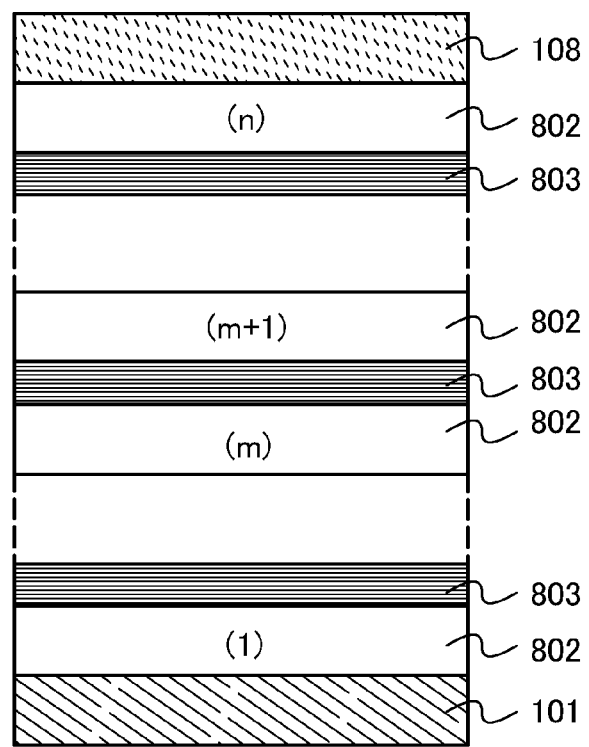

Similarly, a light-emitting element in which three or more EL layers 802 are stacked as illustrated in FIG. 2B can also be employed. A plurality of EL layers with a charge-generation layer positioned therebetween is provided between a pair of electrodes, as in the light-emitting element according to this embodiment, whereby it is possible to obtain an element having a long lifetime which can emit light at a high luminance while current density is kept low.

Figure 1C:
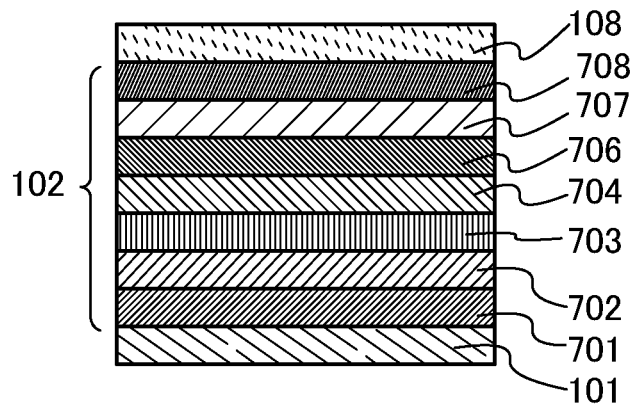

As illustrated in FIG. 1C, the EL layer may include the hole-injection layer 701, the hole-transport layer 702, the light-emitting layer 703, the electron-transport layer 704, an electron-injection buffer layer 706, an electron-relay layer 707, and a composite material layer 708 which is in contact with the second electrode 108, between the first electrode 101 and the second electrode 108.

It is preferable to provide the composite material layer 708 which is in contact with the second electrode 108, in which case damage caused to the EL layer 102 particularly when the second electrode 108 is formed by a sputtering method can be reduced. The composite material layer 708 can be formed using the composite material of one embodiment of the present invention.

Further, since the above composite material layer 708 functions as a charge generation layer, carriers can be efficiently injected from the second electrode 108 into the electron-relay layer 707 by passing through the composite material layer 708.

Further, by providing the electron-injection buffer layer 706, an injection barrier between the composite material layer 708 and the electron-transport layer 704 can be reduced; thus, electrons generated in the composite material layer 708 can be easily injected into the electron-transport layer 704.

A substance having a high electron-injection property, such as an alkali metal, an alkaline earth metal, a rare earth metal, a compound of the above metal (e.g., an alkali metal compound (e.g., an oxide such as lithium oxide, a halide, and a carbonate such as lithium carbonate or cesium carbonate), an alkaline earth metal compound (e.g., an oxide, a halide, and a carbonate), or a rare earth metal compound (e.g., an oxide, a halide, and a carbonate), can be used for the electron-injection buffer layer 706.

Further, in the case where the electron-injection buffer layer 706 contains a substance having a high electron-transport property and a donor substance, the donor substance is preferably added so that the mass ratio of the donor substance to the substance having a high electron-transport property is from 0.001:1 to 0.1:1. Note that as the donor substance, an organic compound such as tetrathianaphthacene (abbreviation: TTN), nickelocene, or decamethylnickelocene can be used as well as an alkali metal, an alkaline earth metal, a rare earth metal, a compound of the above metal (e.g., an alkali metal compound (including an oxide of lithium oxide or the like, a halide, and a carbonate such as lithium carbonate or cesium carbonate), an alkaline earth metal compound (including an oxide, a halide, and a carbonate), and a rare earth metal compound (including an oxide, a halide, and a carbonate). Note that as the substance having a high electron-transport property, a material similar to the material for the electron-transport layer 704 described above can be used.

Furthermore, the electron-relay layer 707 is preferably formed between the electron-injection buffer layer 706 and the composite material layer 708. The electron-relay layer 707 is not necessarily provided; however, by providing the electron-relay layer 707 having a high electron-transport property, electrons can be rapidly transported to the electron-injection buffer layer 706.

The structure in which the electron-relay layer 707 is sandwiched between the composite material layer 708 and the electron-injection buffer layer 706 is a structure in which the acceptor substance contained in the composite material layer 708 and the donor substance contained in the electron-injection buffer layer 706 are less likely to interact with each other, and thus their functions hardly interfere with each other. Therefore, an increase in driving voltage can be suppressed.

The electron-relay layer 707 contains a substance having a high electron-transport property and is formed so that the LUMO level of the substance having a high electron-transport property is located between the LUMO level of the acceptor substance contained in the composite material layer 708 and the LUMO level of the substance having a high electron-transport property contained in the electron-transport layer 704. In the case where the electron-relay layer 707 contains a donor substance, the donor level of the donor substance is controlled so as to be located between the LUMO level of the acceptor material contained in the composite material layer 708 and the LUMO level of the substance having a high electron-transport property contained in the electron-transport layer 704. As a specific value of the energy level, the LUMO level of the substance having a high electron-transport property contained in the electron-relay layer 707 is preferably greater than or equal to −5.0 eV, more preferably greater than or equal to −5.0 eV and less than or equal to −3.0 eV.

As the substance having a high electron-transport property contained in the electron-relay layer 707, a phthalocyanine-based material or a metal complex having a metal-oxygen bond and an aromatic ligand is preferably used.

As the phthalocyanine-based material contained in the electron-relay layer 707, in particular, any of the followings is preferably used: CuPc, phthalocyanine tin(II) complex (SnPc), phthalocyanine zinc complex (ZnPc), cobalt(II) phthalocyanine, b-form (CoPc), phthalocyanine iron (FePc), and vanadyl 2,9,16,23-tetraphenoxy-29H,31H-phthalo cyanine (PhO-VOPc).

As the metal complex having a metal-oxygen bond and an aromatic ligand, which is contained in the electron-relay layer 707, a metal complex having a metal-oxygen double bond is preferably used. The metal-oxygen double bond has acceptor properties (properties of easily accepting electrons); thus, electrons can be transferred (donated and accepted) more easily. Further, the metal complex which has a metal-oxygen double bond is considered stable. Thus, the use of the metal complex having the metal-oxygen double bond makes it possible to drive the light-emitting element at low voltage more stably.

As a metal complex having a metal-oxygen bond and an aromatic ligand, a phthalocyanine-based material is preferable. Specifically, any of vanadyl phthalocyanine (VOPc), a phthalocyanine tin(IV) oxide complex (SnOPc), and a phthalocyanine titanium oxide complex (TiOPc) is preferable because a metal-oxygen double bond is more likely to act on another molecular in terms of a molecular structure and an acceptor property is high.

Note that as the phthalocyanine-based materials described above, a phthalocyanine-based material having a phenoxy group is preferable. Specifically, a phthalocyanine derivative having a phenoxy group, such as PhO-VOPc, is preferable. A phthalocyanine derivative having a phenoxy group is soluble in a solvent. A phthalocyanine derivative having a phenoxy group is soluble in a solvent. Thus, such a phthalocyanine derivative has an advantage of being easily handled during formation of the light-emitting element and an advantage of facilitating maintenance of an apparatus used for forming a film.

The electron-relay layer 707 may further contain a donor substance. Examples of the donor substance include an organic compound such as tetrathianaphthacene (abbreviation: TTN), nickelocene, and decamethylnickelocene, in addition to an alkali metal, an alkaline earth metal, a rare earth metal, and a compound of the above metals (e.g., an alkali metal compound (including an oxide such as lithium oxide, a halide, and a carbonate such as lithium carbonate or cesium carbonate), an alkaline earth metal compound (including an oxide, a halide, and a carbonate), and a rare earth metal compound (including an oxide, a halide, and a carbonate)). When such a donor substance is contained in the electron-relay layer 707, electrons can be transferred easily and the light-emitting element can be driven at lower voltage.

In the case where a donor substance is contained in the electron-relay layer 707, in addition to the materials described above as the substance having a high electron-transport property, a substance having a LUMO level higher than the acceptor level of the acceptor substance contained in the composite material layer 708 can be used. Specifically, it is preferable to use a substance having a LUMO level higher than or equal to −5.0 eV, preferably higher than or equal to −5.0 eV and lower than or equal to −3.0 eV. As examples of such a substance, a perylene derivative and a nitrogen-containing condensed aromatic compound can be given. Note that a nitrogen-containing condensed aromatic compound is preferably used for the electron-relay layer 707 because of its stability.

As specific examples of the perylene derivative, the following can be given: 3,4,9,10-perylenetetracarboxylicdianhydride (abbreviation: PTCDA), 3,4,9,10-perylenetetracarboxylic-bis-benzimidazole (abbreviation: PTCBI), N,N'-dioctyl-3,4,9,10-perylenetetracarboxylic diimide (abbreviation: PT CDI-C8H), N,N'-dihexyl-3,4,9,10-perylenetetracarboxylic diimide (Hex PTC), and the like.

As specific examples of the nitrogen-containing condensed aromatic compound, the following can be given: pirazino[2,3-f][1,10]phenanthroline-2,3-dicarbonitrile (PPDN), 2,3,6,7,10,11-hexacyano-1,4,5,8,9,12-hexaazatriphenylene (HAT (CN)$_6$), 2,3-diphenylpyrido[2,3-b]pyrazine (2PYPR), 2,3-bis(4-fluorophenyl)pyrido[2,3-b]pyrazine (F2PYPR), and the like.

Besides, 7,7,8,8-tetracyanoquinodimethane (abbreviation: TCNQ), 1,4,5,8-naphthalenetetracarboxylicdianhydride (abbreviation: NTCDA), perfluoropentacene, copper hexadecafluorophthalocyanine (abbreviation: F$_{16}$CuPc), N,N'-bis(2,2,3,3,4,4,5,5,6,6,7,7,8,8,8-pentadecafluorooctyl)-1,4,5,8-naphthalenetetracar boxylic diimide (abbreviation: NTCD1-C8F), 3',4'-dibutyl-5,5"-bis(dicyanomethylene)-5,5"-dihydro-2,2':5',2"-terthiophene) (abbreviation: DCMT), methanofullerenes (e.g., [6,6]-phenyl C$_{61}$ butyric acid methyl ester), or the like can be used.

Note that in the case where a donor substance is contained in the electron-relay layer 707, the electron-relay layer 707 may be formed by a method such as co-evaporation of the substance having a high electron-transport property and the donor substance.

The hole-injection layer 701, the hole-transport layer 702, the light-emitting layer 703, and the electron-transport layer 704 may be each formed using any of the above-described materials. In particular, the hole-injection layer 701 can be formed using the composite material of one embodiment of the present invention. Further, the organic compound used for the composite material of one embodiment of the present invention can be suitably used for each of the hole-transport layer 702 and the light-emitting layer 703.

Note that this embodiment can be freely combined with any of the other embodiments as appropriate.

Embodiment 3

In this embodiment, a light-emitting device including a light-emitting element of one embodiment of the present invention will be described with reference to FIGS. 3A and 3B. FIG. 3A is a top view illustrating a light-emitting device. FIG. 3B is a cross-sectional view taken along lines A-B and C-D in FIG. 3A.

The light-emitting device of this embodiment includes a source side driver circuit 401 and a gate side driver circuit 403 which are driver circuit portions, a pixel portion 402, a sealing substrate 404, a sealant 405, a flexible printed circuit (FPC) 409, and an element substrate 410. A portion enclosed by the sealant 405 is a space.

Note that a lead wiring 408 is a wiring for transmitting signals that are to be inputted to the source driver circuit 401 and the gate driver circuit 403, and receives a video signal, a clock signal, a start signal, a reset signal, and the like from an FPC 409 which serves as an external input terminal. Although only the FPC is illustrated here, a printed wiring board (PWB) may be attached to the FPC. The light-emitting device in this specification includes, in its category, not only the light-emitting device itself but also the light-emitting device provided with the FPC or the PWB.

The driver circuit portion and the pixel portion are formed over the element substrate 410 illustrated in FIG. 3A. In FIG. 3B, the source side driver circuit 401 which is the driver circuit portion and one pixel in the pixel portion 402 are illustrated.

Note that as the source side driver circuit 401, a CMOS circuit which is obtained by combining an n-channel TFT 423 and a p-channel TFT 424 is formed. The driver circuit may be any of a variety of circuits formed with TFTs, such as a CMOS circuit, a PMOS circuit, or an NMOS circuit. Although a driver-integrated type where the driver circuit is formed over the substrate is described in this embodiment, the present invention is not limited to this, and the driver circuit may be formed outside the substrate, not over the substrate.

The pixel portion 402 includes a plurality of pixels having a switching TFT 411, a current control TFT 412, and a first electrode 413 electrically connected to a drain of the current control TFT 412. An insulator 414 is formed to cover an end portion of the first electrode 413. Here, the insulator 414 is formed using a positive type photosensitive acrylic resin film.

In order to improve the coverage, the insulator 414 is provided such that either an upper end portion or a lower end portion of the insulator 414 has a curved surface with a curvature. For example, when positive photosensitive acrylic is used as a material for the insulator 414, it is preferable that only an upper end portion of the insulator 414 have a curved surface with a radius of curvature (0.2 μm to 3 μm). For the insulator 414, it is also possible to use either a negative type photosensitive material that becomes insoluble in an etchant by light irradiation or a positive type photosensitive material that becomes soluble in an etchant by light irradiation.

An EL layer 416 and a second electrode 417 are formed over the first electrode 413. Here, as a material for forming the first electrode 413 functioning as the anode, it is preferable to use a material having a high work function. For example, it is possible to use a single layer of an ITO film, an indium tin oxide film that includes silicon, an indium oxide film that includes 2 wt % to 20 wt % of zinc oxide, a titanium nitride film, a chromium film, a tungsten film, a Zn film, a Pt film, or the like, a stacked layer of a titanium nitride film and a film that mainly includes aluminum, a three-layer structure of a titanium nitride film, a film that mainly includes aluminum and a titanium nitride film, or the like. Note that when a stacked structure is employed, the resistance of a wiring is low and a favorable ohmic contact is obtained.

The EL layer 416 is formed by any of a variety of methods such as an evaporation method using an evaporation mask, a droplet discharging method like an ink jet method, a printing method, and a spin coating method. The EL layer 416 includes the composite material of one embodiment of the present invention which is described in Embodiment 1. Further, another material included in the EL layer 416 may be a low molecular material, an oligomer, a dendrimer, a high molecular material, or the like.

As a material used for the second electrode 417 which is formed over the EL layer 416 and serves as a cathode, it is preferable to use a material having a low work function (e.g., Al, Mg, Li, Ca, or an alloy or compound thereof such as MgAg, Mg—In, or Al—Li). In order that light generated in the EL layer 416 be transmitted through the second electrode 417, a stack of a metal thin film having a reduced thickness and a transparent conductive film (e.g., ITO, indium oxide containing 2 wt % to 20 wt % of zinc oxide, indium oxide-tin oxide that includes silicon or silicon oxide, or zinc oxide) is preferably used for the second electrode 417.

The sealing substrate 404 is attached to the element substrate 410 with the sealant 405; thus, a light-emitting element 418 is provided in the space 407 enclosed by the element substrate 410, the sealing substrate 404, and the sealant 405. Note that the space 407 is filled with a filler and may be filled with an inert gas (such as nitrogen or argon) or the sealant 405.

Note that as the sealant 405, an epoxy-based resin is preferably used. Such a material preferably allows as little moisture and oxygen as possible to penetrate. As a material for the sealing substrate 404, a glass substrate, a quartz substrate, or a plastic substrate including fiberglass-reinforced plastics (FRP), polyvinyl fluoride (PVF), polyester, acrylic, or the like can be used.

As described above, the active matrix light-emitting device having the light-emitting element of one embodiment of the present invention can be obtained.

Figure 4A:
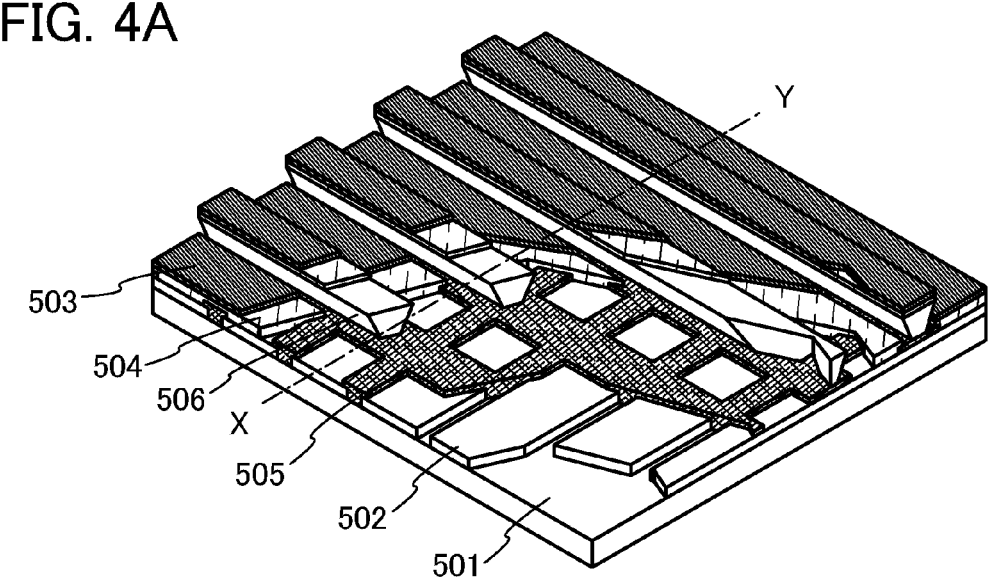
FIGS. 4A and 4B illustrate a light-emitting device of one embodiment of the present invention.
Figure 4B:
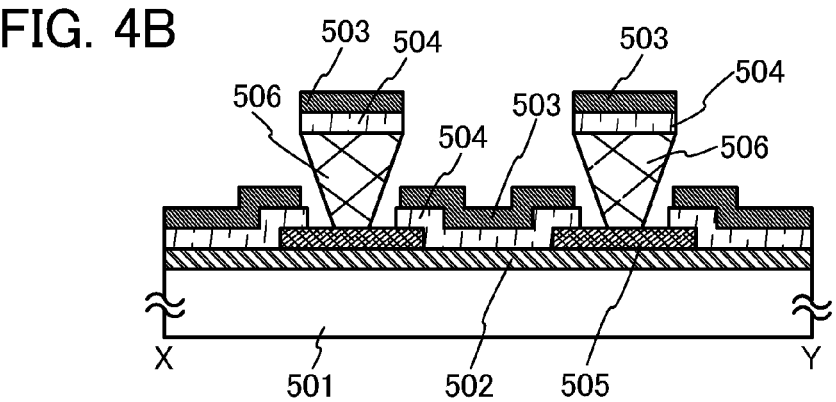

Further, the light-emitting element of the present invention can be used for a passive matrix light-emitting device instead of the above active matrix light-emitting device. FIGS. 4A and 4B are a perspective view and a cross-sectional view of a passive matrix light-emitting device using the light-emitting element of the present invention. FIG. 4A is a perspective view of the light-emitting device, and FIG. 4B is a cross-sectional view taken along line X-Y in FIG. 4A.

In FIGS. 4A and 4B, an EL layer 504 is provided between a first electrode 502 and a second electrode 503 over a substrate 501. An end portion of the first electrode 502 is covered with an insulating layer 505. In addition, a partition layer 506 is provided over the insulating layer 505. The sidewalls of the partition layer 506 slope so that the distance between one sidewall and the other sidewall gradually decreases toward the surface of the substrate. In other words, a cross section taken along the direction of the short side of the partition layer 506 is trapezoidal, and the lower side (a side in contact with the insulating layer 505 which is one of a pair of parallel sides of the trapezoidal cross section) is shorter than the upper side (a side not in contact with the insulating layer 505 which is the other of the pair of parallel sides). With the partition layer 506 provided in such a way, a defect of a light-emitting element due to crosstalk or the like can be prevented.

In the above manner, the passive matrix light-emitting device including the light-emitting element of one embodiment of the present invention can be obtained.

FIGS. 5A to 5C illustrate examples of light-emitting devices to which one embodiment of the present invention is applied. FIG. 5A is a top view illustrating the light-emitting devices. FIGS. 5B and 5C are cross-sectional views taken along line E-F in FIG. 5A.

Light-emitting devices 900 illustrated in FIGS. 5A to 5C each include a light-emitting element 908 (a first electrode 101, an EL layer 102, and a second electrode 108) over a first substrate 901. The light-emitting element 908 can be formed using any of the materials described in Embodiment 2. The EL layer 102 includes the composite material of one embodiment of the present invention.

To the light-emitting devices of this embodiment, any of the following structures can be applied: a structure in which a light-emitting element emits light upward (such a structure is also referred to as a top emission structure); a structure in which a light-emitting element emits light upward and downward (such a structure is also referred to as a dual emission structure); and a structure in which a light-emitting element emits light downward (such a structure is also referred to as a bottom emission structure).

A light-emitting device having a bottom emission structure is illustrated in FIG. 5B.

The light-emitting device illustrated in FIG. 5B includes the first electrode 101 over the first substrate 901, the EL layer 102 over the first electrode 101, and the second electrode 108 over the EL layer 102.

A first terminal 903 is electrically connected to an auxiliary wiring 910 and the first electrode 101, and a second terminal 904 is electrically connected to the second electrode 108. Further, an insulating layer 909 is formed between end portions of the first electrode 101 and the second electrode 108 and between the auxiliary wiring 910 and the EL layer 102. Note that although a structure in which the first electrode 101 is formed over the auxiliary wiring 910 is illustrated in FIG. 5B, a structure in which the auxiliary wiring 910 is formed over the first electrode 101 may be employed.

In addition, the first substrate 901 and the second substrate 902 are bonded together by a sealant 912. Further, a desiccant 911 may be included between the first substrate 901 and the second substrate 902.

Further, the upper and/or lower portions of the first substrate 901 may be provided with a light extraction structure. As the light extraction structure, an uneven structure can be provided at an interface through which light is transmitted from the side having a high refractive index to the side having a low refractive index. A specific example is as follows: as illustrated in FIG. 5B, a light extraction structure 913a with minute unevenness is provided between the light-emitting element 908 having a high refractive index and the first substrate 901 having a lower refractive index, and a light extraction structure 913b with unevenness is provided between the first substrate 901 and the air.

However, in the light-emitting element, unevenness of the first electrode 101 might cause leakage current in the EL layer 102 formed over the first electrode 101. Therefore, in this embodiment, a planarization layer 914 having a refractive index higher than or equal to that of the EL layer 102 is provided in contact with the light extraction structure 913a. Accordingly, the first electrode 101 can be a flat film, and generation of leakage current in the EL layer due to the unevenness of the first electrode 101 can be suppressed. Further, because of the light extraction structure 913a at an interface between the planarization layer 914 and the first substrate 901, light which cannot be extracted to the air due to total reflection can be reduced, so that the light extraction efficiency of the light-emitting device can be increased.

The present invention is not limited to the structure in which the first substrate 901, the light extraction structure 913a, and the light extraction structure 913b are different components as in FIG. 5B. Two or all of these may be formed as one component. The light extraction structure 913*a* may be all formed inside a sealing region.

A light-emitting device having a top emission structure is illustrated in FIG. 5C.

The light-emitting device illustrated in FIG. 5C includes the second electrode 108 over the first substrate 901, the EL layer 102 over the second electrode 108, and the first electrode 101 over the EL layer 102.

The first terminal 903 is electrically connected to the second electrode 108, and the second terminal 904 is electrically connected to the first electrode 101. Further, the insulating layer 909 is formed between end portions of the first electrode 101 and the second electrode 108.

In addition, the first substrate 901 and the second substrate 902 are bonded together by a sealant 912. An auxiliary wiring may be formed over the first electrode 101. Further, a desiccant 911 may be included between the first substrate 901 and the second substrate 902. The desiccant 911 is preferably provided at a position that does not overlap a light-emitting region of a light-emitting element. Alternatively, a desiccant that transmits light from the light-emitting element is preferably used.

Although the light-emitting device 900 illustrated in FIG. 5A is octagonal, the present invention is not limited to this shape. The light-emitting device 900 and the light-emitting element 908 may have other polygonal shapes or a shape having a curve. As the shape of the light-emitting device 900, a triangle, a quadrangle, a hexagon, or the like is particularly preferable. This is because such a shape allows a plurality of light-emitting devices 900 to be provided in a limited area without a space therebetween, and also because such a shape enables effective use of the limited substrate area for formation of the light-emitting device 900. Further, the number of elements formed over the substrate is not limited to one and a plurality of elements may be provided.

As materials of the first substrate 901 and the second substrate 902, a material having a light-transmitting property, such as glass, quartz, or an organic resin can be used. At least one of the first substrate 901 and the second substrate 902 transmits light emitted from the light-emitting element.

In the case where an organic resin is used for the substrates, for example, any of the following can be used as the organic resin: polyester resins such as polyethylene terephthalate (PET) and polyethylene naphthalate (PEN), a polyacrylonitrile resin, a polyimide resin, a polymethylmethacrylate resin, a polycarbonate (PC) resin, a polyethersulfone (PES) resin, a polyamide resin, a cycloolefin resin, a polystyrene resin, a polyamide imide resin, a polyvinylchloride resin, and the like. Further, a substrate in which a glass fiber is impregnated with an organic resin or a substrate in which an inorganic filler is mixed with an organic resin can also be used.

Note that the light-emitting devices described in this embodiment are formed using a light-emitting element of one embodiment of the present invention; thus, the light-emitting devices have low power consumption.

Note that this embodiment can be freely combined with any of the other embodiments as appropriate.

Embodiment 4

In this embodiment, examples of a variety of electronic devices and lighting devices that are completed by using the light-emitting device of one embodiment of the present invention will be described with reference to FIGS. 6A to 6E and FIG. 7.

Examples of the electronic devices to which the light-emitting device is applied are television devices (also referred to as TV or television receivers), monitors for computers and the like, cameras such as digital cameras and digital video cameras, digital photo frames, cellular phones (also referred to as portable telephone devices), portable game machines, portable information terminals, audio playback devices, large game machines such as pin-ball machines, and the like. Specific examples of these electronic devices and lighting devices are illustrated in FIGS. 6A to 6E.

Figure 6A:
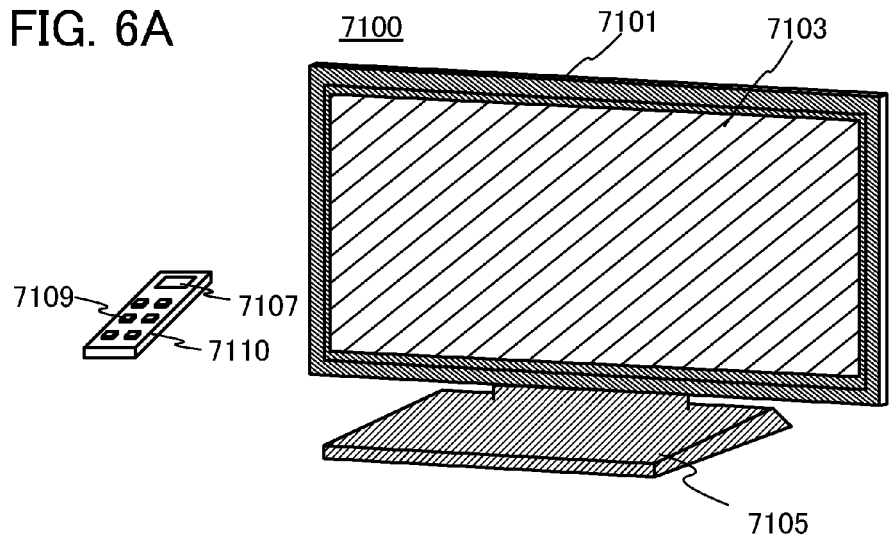
FIGS. 6A to 6E each illustrate an electronic device of one embodiment of the present invention.

FIG. 6A illustrates an example of a television device. In the television device 7100, a display portion 7103 is incorporated in a housing 7101. Images can be displayed on the display portion 7103, and the light-emitting device can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the receiver, a general television broadcast can be received. Furthermore, when the television device 7100 is connected to a communication network by wired or wireless connection via the modem, one-way (from a transmitter to a receiver) or two-way (between a transmitter and a receiver, between receivers, or the like) data communication can be performed.

Figure 6B:
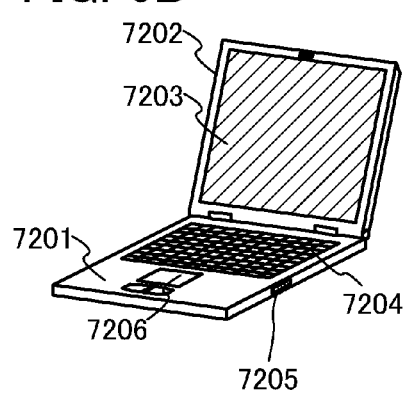

FIG. 6B illustrates a computer, which includes a main body 7201, a housing 7202, a display portion 7203, a keyboard 7204, an external connection port 7205, a pointing device 7206, and the like. This computer is manufactured by using a light-emitting device for the display portion 7203.

Figure 6C:
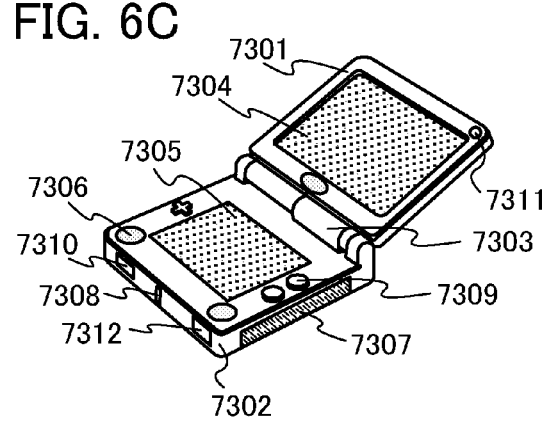

FIG. 6C illustrates a portable game machine having two housings, a housing 7301 and a housing 7302, which are connected with a joint portion 7303 so that the portable game machine can be opened or folded. A display portion 7304 is incorporated in the housing 7301 and a display portion 7305 is incorporated in the housing 7302. In addition, the portable game machine illustrated in FIG. 6C includes a speaker portion 7306, a recording medium insertion portion 7307, an LED lamp 7308, an input unit (an operation key 7309, a connection terminal 7310, a sensor 7311 (sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 7312), and the like. It is needless to say that the structure of the portable game machine is not limited to the above as long as a light-emitting device is used for at least either the display portion 7304 or the display portion 7305, or both, and may include other accessories as appropriate. The portable amusement machine illustrated in FIG. 6C has a function of reading a program or data stored in a recording medium to display it in the display portion, and a function of sharing information with another portable amusement machine by wireless communication. Note that the functions of the portable amusement machine illustrated in FIG. 6C are not limited to these functions, and the portable amusement machine can have various functions.

Figure 6D:
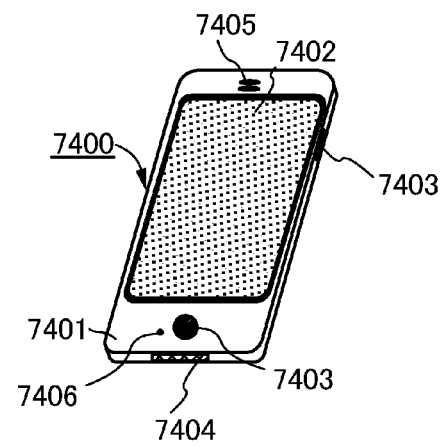

FIG. 6D illustrates an example of a mobile phone. The mobile phone 7400 is provided with a display portion 7402 incorporated in a housing 7401, operation buttons 7403, an external connection port 7404, a speaker 7405, a microphone 7406, and the like. Note that the mobile phone 7400 is manufactured using a light-emitting device for the display portion 7402.

When the display portion 7402 of the cellular phone 7400 illustrated in FIG. 6D is touched with a finger or the like, data can be input into the cellular phone 7400. Further, operations such as making a call and composing e-mail can be performed by touch on the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or composing an e-mail, a text input mode mainly for inputting text is selected for the display portion 7402 so that text displayed on a screen can be inputted. In this case, it is preferable to display a keyboard or number buttons on almost the entire screen of the display portion 7402.

When a detection device including a sensor for detecting inclination, such as a gyroscope or an acceleration sensor, is provided inside the cellular phone 7400, display on the screen of the display portion 7402 can be automatically changed by determining the orientation of the cellular phone 7400 (whether the mobile phone is placed horizontally or vertically for a landscape mode or a portrait mode).

The screen modes are switched by touching the display portion 7402 or operating the operation buttons 7403 of the housing 7401. Alternatively, the screen modes can be switched depending on kinds of images displayed on the display portion 7402. For example, when a signal for an image displayed on the display portion is a signal of moving image data, the screen mode is switched to the display mode. When the signal is a signal for text data, the screen mode is switched to the input mode.

Moreover, in the input mode, when input by touching the display portion 7402 is not performed within a specified period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken by touch on the display portion 7402 with the palm or the finger, whereby personal authentication can be performed. Further, by providing a backlight or a sensing light source which emits a near-infrared light in the display portion, an image of a finger vein, a palm vein, or the like can be taken.

Figure 6E:
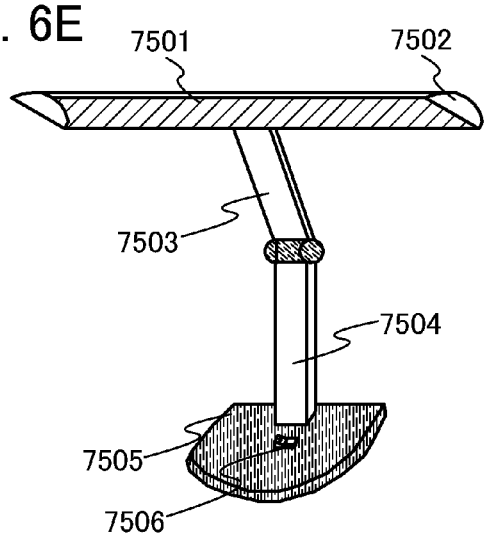

FIG. 6E illustrates a desk lamp including a lighting portion 7501, a shade 7502, an adjustable arm 7503, a support 7504, a base 7505, and a power supply 7506. The desk lamp is manufactured using a light-emitting device for the lighting portion 7501. Note that a lamp includes a ceiling light, a wall light, and the like in its category.

Figure 7:
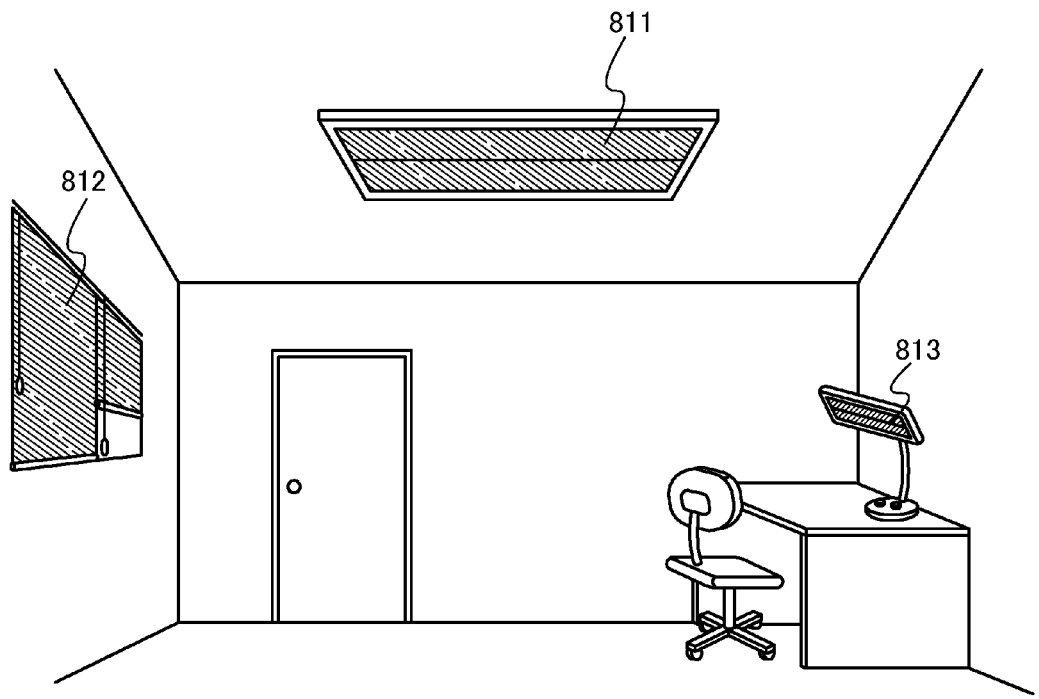
FIG. 7 illustrates lighting devices of one embodiment of the present invention.

FIG. 7 illustrates an example in which a light-emitting device is used for an interior lighting device 811. The light-emitting device can have a larger area, and thus can be used as a lighting device having a large area. Furthermore, the light-emitting device can be used as a roll-type lighting device 812. As illustrated in FIG. 7, a desk lamp 813 described with reference to FIG. 6E may also be used in a room provided with the interior lighting device 811.

In the above-described manner, electronic devices and lighting devices can be obtained by application of the light-emitting device. The light-emitting device has a remarkably wide application range, and can be applied to electronic devices in a variety of fields.

Note that the structure described in this embodiment can be combined with any of the structures described in the above embodiments as appropriate.

Example 1

In this example, specific examples of the composite material of one embodiment of the present invention will be described. The composite material of one embodiment of the present invention includes an organic compound and an inorganic compound exhibiting an electron-accepting property with respect to the organic compound. The rings of the organic compound are all benzene rings. The number of the benzene rings is greater than or equal to 4 and less than or equal to 25.

Table 1 shows organic compounds used in Structural Examples 1 to 3 and the HOMO levels (eV) of the organic compounds. Note that the HOMO levels are measured by photoelectron spectroscopy. In addition, the structural formulae of the organic compounds are shown below.

TABLE 1

|  | Organic compound | HOMO level (eV) |
| --- | --- | --- |
| Structural Example 1 | mBP3P | −6.1 |
| Structural Example 2 | 6P | −5.9 |
| Structural Example 3 | SPSi | −5.8 |

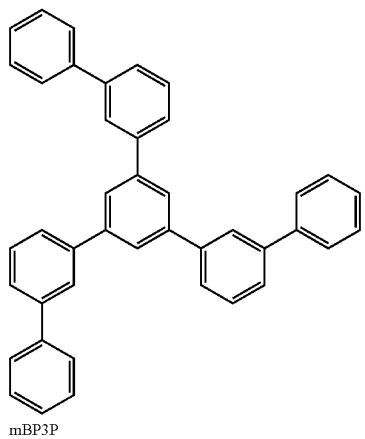

mBP3P

TABLE 1-continued

| Organic compound | HOMO level (eV) |
|---|---|
| 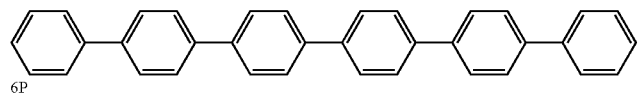 6P | |
| 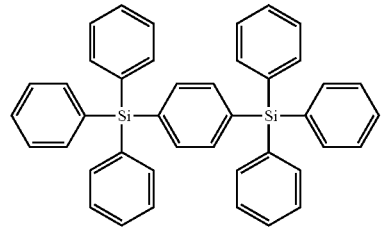 [SMILES: c1ccc([Si](c2ccccc2)(c2ccccc2)c2ccc([Si](c3ccccc3)(c3ccccc3)c3ccccc3)cc2)cc1] SiPSi | |

Figure 8A:
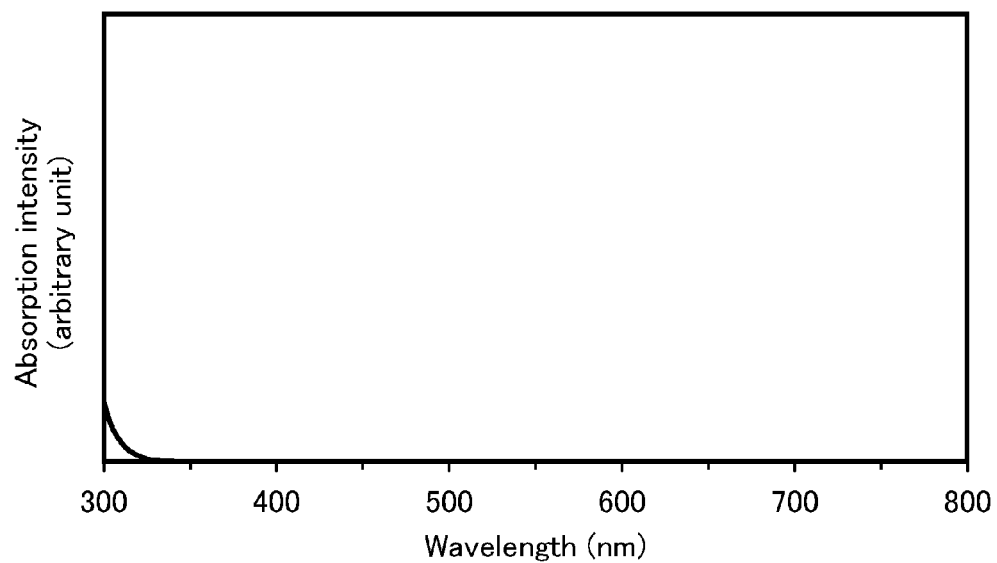
FIGS. 8A and 8B show an absorption spectrum and an emission spectrum of mBP3P in a toluene solution of mBP3P.
Figure 8B:
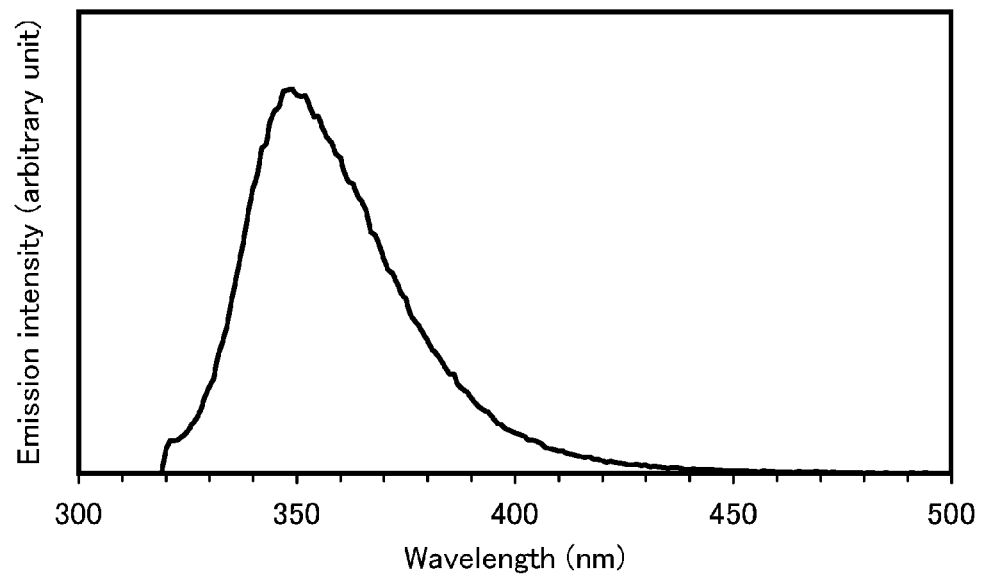

FIG. 8A shows an absorption spectrum of 1,3,5-tri(biphenyl-3-yl)benzene (abbreviation: mBP3P) in a toluene solution of mBP3P, and FIG. 8B shows an emission spectrum thereof. The absorption spectrum was measured with an ultraviolet-visible spectrophotometer (V-550, manufactured by JASCO Corporation). The measurements were performed in such a manner that the solution was put in a quartz cell. Shown here is the absorption spectrum which was obtained by subtracting the absorption spectra of quartz and toluene from those of quartz and the solution. In FIG. 8A, the horizontal axis represents wavelength (nm) and the vertical axis represents absorption intensity (arbitrary unit). In FIG. 8B, the horizontal axis represents wavelength (nm) and the vertical axis represents emission intensity (arbitrary unit). The emission wavelength peak of mBP3P is 349 nm (excitation wavelength: 290 nm).

FIG. 8A shows that almost no absorption in the visible light region is observed in the absorption spectrum of mBP3P in the toluene solution of mBP3P. According to FIG. 8B, the emission peak is located on the short wavelength side; thus, mBP3P is suitable as a material for a hole-transport layer in contact with a light-emitting layer or as a host material for a light-emitting layer.

Although described later, almost no absorption in the visible light region is observed also in absorption spectra of thin films of mBP3P (see FIGS. 9A and 9B). The fact that both the solution and the thin film exhibit almost no absorption in the visible light region indicates that the organic compound is suitable for both a film of a single organic compound and for a film of a mixture with another organic compound. Thus, the organic compound can be suitably used for each of the composite material of one embodiment of the present invention, a hole-transport layer, and a light-emitting layer.

In each of Structural Examples 1 to 3, molybdenum oxide was used as an inorganic compound.

A method of forming the composite material of one embodiment of the present invention is described.

Structural Example 1

First, a glass substrate was fixed on a substrate holder in a vacuum evaporation apparatus. Then, mBP3P and molybdenum(VI) oxide were separately put in different resistance-heating evaporation sources, and films each containing mBP3P and molybdenum oxide were formed by a co-evaporation method at a pressure reduced to approximately $10^{-4}$ Pa. At this time, mBP3P and molybdenum oxide were co-evaporated such that the mass ratios of mBP3P to molybdenum oxide were 4:2, 4:1, and 4:0.5 (=mBP3P: molybdenum oxide). The thickness of each film was set to 50 nm.

Figure 9A:
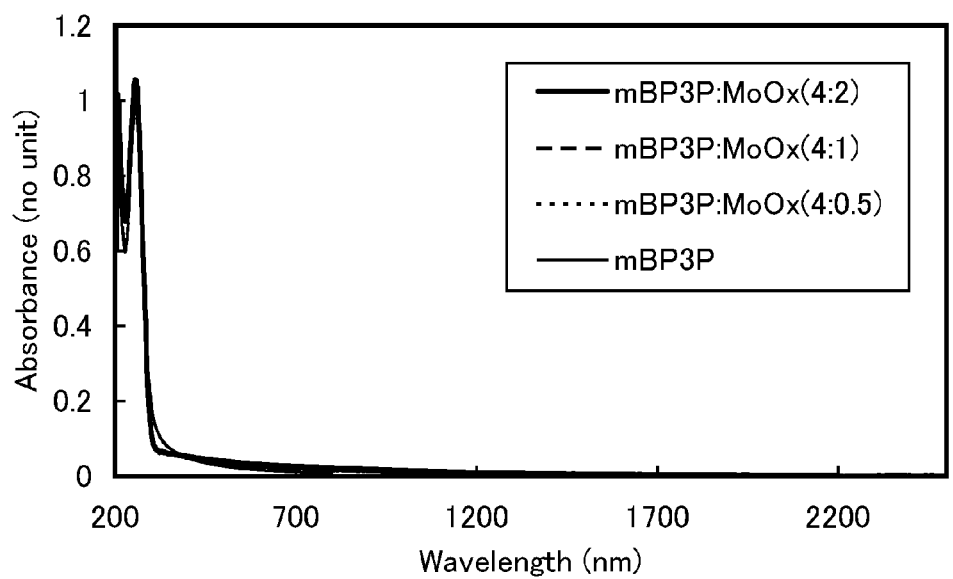
FIGS. 9A and 9B show absorbances of mBP3P and composite materials thereof according to Example 1.
Figure 9B:
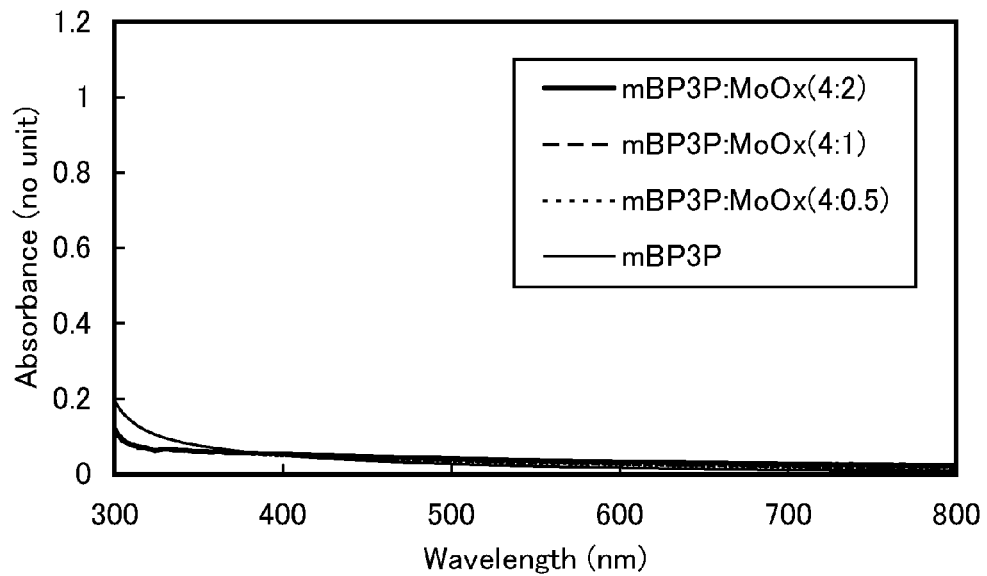

FIGS. 9A and 9B show measurement results of absorption spectra of the thus formed composite films of mBP3P and molybdenum oxide (Structural Example 1). In addition, for comparison, an absorption spectrum of a film of only mBP3P (50 nm thick) is also shown in the graphs.

Structural Example 2

First, a glass substrate was fixed on a substrate holder in a vacuum evaporation apparatus. Then, p-sexiphenyl (abbreviation: 6P) and molybdenum(VI) oxide were separately put in different resistance-heating evaporation sources, and films each containing 6P and molybdenum oxide were formed by a co-evaporation method at a pressure reduced to approximately $10^{-4}$ Pa. At this time, 6P and molybdenum oxide were co-evaporated such that the mass ratios of 6P to molybdenum oxide were 4:2, 4:1, and 4:0.5 (=6P: molybdenum oxide). The thickness of each film was set to 50 nm.

Figure 10A:
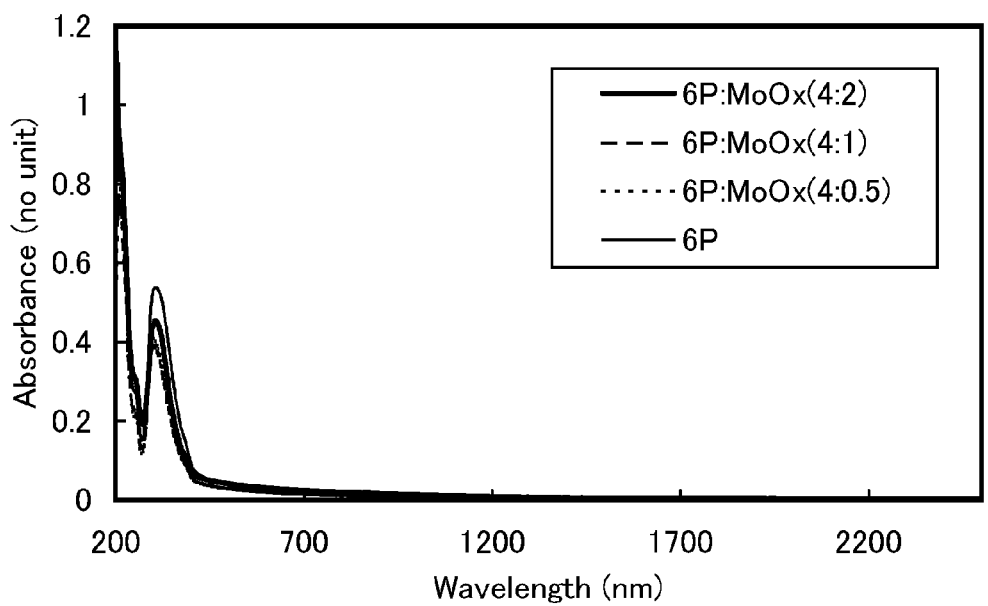
FIGS. 10A and 10B show absorbances of 6P and composite materials thereof according to Example 1.
Figure 10B:
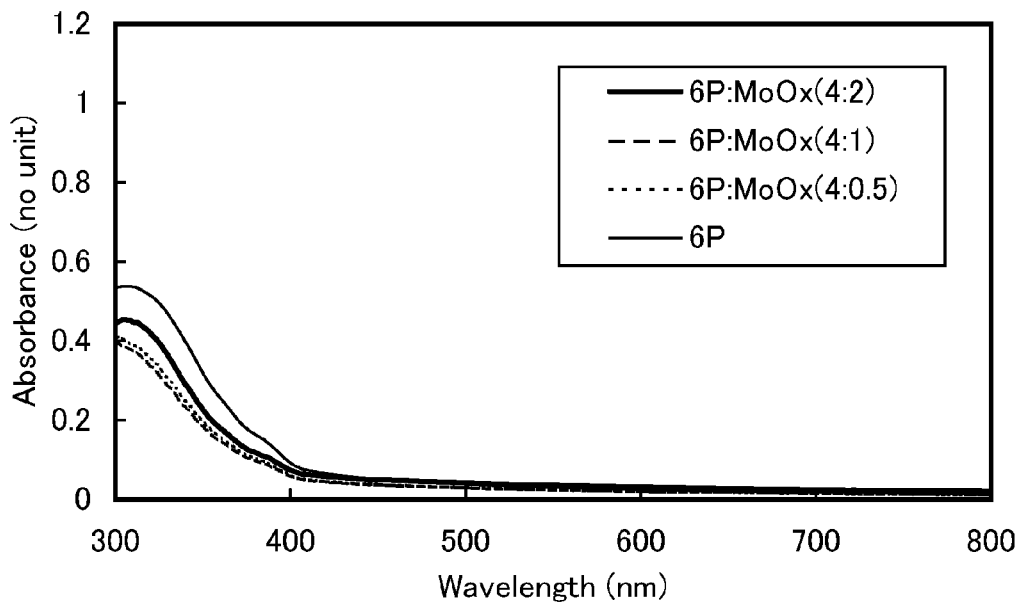

FIGS. 10A and 10B show results of measurement of absorption spectra of the thus formed composite films of 6P and molybdenum oxide (Structural Example 2). In addition, for comparison, an absorption spectrum of a film of only 6P (50 nm thick) is also shown in the graphs.

Structural Example 3

First, a glass substrate was fixed on a substrate holder in a vacuum evaporation apparatus. Then, 1,4-bis(triphenylsilyl)benzene (abbreviation: SiPSi) and molybdenum(VI) oxide were separately put in different resistance-heating evaporation sources, and films each containing SiPSi and molybdenum oxide was formed by a co-evaporation method at a pressure reduced to approximately $10^{-4}$ Pa. At this time, SiPSi and molybdenum oxide were co-evaporated such that the mass ratios of SiPSi to molybdenum oxide were 4:2, 4:1, and 4:0.5 (=SiPSi: molybdenum oxide). The thickness of each film was set to 50 nm.

Figure 11A:
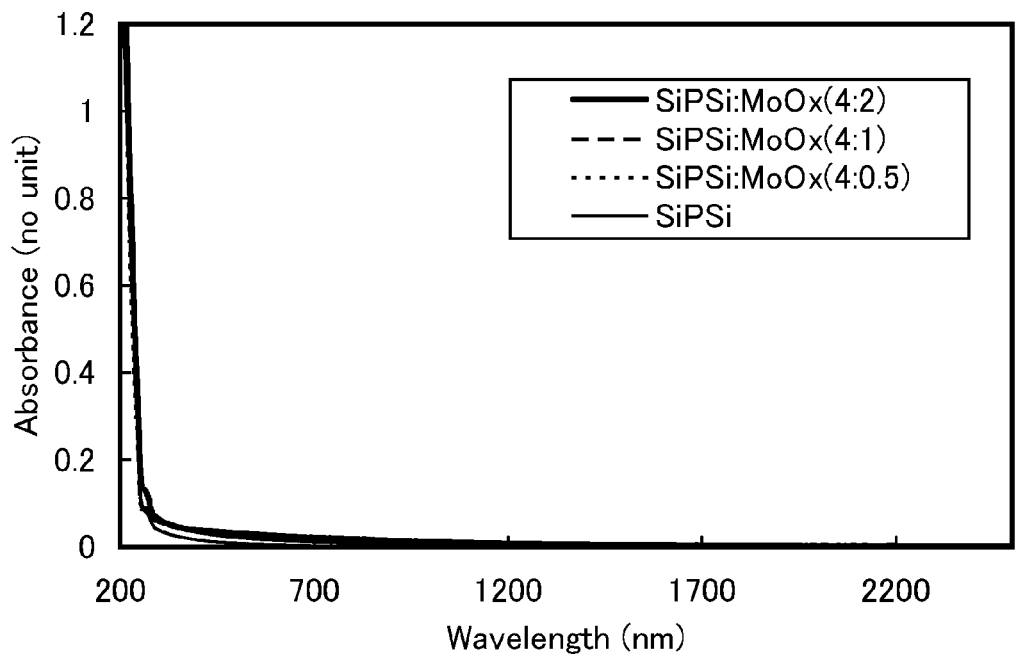
FIGS. 11A and 11B show absorbances of SiPSi and composite materials thereof according to Example 1.
Figure 11B:
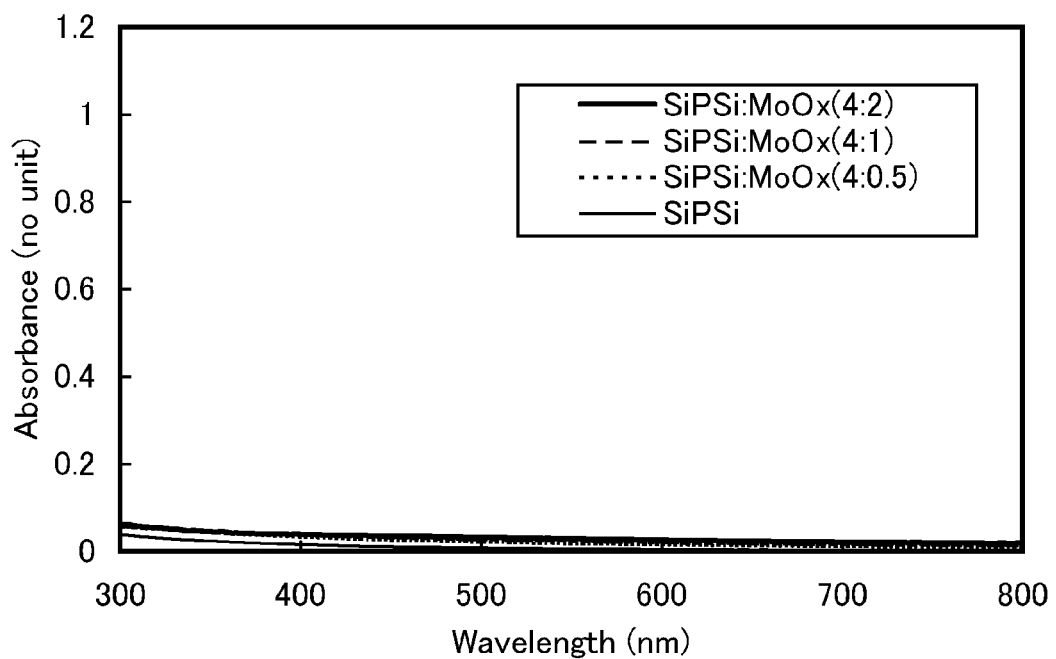

FIGS. 11A and 11B show measurement results of absorption spectra of the thus formed composite films of SiPSi and molybdenum oxide (Structural Example 3). In addition, for comparison, an absorption spectrum of a film of only SiPSi (50 nm thick) is also shown in the graphs.

In each of FIGS. 9A, 9B, 10A, 10B, 11A, and 11B, the horizontal axis represents wavelength (nm) and the vertical axis represents absorbance (no unit).

The results show that each of the composite materials of embodiments of the present invention is a material that has almost no significant absorption peak in the visible light region and has a high light-transmitting property. Further, the composite materials of embodiments of the present invention exhibit almost no significant absorption peak also in the infrared region (the wavelength region of 700 nm or more).

The absorption spectra of the composite materials each including the organic compound and molybdenum oxide, which is one embodiment of the present invention, have substantially the same shape as the absorption spectrum of the organic compound. Almost no significant absorption peak in the visible to infrared region is observed even in the case of films having a high concentration of molybdenum oxide (specifically, the film having a mass ratio of the organic compound to molybdenum oxide of 4:2 in each Structural Example). This indicates that in the composite materials of embodiments of the present invention, light absorption due to charge transfer interaction is unlikely to occur.

Example 2

Figure 18A:
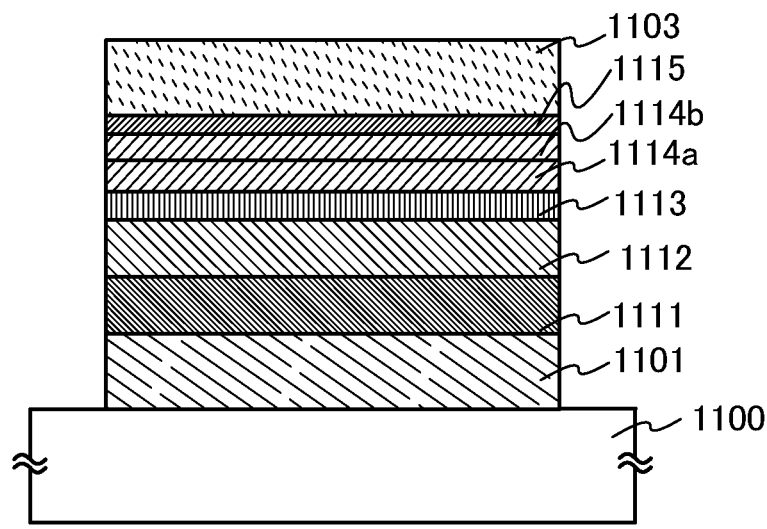
FIGS. 18A and 18B each illustrate a light emitting element in Examples.

In this example, a light-emitting element of one embodiment of the present invention will be described with reference to FIG. 18A. Shown below are structural formulae of materials used in this example. Note that the structural formulae of the materials used in the above example are omitted here.

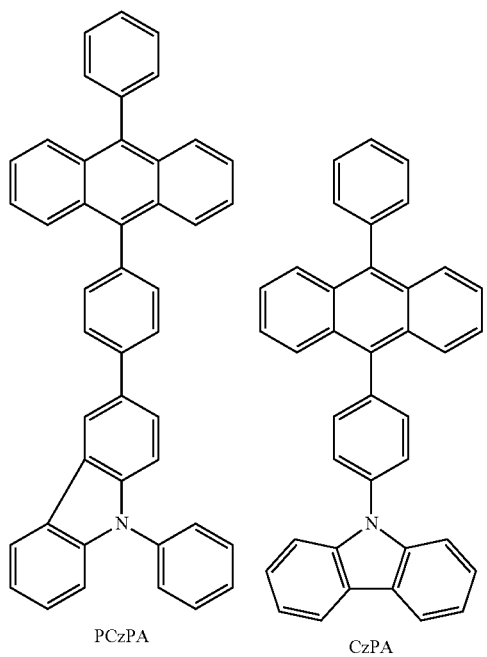

PCzPA   CzPA

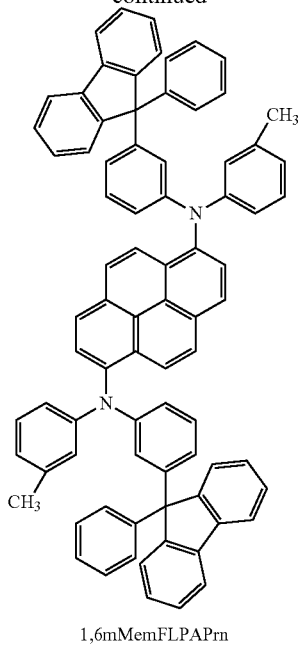

1,6mMemFLPAPrn

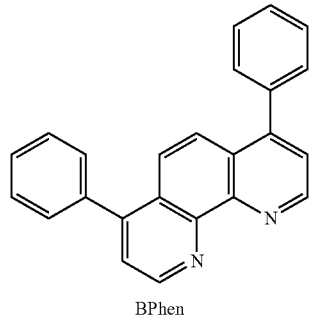

BPhen

A method of manufacturing a light-emitting element 1 of this example will be described below.

(Light-Emitting Element 1)

First, a film of indium tin oxide containing silicon oxide (ITSO) was formed over a glass substrate 1100 by a sputtering method to form a first electrode 1101 serving as an anode. The thickness of the first electrode 1101 was set to 110 nm, and the area thereof was set to 2 mm×2 mm.

In pretreatment for forming the light-emitting element on the substrate 1100, UV ozone treatment was performed for 370 seconds after washing of a surface of the substrate with water and baking performed at 200° C. for one hour.

After that, the substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed on a substrate holder in the vacuum evaporation apparatus so that a surface on which the first electrode 1101 was provided faced downward. The pressure in the vacuum evaporation apparatus was reduced to about $10^{-4}$ Pa. Then, mBP3P and molybdenum(VI) oxide were co-evaporated to form a hole-injection layer 1111 on the first electrode

1101. The thickness of the hole-injection layer 1111 was set to 50 nm. The mass ratio of mBP3P to molybdenum oxide was adjusted to 4:2 (=mBP3P: molybdenum oxide). Note that the co-evaporation method refers to an evaporation method in which evaporation is carried out from a plurality of evaporation sources at the same time in one treatment chamber.

Next, on the hole-injection layer 1111, a film of 9-phenyl-3-[4-(10-phenyl-9-anthryl)phenyl]-9H-carbazole (abbreviation: PCzPA) was formed to a thickness of 10 nm to form a hole-transport layer 1112.

Further, on the hole-transport layer 1112, 9-[4-(N-carbazolyl)]phenyl-10-phenylanthracene (abbreviation: CzPA) and N,N'-bis(3-methylphenyl)-N,N-bis[3-(9-phenyl-9H-fluoren-9-yl)phenyl]-pyrene-1,6-dia mine (abbreviation: 1.6 mMemFLPAPrn) were co-evaporated to form a light-emitting layer 1113. Here, the mass ratio of CzPA to 1.6 mMemFLPAPrn was adjusted to 1:0.04 (=CzPA: 1.6 mMemFLPAPrn). The thickness of the light-emitting layer 1113 was set to 30 nm.

Further, on the light-emitting layer 1113, a film of CzPA was formed to a thickness of 10 nm to form a first electron-transport layer 1114a.

Then, on the first electron-transport layer 1114a, a film of bathophenanthroline (abbreviation: BPhen) was formed to a thickness of 20 nm to form a second electron-transport layer 1114b.

Further, on the second electron-transport layer 1114b, a film of lithium fluoride (LiF) was formed to a thickness of 1 nm by evaporation to form an electron-injection layer 1115.

Lastly, a film of aluminum was formed to a thickness of 200 nm by evaporation to form a second electrode 1103 serving as a cathode. Through the above steps, the light-emitting element 1 of this example was manufactured.

Note that in all the above evaporation steps, evaporation was performed by a resistance-heating method.

Table 2 shows the element structure of the light-emitting element 1 obtained as described above.

TABLE 2

| | First electrode | Hole-injection layer | Hole-transport layer | Light-emitting layer | First electron-transport layer | Second electron-transport layer | Electron-injection layer | Second electrode |
|---|---|---|---|---|---|---|---|---|
| Light-emitting element 1 | ITSO 110 nm | mBP3P:MoOx (=4:2) 50 nm | PCzPA 10 nm | CzPA: 1,6mMemFLPAPrn (=1:0.04) 30 nm | CzPA 10 nm | BPhen 20 nm | LiF 1 nm | Al 200 nm |

In a glove box containing a nitrogen atmosphere, the light-emitting element 1 was sealed so as not to be exposed to the air. Then, operation characteristics of the light-emitting element 1 were measured. Note that the measurement was carried out at room temperature (in an atmosphere kept at 25° C.).

Figure 12:
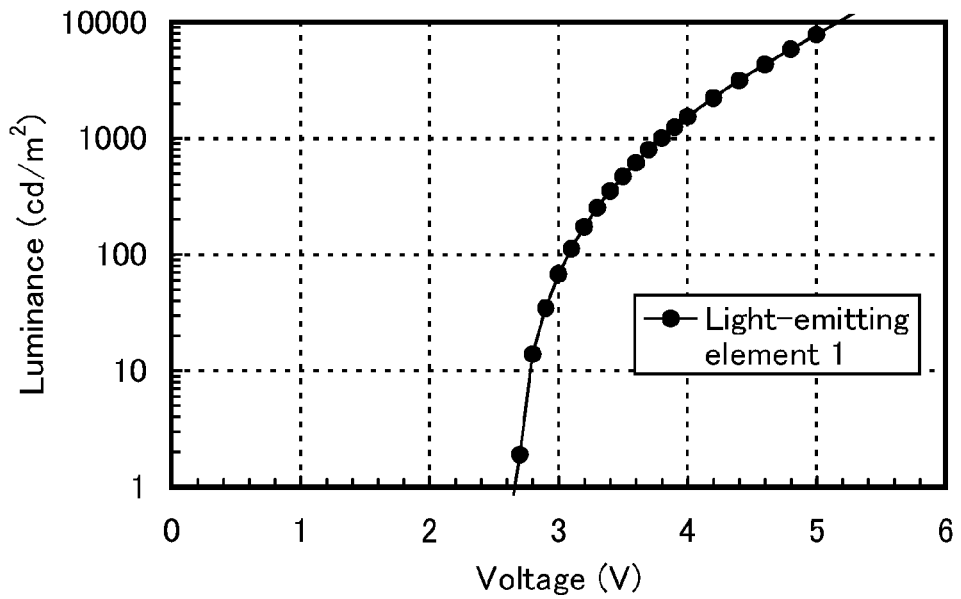
FIG. 12 shows voltage-luminance characteristics of a light-emitting element in Example 2.
Figure 13:
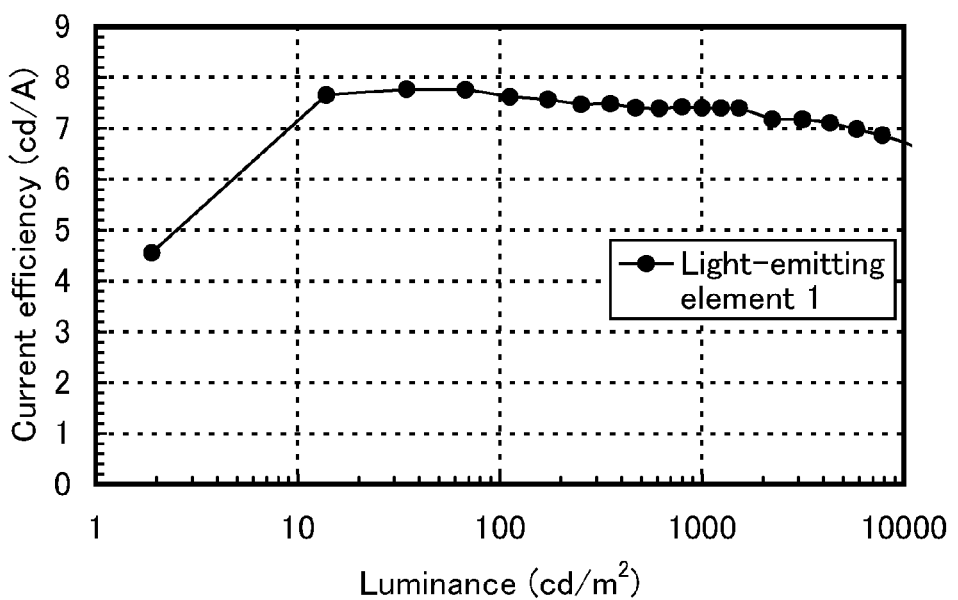
FIG. 13 shows current efficiency-luminance characteristics of the light-emitting element in Example 2.

FIG. 12 shows the voltage-luminance characteristics of the light-emitting element 1. In FIG. 12, the horizontal axis represents voltage (V) and the vertical axis represents luminance (cd/m$^2$). FIG. 13 shows the luminance-current efficiency characteristics of the light-emitting element 1. In FIG. 13, the horizontal axis represents luminance (cd/m$^2$) and the vertical axis represents current efficiency (cd/A). Table 3 shows the voltage (V), CIE chromaticity coordinate (x, y), current efficiency (cd/A), and external quantum efficiency (%) of the light-emitting element 1 at a luminance of 1000 cd/m$^2$.

TABLE 3

| | Voltage (V) | Chromaticity (x, y) | Current efficiency (cd/A) | External quantum efficiency (%) |
|---|---|---|---|---|
| Light-emitting element 1 | 3.8 | (0.14, 0.19) | 7.4 | 5.5 |

As shown in Table 3, the CIE chromaticity coordinate of the light-emitting element 1 is (x, y)=(0.14, 0.19) at a luminance of 1000 cd/m$^2$. This result shows that blue light emission originating from 1.6 mMemFLPAPrn is obtained from the light-emitting element 1.

FIG. 12 and FIG. 13 show that the light-emitting element 1 has low driving voltage and high emission efficiency.

Figure 14:
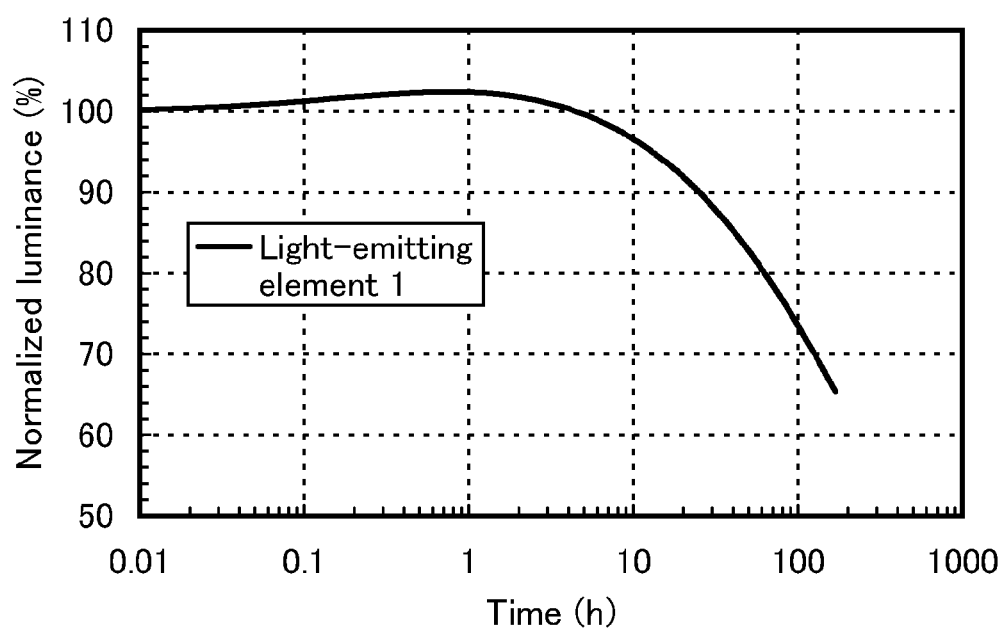
FIG. 14 shows results of a reliability test of the light-emitting element in Example 2.

Next, the light-emitting element 1 was subjected to a reliability test. FIG. 14 shows results of the reliability test. In FIG. 14, the vertical axis represents normalized luminance (%) on the assumption that the initial luminance is 100%, and the horizontal axis represents driving time (h) of the light-emitting element.

In the reliability test, the light-emitting element of this example was driven under the conditions where the initial luminance was 5000 cd/m$^2$ and the current density was constant.

FIG. 14 shows that the light-emitting element 1 kept 65% of the initial luminance after 170-hour driving. It is found that the light-emitting element 1 to which one embodiment of the present invention is applied has a long lifetime.

The above results indicate that an element having high emission efficiency can be achieved by using the composite material of one embodiment of the present invention for a hole-injection layer of the light-emitting element. The above results also indicate that a light-emitting element having low driving voltage can be provided by using the composite material of one embodiment of the present invention for a hole-injection layer of the light-emitting element. The above results also indicate that a light-emitting element having a long lifetime can be manufactured by using the composite material of one embodiment of the present invention for a hole-injection layer.

Example 3

Figure 18B:
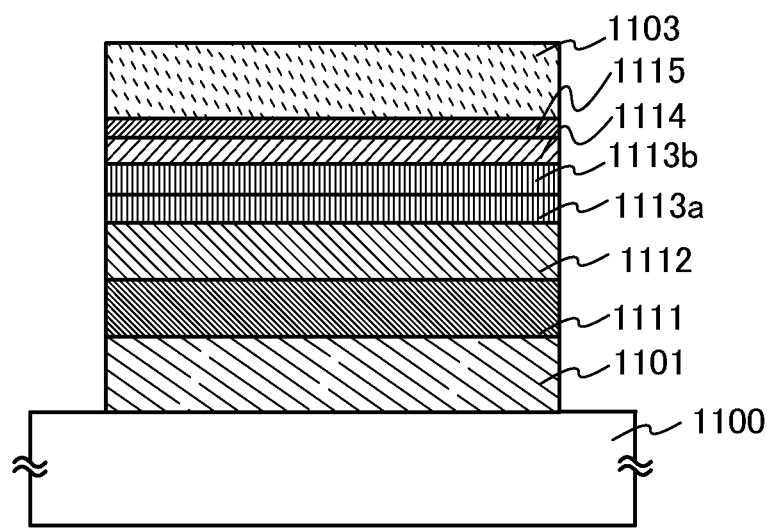

In this example, light-emitting elements each of which is one embodiment of the present invention will be described with reference to FIG. 18B. Shown below are structural formulae of materials used in this example. Note that the structural formulae of the materials used in the above examples are omitted here.

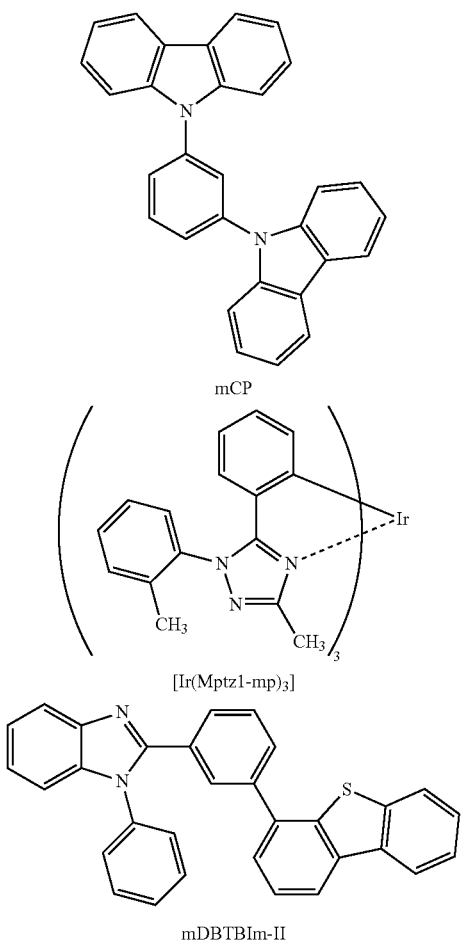

mCP

[Ir(Mptz1-mp)₃]

mDBTBIm-II

Methods of manufacturing a light-emitting element 2 and a light-emitting element 3 of this example will be described below.

(Light-Emitting Element 2)

First, a film of ITSO was formed over a glass substrate 1100 by a sputtering method to form a first electrode 1101 serving as an anode. The thickness of the first electrode 1101 was set to 110 nm, and the area thereof was set to 2 mm×2 mm.

In pretreatment for forming the light-emitting element on the substrate 1100, UV ozone treatment was performed for 370 seconds after washing of a surface of the substrate with water and baking performed at 200° C. for one hour.

After that, the substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed on a substrate holder in the vacuum evaporation apparatus so that a surface on which the first electrode 1101 was provided faced downward. The pressure in the vacuum evaporation apparatus was reduced to about $10^{-4}$ Pa. Then, mBP3P and molybdenum(VI) oxide were co-evaporated to form a hole-injection layer 1111 on the first electrode 1101. The thickness of the hole-injection layer 1111 was set to 60 nm. The mass ratio of mBP3P to molybdenum oxide was adjusted to 4:2 (=mBP3P: molybdenum oxide).

Next, on the hole-injection layer 1111, a film of 1,3-bis(N-carbazolyl)benzene (abbreviation: mCP) was formed to a thickness of 20 nm to form a hole-transport layer 1112.

Further, on the hole-transport layer 1112, mBP3P and tris[3-methyl-1-(2-methylphenyl)-5-phenyl-1H-1,2,4-triazolato]iridium(III) (abbreviation: [Ir(Mptz1-mp)₃]) were co-evaporated to form a first light-emitting layer 1113a. Here, the mass ratio of mBP3P to [Ir(Mptz1-mp)₃] was adjusted to 1:0.08 (=mBP3P: [Ir(Mptz1-mp)₃]). The thickness of the first light-emitting layer 1113a was 30 nm.

Then, on the first light-emitting layer 1113a, 2-[3-(dibenzothiophen-4-yl)phenyl]-1-phenyl-1H-benzimidazole (abbreviation: mDBTBIm-II) and [Ir(Mptz1-mp)₃] were co-evaporated to form a second light-emitting layer 1113b. Here, the mass ratio of mDBTBIm-II to [Ir(Mptz1-mp)₃] was adjusted to 1:0.08 (=mDBTBIm-II: [Ir(Mptz1-mp)₃]). The thickness of the second light-emitting layer 1113b was 10 nm.

Next, on the second light-emitting layer 1113b, a film of BPhen was formed to a thickness of 15 nm to form an electron-transport layer 1114.

Furthermore, on the electron-transport layer 1114, a film of LiF was formed to a thickness of 1 nm by evaporation to form an electron-injection layer 1115.

Lastly, a film of aluminum was formed to a thickness of 200 nm by evaporation to form a second electrode 1103 serving as a cathode. Through the above steps, the light-emitting element 2 of this example was manufactured.

(Light-Emitting Element 3)

A hole-transport layer 1112 of the light-emitting element 3 was formed by forming a film of mBP3P to a thickness of 20 nm. Components other than the hole-transport layer 1112 were formed in a similar manner to those of the light-emitting element 2.

Note that in all the above evaporation steps, evaporation was performed by a resistance-heating method.

Table 4 shows the element structures of the light-emitting element 2 and the light-emitting element 3 obtained as described above.

TABLE 4

| | First electrode | Hole-injection layer | Hole-transport layer | First light-emitting layer | Second light-emitting layer | Electron-transport layer | Electron-injection layer | Second electrode |
|---|---|---|---|---|---|---|---|---|
| Light-emitting element 2 | ITSO 110 nm | mBP3P:MoOx (=4:2) 60 nm | mCP 20 nm | mBP3P: [Ir(Mptz1-mp)₃] (=1:0.08) 30 nm | mDBTBIm-II: [Ir(Mptz1-mp)₃] (=1:0.08) 10 nm | BPhen 15 nm | LiF 1 nm | Al 200 nm |
| Light-emitting element 3 | ITSO 110 nm | mBP3P:MoOx (=4:2) 60 nm | mBP3P 20 nm | mBP3P: Ir(Mptz1-mp)₃] (=1:0.08) 30 nm | mDBTBIm-II: [Ir(Mptz1-mp)₃] (=1:0.08) 10 nm | BPhen 15 nm | LiF 1 nm | Al 200 nm |

In a glove box containing a nitrogen atmosphere, the light-emitting elements 2 and 3 were sealed so as not to be exposed to the air. Then, operation characteristics of the light-emitting elements 2 and 3 were measured. Note that the measurement was carried out at room temperature (in an atmosphere kept at 25° C.).

Figure 15:
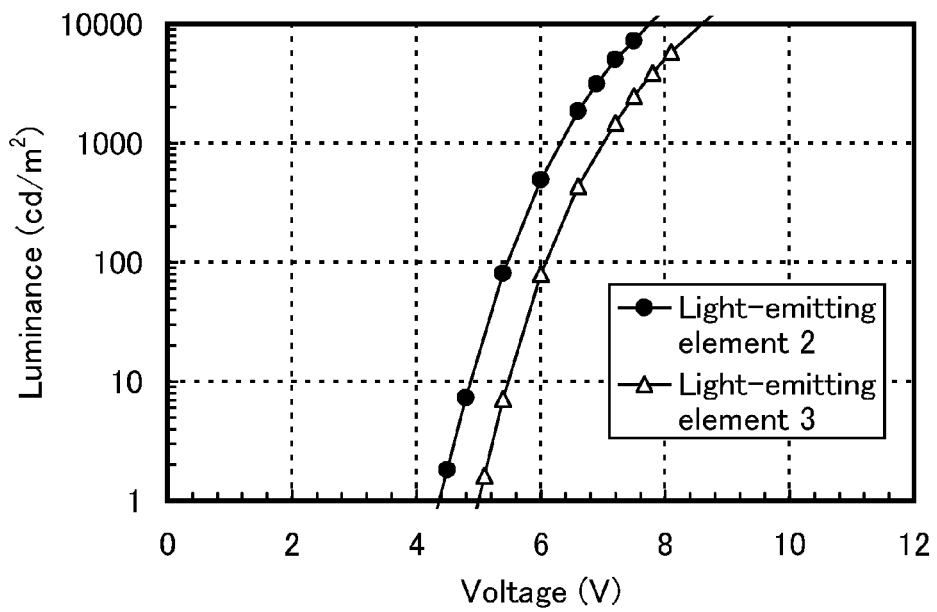
FIG. 15 shows voltage-luminance characteristics of light-emitting elements in Example 3.
Figure 16:
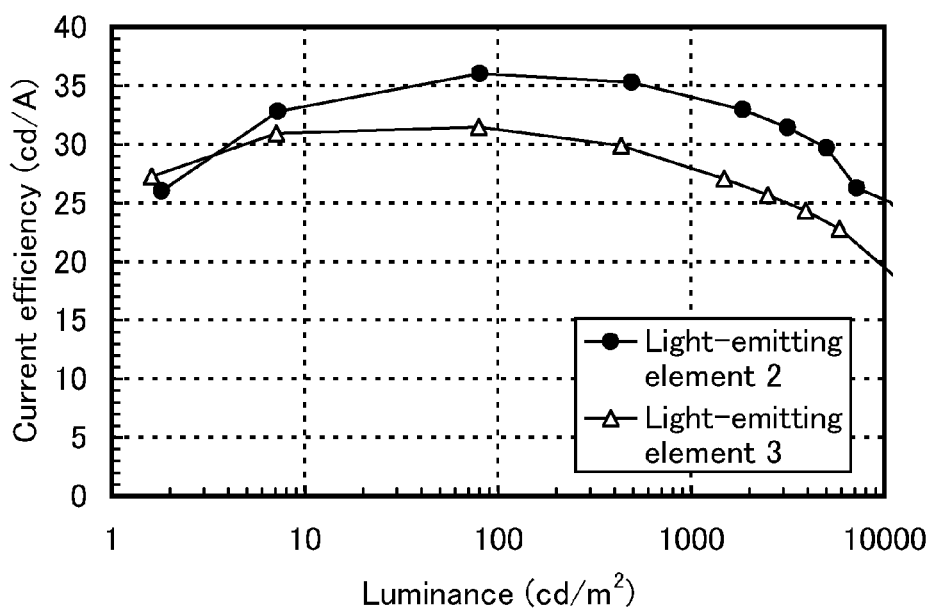
FIG. 16 shows luminance-current efficiency characteristics of the light-emitting elements in Example 3.

FIG. 15 shows the voltage-luminance characteristics of the light-emitting elements 2 and 3. In FIG. 15, the horizontal axis represents voltage (V) and the vertical axis represents luminance (cd/m$^2$). FIG. 16 shows the luminance-current efficiency characteristics of the light-emitting elements 2 and 3. In FIG. 16, the horizontal axis represents luminance (cd/m$^2$) and the vertical axis represents current efficiency (cd/A). Table 5 shows the voltage (V), CIE chromaticity coordinate (x, y), current efficiency (cd/A), and external quantum efficiency (%) of each of the light-emitting elements 2 and 3 at a luminance of about 500 cd/m$^2$.

TABLE 5

|  | Voltage (V) | Chromaticity (x, y) | Current efficiency (cd/A) | External quantum efficiency (%) |
| --- | --- | --- | --- | --- |
| Light-emitting element 2 | 6.0 | (0.18, 0.29) | 35 | 18 |
| Light-emitting element 3 | 6.6 | (0.18, 0.30) | 30 | 15 |

The CIE chromaticity coordinates of the light-emitting element 2 and the light-emitting element 3 are, respectively, (x, y)=(0.18, 0.29) and (x, y)=(0.18, 0.30) at a luminance of about 500 cd/m$^2$. These results show that blue light emission originating from [Ir(Mptz1-mp)$_3$] is obtained from each of the light-emitting elements 2 and 3.

FIG. 15 and FIG. 16 show that the light-emitting elements 2 and 3 each have low driving voltage and high emission efficiency.

Figure 17:
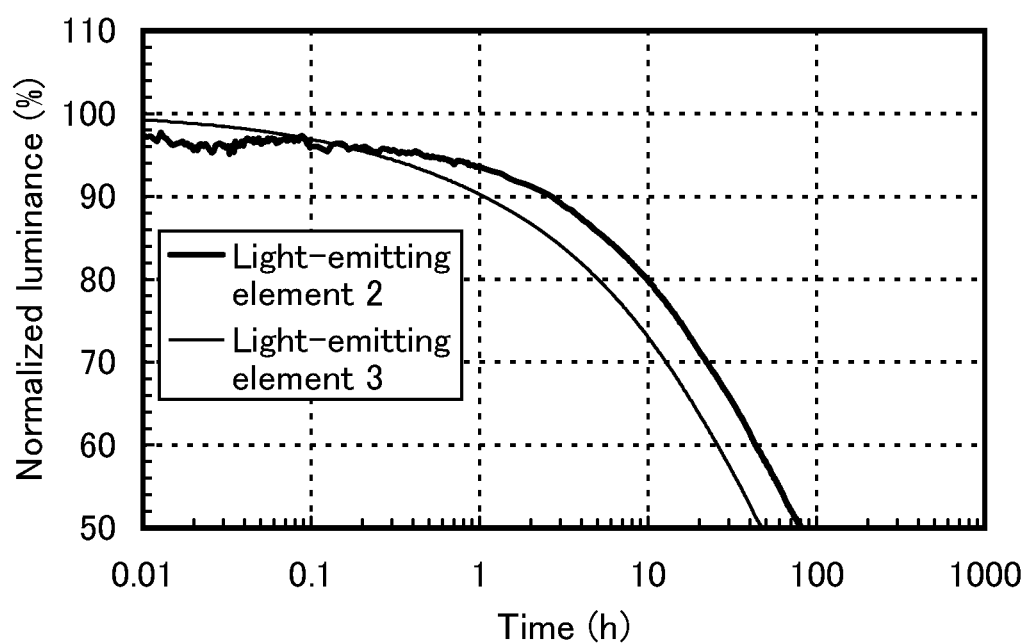
FIG. 17 shows results of reliability tests of the light-emitting elements in Example 3.

Next, the light-emitting elements 2 and 3 were subjected to reliability tests. FIG. 17 shows results of the reliability tests. In FIG. 17, the vertical axis represents normalized luminance (%) on the assumption that the initial luminance is 100%, and the horizontal axis represents driving time (h) of the light-emitting elements.

In the reliability tests, the light-emitting elements of this example were driven under the conditions where the initial luminance was 300 cd/m$^2$ and the current density was constant.

According to FIG. 17, the light-emitting element 2 kept 50% of the initial luminance after 81-hour driving, and the light-emitting element 3 kept 50% of the initial luminance after 47-hour driving.

Since a phosphorescent substance which exhibits blue emission or a host material which is used together with the phosphorescent substance has a high T1 level, the phosphorescent substance or the host material is likely to have a wide band gap and a low HOMO level. Thus, it is difficult to inject holes to the light-emitting substance, and an increase in driving voltage or a reduction in lifetime easily occurs. The organic compound (here, mBP3P) used for the composite material of one embodiment of the present invention has a low HOMO level. The use of the composite material of one embodiment of the present invention for a hole-injection layer makes it possible to efficiently inject holes into a hole-transport layer. In particular, when mBP3P is used as an organic compound included in a hole-injection layer (a layer including a composite material of one embodiment of the present invention), as a material for a hole-transport layer, and as a host material for a light-emitting layer, holes can be efficiently injected into the light-emitting layer. As described in this example, the composite material of one embodiment of the present invention can be suitably used for an element which emits blue phosphorescence. With the use of the composite material of one embodiment of the present invention, it is possible to achieve a light-emitting element in which an increase in driving voltage and a reduction in lifetime are suppressed.

Example 4

In this example, light-emitting elements each of which is one embodiment of the present invention will be described with reference to FIG. 18A. Shown below are structural formulae of materials used in this example. Note that the structural formulae of the materials used in the above examples are omitted here.

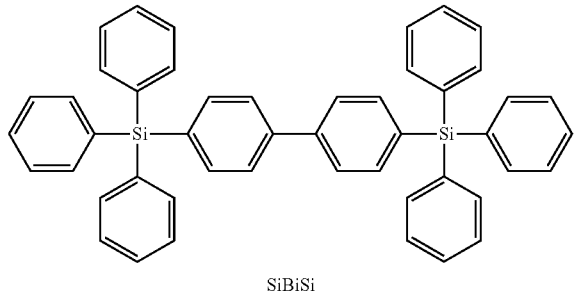 [SMILES: c1ccc([Si](c2ccccc2)(c2ccccc2)c2ccc(-c3ccc([Si](c4ccccc4)(c4ccccc4)c4ccccc4)cc3)cc2)cc1 ; "SiBiSi"]

SiBiSi

Methods of manufacturing light-emitting elements 4 and 5 of this example will be described below.

(Light-Emitting Element 4)

First, a film of ITSO was formed over a glass substrate 1100 by a sputtering method, so that a first electrode 1101 serving as an anode was formed. The thickness of the first electrode 1101 was set to 110 nm, and the area thereof was set to 2 mm×2 mm.

In pretreatment for forming the light-emitting element on the substrate 1100, UV ozone treatment was performed for 370 seconds after washing of a surface of the substrate with water and baking performed at 200° C. for one hour.

After that, the substrate 1100 was transferred into a vacuum evaporation apparatus where the pressure had been reduced to approximately 10$^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed on a substrate holder in the vacuum evaporation apparatus so that a surface on which the first electrode 1101 was provided faced downward. The pressure in the vacuum evaporation apparatus was reduced to about 10$^{-4}$ Pa. Then, SiPSi and molybdenum(VI) oxide were co-evaporated to form a hole-injection layer 1111 on the first electrode 1101.

The thickness of the hole-injection layer 1111 was set to 50 nm. The mass ratio of SiPSi to molybdenum oxide was adjusted to 4:2 (=SiPSi: molybdenum oxide).

Next, on the hole-injection layer 1111, a film of PCzPA was formed to a thickness of 20 nm to form a hole-transport layer 1112.

Furthermore, on the hole-transport layer 1112, CzPA and 1.6 mMemFLPAPrn were co-evaporated to form a light-emitting layer 1113. Here, the mass ratio of CzPA to 1.6 mMemFLPAPrn was adjusted to 1:0.04 (=CzPA: 1.6 mMemFLPAPrn). The thickness of the light-emitting layer 1113 was set to 30 nm.

Further, on the light-emitting layer 1113, a film of CzPA was formed to a thickness of 10 nm to form a first electron-transport layer 1114a.

Then, on the first electron-transport layer 1114a, a film of BPhen was formed to a thickness of 15 nm to form a second electron-transport layer 1114b.

Furthermore, on the second electron-transport layer 1114b, a film of LiF was formed to a thickness of 1 nm by evaporation to form an electron-injection layer 1115.

Lastly, a film of aluminum was formed to a thickness of 200 nm by evaporation to form a second electrode 1103 serving as a cathode. Through the above steps, the light-emitting element 4 of this example was manufactured.

(Light-Emitting Element 5)

A hole-injection layer 1111 of the light-emitting element 5 was formed by co-evaporation of 4,4'-bis(triphenylsilyl)biphenyl (abbreviation: SiBiSi) and molybdenum(VI) oxide. The thickness of the hole-injection layer 1111 was set to 50 nm. The mass ratio of SiBiSi to molybdenum oxide was adjusted to 4:2 (=SiBiSi: molybdenum oxide). Components other than a hole-injection layer 1111 were formed in a similar manner to those of the light-emitting element 4.

Note that in all the above evaporation steps, evaporation was performed by a resistance-heating method.

Table 6 shows the element structures of the light-emitting element 4 and the light-emitting element 5 obtained as described above.

In a glove box containing a nitrogen atmosphere, the light-emitting elements 4 and 5 were sealed so as not to be exposed to the air. Then, operation characteristics of the light-emitting elements 4 and 5 were measured. Note that the measurement was carried out at room temperature (in an atmosphere kept at 25° C.).

Figure 19:
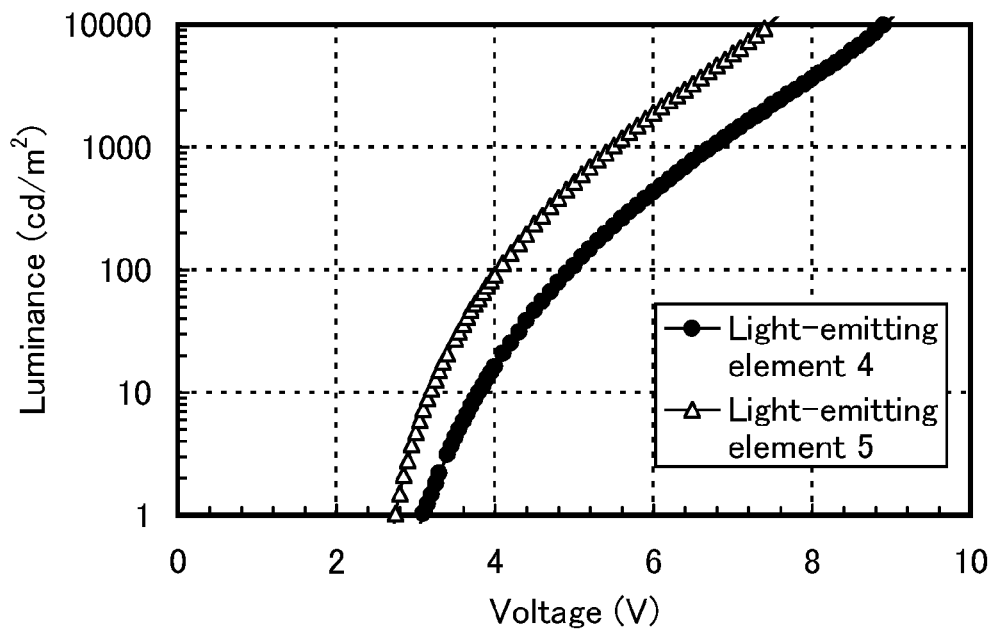
FIG. 19 shows voltage-luminance characteristics of light-emitting elements in Example 4.
Figure 20:
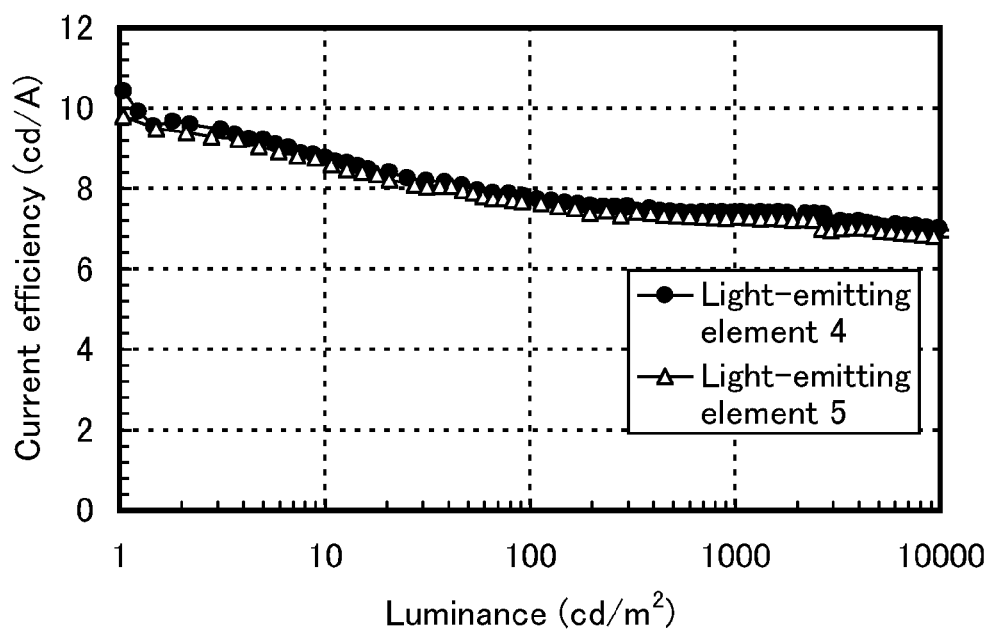
FIG. 20 shows luminance-current efficiency characteristics of the light-emitting elements in Example 4.

FIG. 19 shows the voltage-luminance characteristics of the light-emitting elements 4 and 5. In FIG. 19, the horizontal axis represents voltage (V) and the vertical axis represents luminance (cd/m$^2$). FIG. 20 shows the luminance-current efficiency characteristics of the light-emitting elements 4 and 5. In FIG. 20, the horizontal axis represents luminance (cd/m$^2$) and the vertical axis represents current efficiency (cd/A). Table 7 shows the voltage (V), CIE chromaticity coordinate (x, y), current efficiency (cd/A), and external quantum efficiency (%) of each of the light-emitting elements 4 and 5 at a luminance of 1000 cd/m$^2$.

TABLE 7

| | Voltage (V) | Chromaticity (x, y) | Current efficiency (cd/A) | External quantum efficiency (%) |
|---|---|---|---|---|
| Light-emitting element 4 | 6.6 | (0.14, 0.17) | 7.4 | 3.5 |
| Light-emitting element 5 | 5.5 | (0.14, 0.16) | 7.3 | 4.2 |

The CIE chromaticity coordinates of the light-emitting element 4 and the light-emitting element 5 are, respectively, (x, y)=(0.14, 0.17) and (x, y)=(0.14, 0.16) at a luminance of 1000 cd/m$^2$. These results show that blue light emission originating from 1.6 mMemFLPAPrn is obtained from each of the light-emitting elements 4 and 5.

FIG. 19 and FIG. 20 show that the light-emitting elements 4 and 5 each have low driving voltage and high emission efficiency. Further, the light-emitting element 5 in which SiBiSi including a biphenylene group is used has particularly low driving voltage.

The above results indicate that an element having high emission efficiency can be achieved by using the composite material of one embodiment of the present invention for a hole-injection layer of the light-emitting element. The above results also indicate that a light-emitting element having low driving voltage can be provided by using the composite material of one embodiment of the present invention for a hole-injection layer of the light-emitting element.

TABLE 6

| | First electrode | Hole-injection layer | Hole-transport layer | Light-emitting layer | First electron-transport layer | Second electron-transport layer | Electron-injection layer | Second electrode |
|---|---|---|---|---|---|---|---|---|
| Light-emitting element 4 | ITSO 110 nm | SiPSi:MoOx (=4:2) 50 nm | PCzPA 10 nm | CzPA: 1,6mMemFLPAPrn (=1:0.04) 30 nm | CzPA 10 nm | BPhen 15 nm | LiF 1 nm | Al 200 nm |
| Light-emitting element 5 | ITSO 110 nm | SiBiSi:MoOx (=4:2) 50 nm | PCzPA 10 nm | CzPA: 1,6mMemFLPAPrn (=1:0.04) 30 nm | CzPA 10 nm | BPhen 15 nm | LiF 1 nm | Al 200 nm |

Example 5

In this example, 1,3,5-tris[(3,5-diphenyl)phenyl]benzene (abbreviation: mTP3P), an organic compound which can be used for the composite material of one embodiment of the present invention, will be described. Shown below is the structural formula of mTP3P.

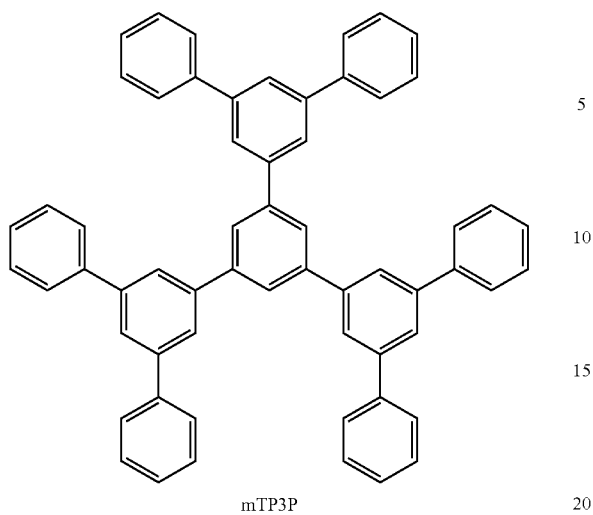

mTP3P

Figure 21A:
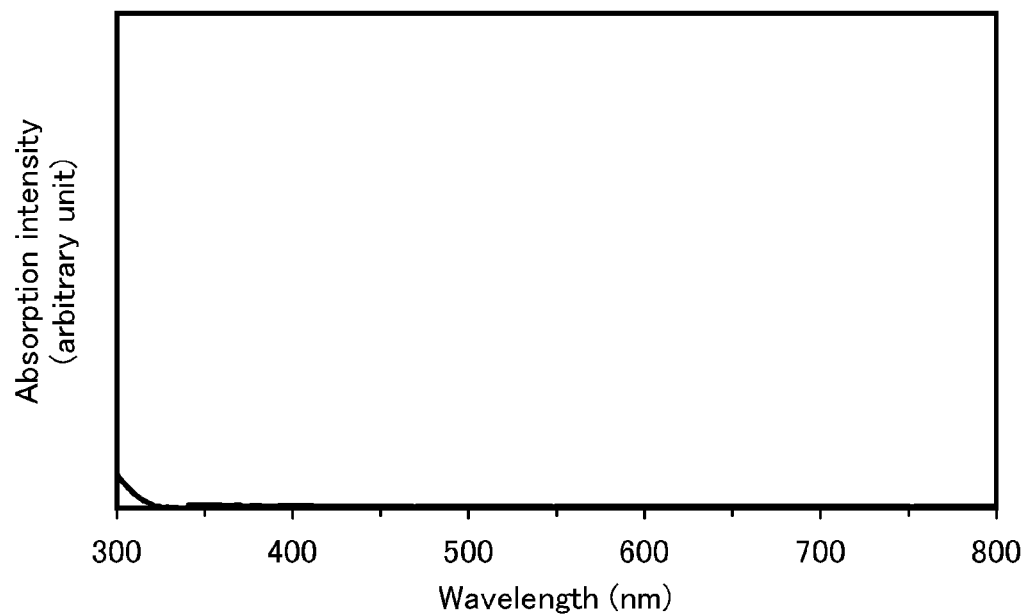
FIGS. 21A and 21B show an absorption spectrum and an emission spectrum of mTP3P in a toluene solution of mTP3P.
Figure 21B:
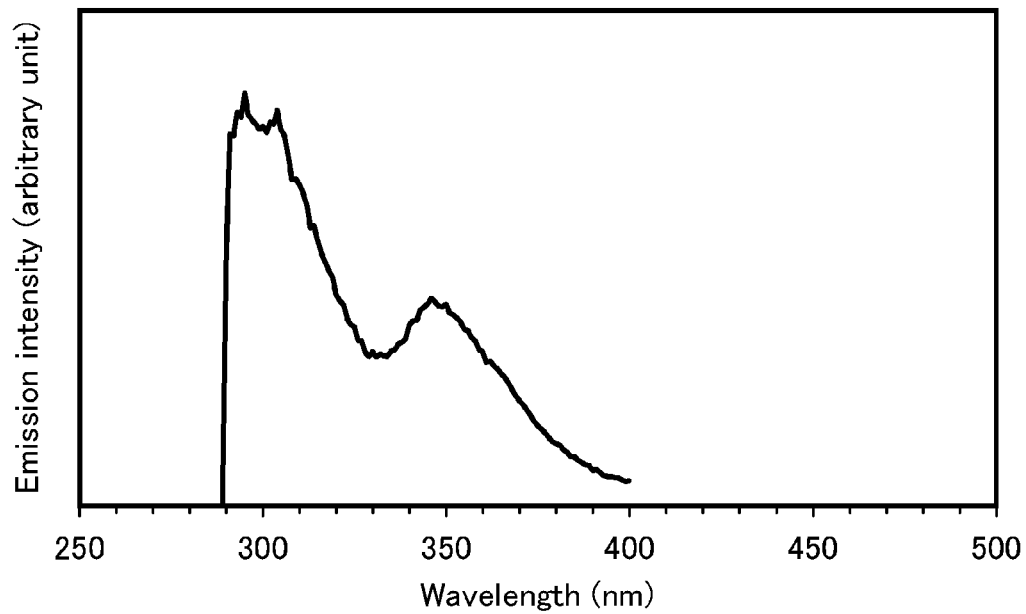
Figure 22A:
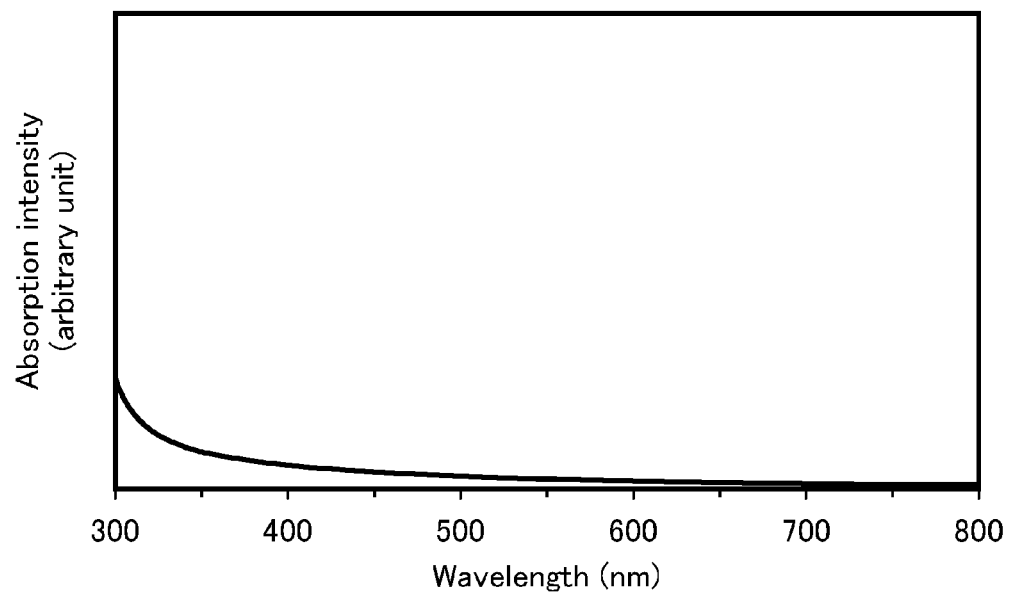
FIGS. 22A and 22B show an absorption spectrum and an emission spectrum of a thin film of mTP3P.
Figure 22B:
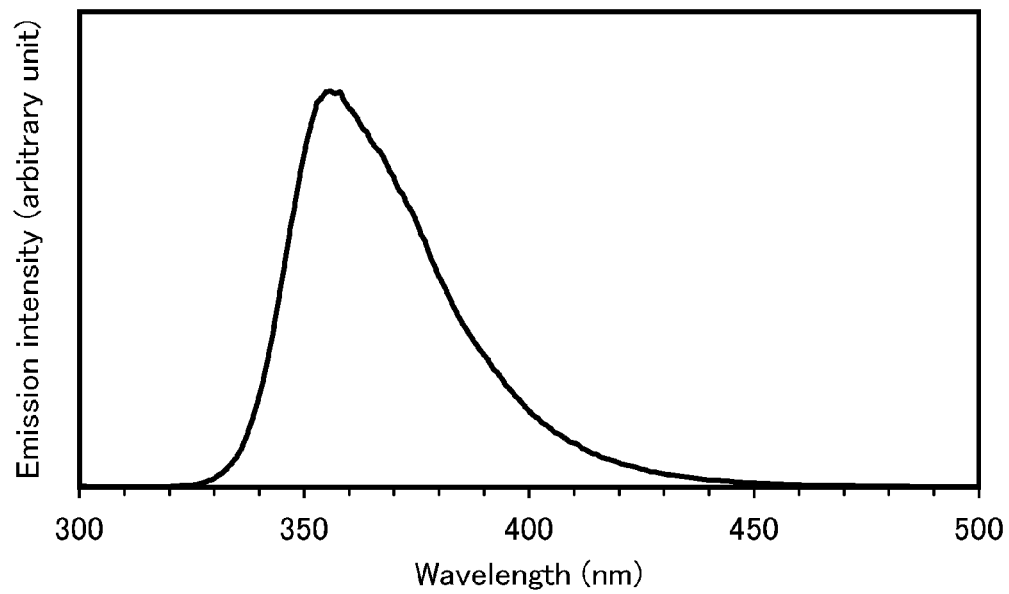

FIG. 21A shows an absorption spectrum of mTP3P in a toluene solution of mTP3P, and FIG. 21B shows an emission spectrum thereof. FIG. 22A shows an absorption spectrum of a thin film of mTP3P, and FIG. 22B shows an emission spectrum thereof. The absorption spectrum was measured with an ultraviolet-visible spectrophotometer (V-550, manufactured by JASCO Corporation). The measurements were performed in such a manner that the solution was put in a quartz cell. The absorption spectrum of the solution was obtained by subtracting the absorption spectra of quartz and toluene from those of quartz and the solution, and the absorption spectrum of the thin film was obtained by subtracting the absorption spectrum of a quartz substrate from those of the quartz substrate and the thin film. In FIG. 21A and FIG. 22A, the horizontal axis represents wavelength (nm) and the vertical axis represents absorption intensity (arbitrary unit). In FIGS. 21B and 21B, the horizontal axis represents wavelength (nm) and the vertical axis represents emission intensity (arbitrary unit). In the case of the toluene solution, the emission wavelength peaks are 295 nm, 304 nm, and 347 nm (excitation wavelength: 385 nm). In the case of the thin film, the emission wavelength peak is 356 nm (excitation wavelength: 271 nm).

As is clear from FIG. 21A and FIG. 22A, almost no absorption in the visible light region is observed in the absorption spectra of mTP3P in the toluene solution of mTP3P and the thin film of mTP3P. The fact that both the solution and the thin film exhibit almost no absorption in the visible light region indicates that the organic compound is suitable for both a film of a single organic compound and for a film of a mixture with another organic compound. In addition, as is clear from FIG. 21B and FIG. 22B, the emission peaks of mTP3P are located on the short wavelength side. Thus, mTP3P can be suitably used for the composite material of one embodiment of the present invention, as a material for a hole-transport layer, and for a light-emitting layer (particularly as a host material).

Further, mTP3P has a high glass transition temperature (Tg) of 132° C. and has stable film quality. This also shows that mTP3P can be suitably used for the composite material of one embodiment of the present invention.

Example 6

In this example, bis[3,5-di(biphenyl-3-yl)phenyl]diphenylsilane (abbreviation: mBP22 PSi), an organic compound which can be used for the composite material of one embodiment of the present invention, will be described. Shown below is the structural formula of mBP22 PSi.

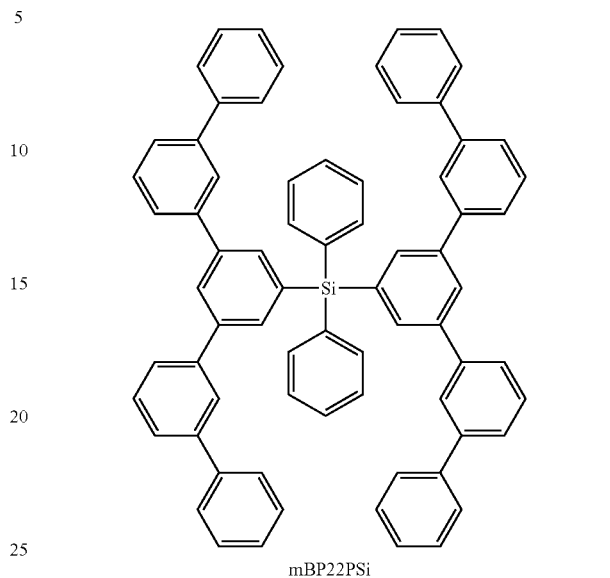

mBP22PSi

[Synthesis Method of mBP22 PSi]

Shown below is the synthesis scheme of mBP22 PSi.

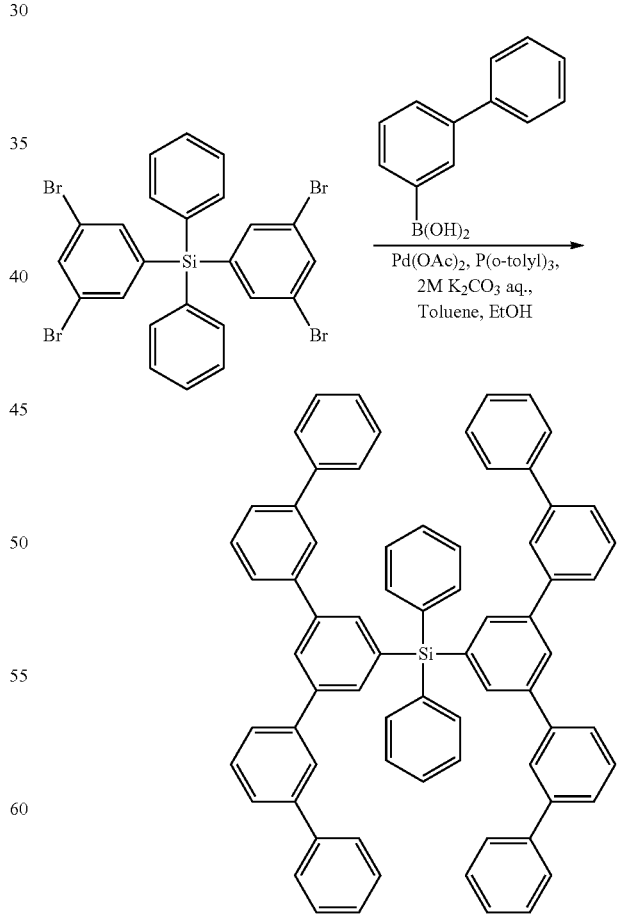

mBP22PSi

In a 100-mL three-neck flask were put 1.4 g (2.2 mmol) of diphenyl-di(3,5-dibromobenzene)silane, 1.9 g (9.7 mmol) of 3-biphenylboronic acid, 110 mg (0.5 mmol) of palladium(II) acetate, and 290 mg (1.0 mmol) of tri(ortho-tolyl)phosphine, and the atmosphere in the flask was replaced with nitrogen. Then, 20 mL of toluene, 2 mL of ethanol, and 10 mL of a 2.0M aqueous solution of potassium carbonate (2.7 g of potassium carbonate) were added, and the mixture was degassed by being stirred under reduced pressure. The mixture was stirred at 85° C. for 14 hours under a nitrogen stream. Then, 0.4 g (2.2 mmol) of 3-biphenylboronic acid, 290 mg (1.0 mmol) of tri(ortho-tolyl)phosphine, and 110 mg (0.5 mmol) of palladium acetate were added, and the mixture was stirred at 85° C. for 13 hours under a nitrogen stream. After the stirring, the mixture was filtered through Celite (produced by Wako Pure Chemical Industries, Ltd., Catalog No. 531-16855). Then, water is added to the filtrate and extraction with toluene was performed to obtain an organic layer. The organic layer was washed with saturated saline, and magnesium sulfate was added thereto so that moisture was adsorbed. The obtained mixture was gravity-filtered, and the filtrate was concentrated to give a yellow oily substance. The yellow oily substance was purified by silica gel column chromatography (hexane: toluene=3:1) to give a white solid. Methanol was added to the while solid, and then irradiation with ultrasonic waves was performed to obtain a suspension. The suspension was suction-filtered to give 1.14 g of a white solid which was a target substance (yield: 56%).

This compound was identified as mBP22 PSi, which was a target substance of the synthesis, by nuclear magnetic resonance (NMR) spectroscopy $^1$H NMR data of the obtained substance are as follows: $^1$H NMR (CDCl$_3$, 300 MHz): δ (ppm)=7.30-7.59 (m, 38H), 7.74-7.79 (m, 8H), 7.95 (d, J=1.5 Hz, 4H), 7.97 (d, J=1.5 Hz, 2H).

Figure 23A:
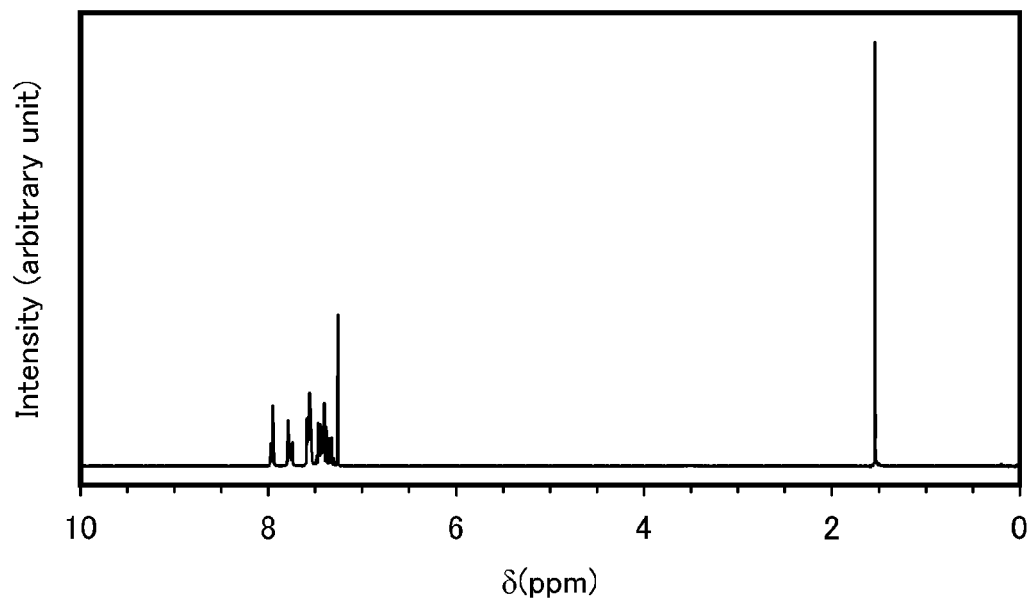
FIGS. 23A and 23B are $^1$H NMR charts of mBP22 PSi.
Figure 23B:
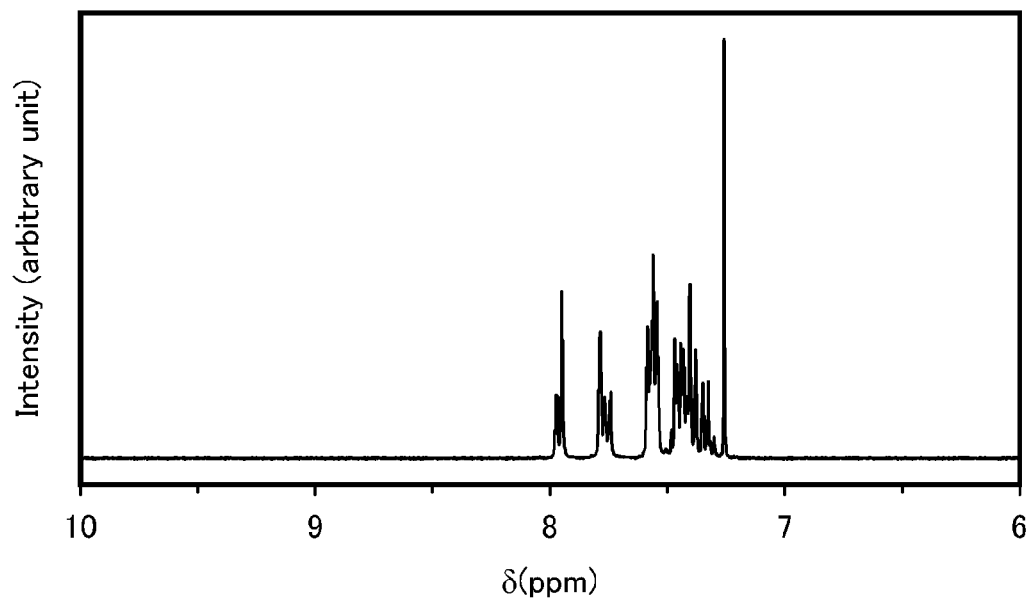

FIGS. 23A and 23B are $^1$H-NMR charts. Note that FIG. 23B is a chart showing an enlarged part of FIG. 23A in the range of 6.00 ppm to 10.00 ppm.

Figure 24A:
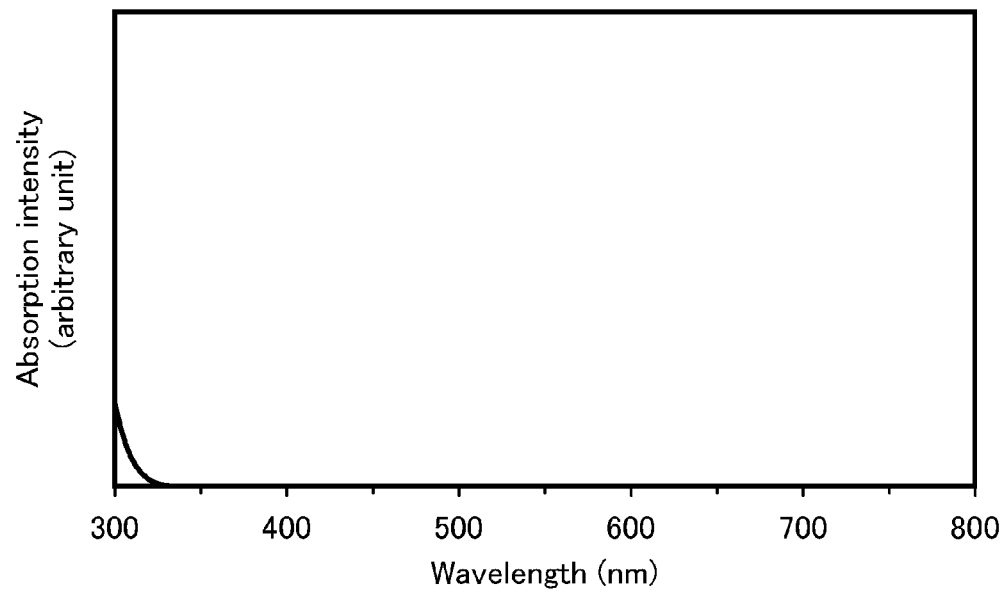
FIGS. 24A and 24B show an absorption spectrum and an emission spectrum of mBP22 PSi in a toluene solution of mBP22 PSi.
Figure 24B:
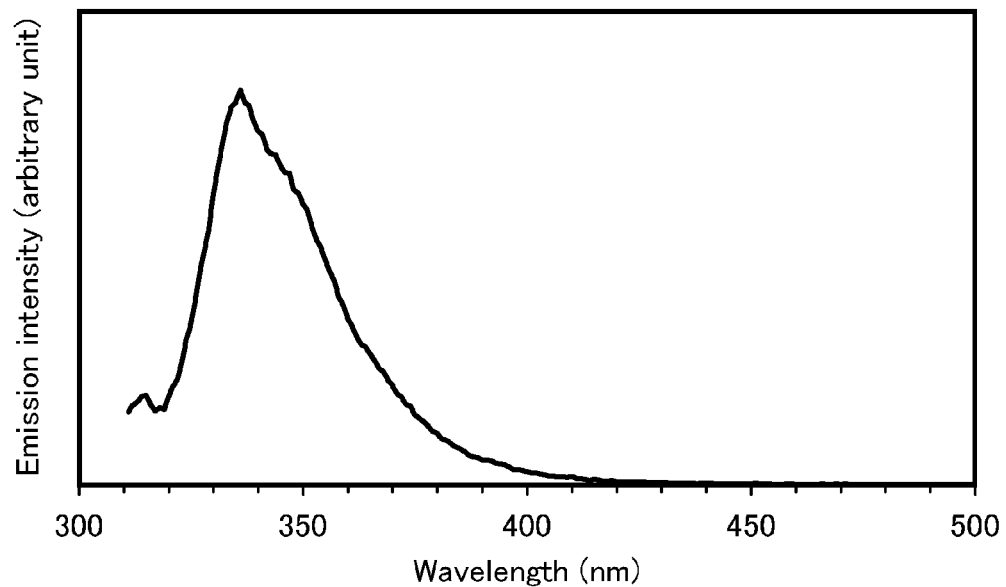
Figure 25A:
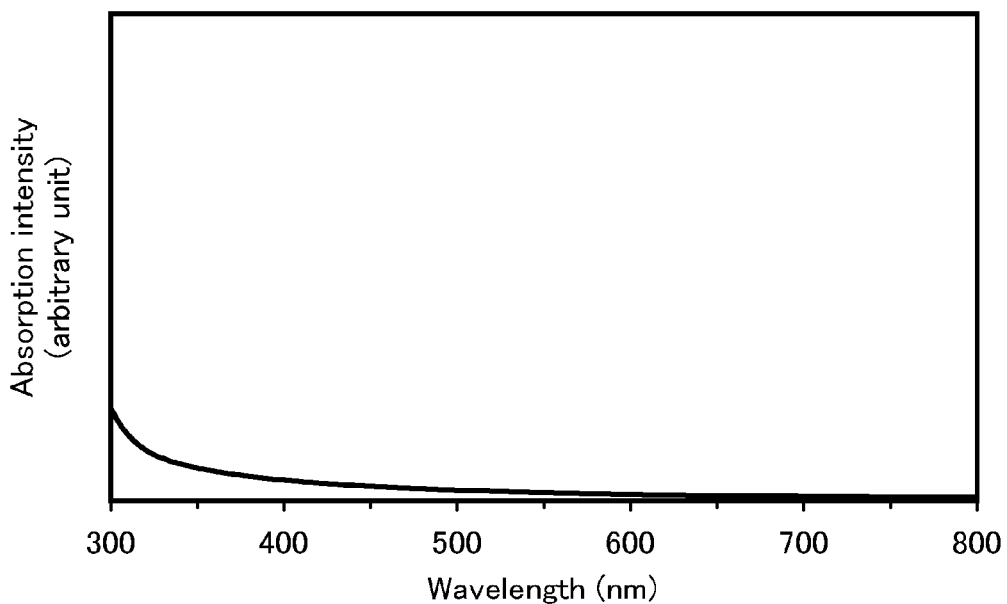
FIGS. 25A and 25B show an absorption spectrum and an emission spectrum of a thin film of mBP22 PSi.
Figure 25B:
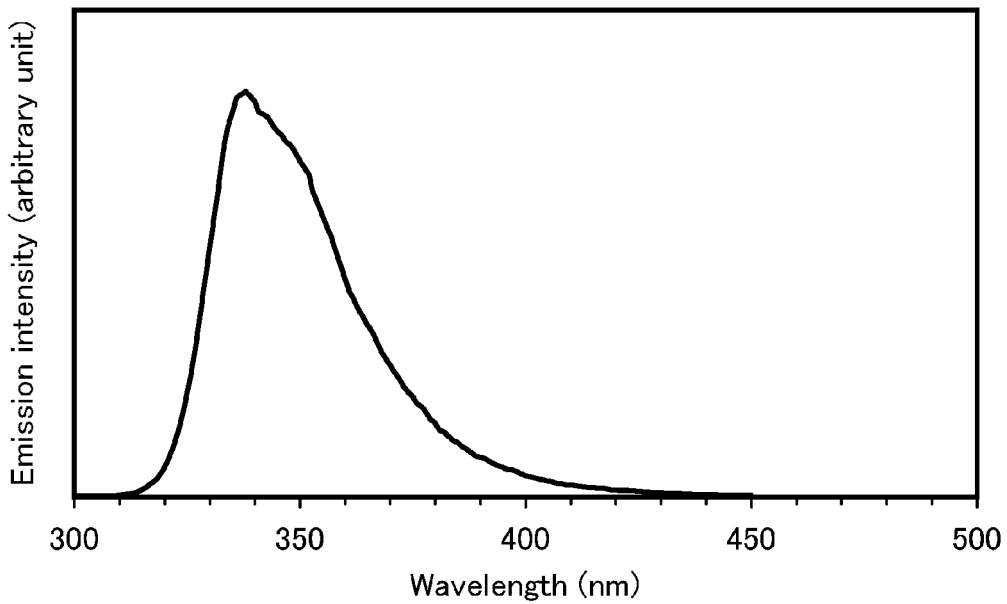

FIG. 24A shows an absorption spectrum of mBP22 PSi in a toluene solution of mBP22 PSi, and FIG. 24B shows an emission spectrum thereof. FIG. 25A shows an absorption spectrum of a thin film of mBP22 PSi, and FIG. 25B shows an emission spectrum thereof. The absorption spectrum was measured with an ultraviolet-visible spectrophotometer (V-550, manufactured by JASCO Corporation). The measurements were performed in such a manner that the solution was put in a quartz cell. The absorption spectrum of the solution was obtained by subtracting the absorption spectra of quartz and toluene from those of quartz and the solution, and the absorption spectrum of the thin film was obtained by subtracting the absorption spectrum of a quartz substrate from those of the quartz substrate and the thin film. In each of FIG. 24A and FIG. 25A, the horizontal axis represents wavelength (nm) and the vertical axis represents absorption intensity (arbitrary unit). In each of FIG. 24B and FIG. 25B, the horizontal axis represents wavelength (nm) and the vertical axis represents emission intensity (arbitrary unit). In the case of the toluene solution, the emission wavelength peak is 336 nm (excitation wavelength: 287 nm). In the case of the thin film, the emission wavelength peaks are 338 nm, 342 nm, and 348 nm (excitation wavelength: 256 nm).

As is clear from FIG. 24A and FIG. 25A, almost no absorption in the visible light region is observed in the absorption spectra of mBP22 PSi in the toluene solution of mBP22 PSi and the thin film of mBP22 PSi. The fact that both the solution and the thin film exhibit almost no absorption in the visible light region indicates that the organic compound is suitable for both a film of a single organic compound and for a film of a mixture with another organic compound. In addition, as is clear from FIG. 24B and FIG. 25B, the emission peaks of mBP22 PSi are located on the short wavelength side. The results of this example show that mBP22 PSi can be suitably used for the composite material of one embodiment of the present invention, as a host material for a hole-transport layer, and for a light-emitting layer (particularly as a host material).

Example 7

In this example, a light-emitting element of one embodiment of the present invention will be described with reference to FIG. 18B. The materials used in this example are used in the above examples, and therefore the structural formulae thereof are omitted here.

A method of manufacturing a light-emitting element 6 of this example will be described.
(Light-Emitting Element 6)

First, a film of ITSO was formed over a glass substrate 1100 by a sputtering method to form a first electrode serving as an anode. The thickness of the first electrode 1101 was set to 110 nm, and the area thereof was set to 2 mm×2 mm.

In pretreatment for forming the light-emitting element on the substrate 1100, UV ozone treatment was performed for 370 seconds after washing of a surface of the substrate with water and baking performed at 200° C. for one hour.

After that, the substrate 1100 was transferred into a vacuum evaporation apparatus where the pressure had been reduced to approximately 10$^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in the vacuum evaporation apparatus so that a surface on which the first electrode 1101 was provided faced downward. The pressure in the vacuum evaporation apparatus was reduced to about 10$^{-4}$ Pa. Then, on the first electrode 1101, mBP22 PSi and molybdenum(VI) oxide were co-evaporated to form a hole-injection layer 1111. The thickness of the hole-injection layer 1111 was set to 60 nm. The mass ratio of mBP22 PSi to molybdenum oxide was adjusted to 4:2 (=mBP22 PSi: molybdenum oxide).

Next, on the hole-injection layer 1111, mBP22 PSi was formed to a thickness of 20 nm to form a hole-transport layer 1112.

Further, mBP22 PSi and [Ir(Mptz1-mp)$_3$] were co-evaporated to form a first light-emitting layer 1113a on the hole-transport layer 1112. Here, the mass ratio of mBP22 PSi to [Ir(Mptz1-mp)$_3$] was adjusted to 1:0.06 (=mBP22 PSi: [Ir(Mptz1-mp)$_3$]). The thickness of the first light-emitting layer 1113a was set to 30 nm.

Then, mDBTBIm-II and [Ir(Mptz1-mp)$_3$] were co-evaporated to form a second light-emitting layer 1113b on the first light-emitting layer 1113a. Here, the mass ratio of mDBT-BIm-II to [Ir(Mptz1-mp)$_3$] was adjusted to 1:0.06 (=mDBT-BIm-II: [Ir(Mptz1-mp)$_3$]). The thickness of the second light-emitting layer 1113b was set to 10 nm.

Next, on the second light-emitting layer 1113b, a film of BPhen was formed to a thickness of 15 nm to form an electron-transport layer 1114.

Further, on the electron-transport layer 1114, a film of LiF was formed to a thickness of 1 nm by evaporation to form an electron-injection layer 1115.

Lastly, a film of aluminum was formed to a thickness of 200 nm by evaporation to form a second electrode 1103 serving as a cathode. Through the above steps, the light-emitting element 6 was manufactured.

Note that in all the above evaporation steps, evaporation was performed by a resistance-heating method.

Table 8 shows the element structure of the light-emitting element 6 obtained as described above.

TABLE 8

| | First electrode | Hole-injection layer | Hole-transport layer | First light-emitting layer | Second light-emitting layer | Electron-transport layer | Electron-injection layer | Second electrode |
|---|---|---|---|---|---|---|---|---|
| Light-emitting element 6 | ITSO 110 nm | mBP22PSi:MoOx (=4:2) 60 nm | mBP22PSi 20 nm | mBP22PSi: [Ir(Mptz1-mp)$_3$] (=1:0.06) 30 nm | mDBTBIm-II: [Ir(Mptz1-mp)$_3$] (=1:0.06) 10 nm | BPhen 15 nm | LiF 1 nm | Al 200 nm |

In a glove box containing a nitrogen atmosphere, the light-emitting element 6 was sealed so as not to be exposed to the air. Then, operation characteristics of the light-emitting element 6 were measured. Note that the measurement was carried out at room temperature (in an atmosphere kept at 25° C.).

Figure 26:
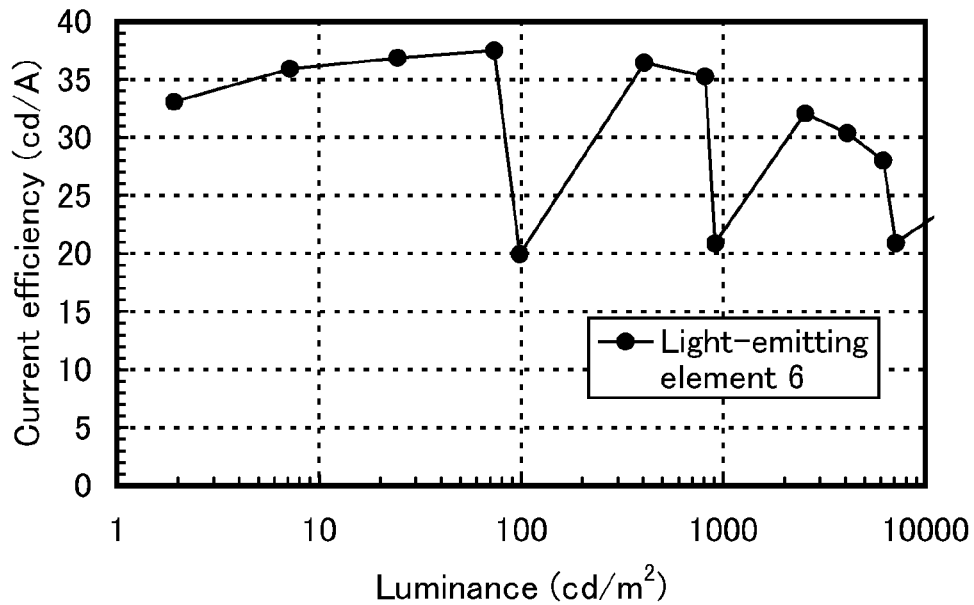
FIG. 26 shows luminance-current efficiency characteristics of a light-emitting element in Example 7.
Figure 27:
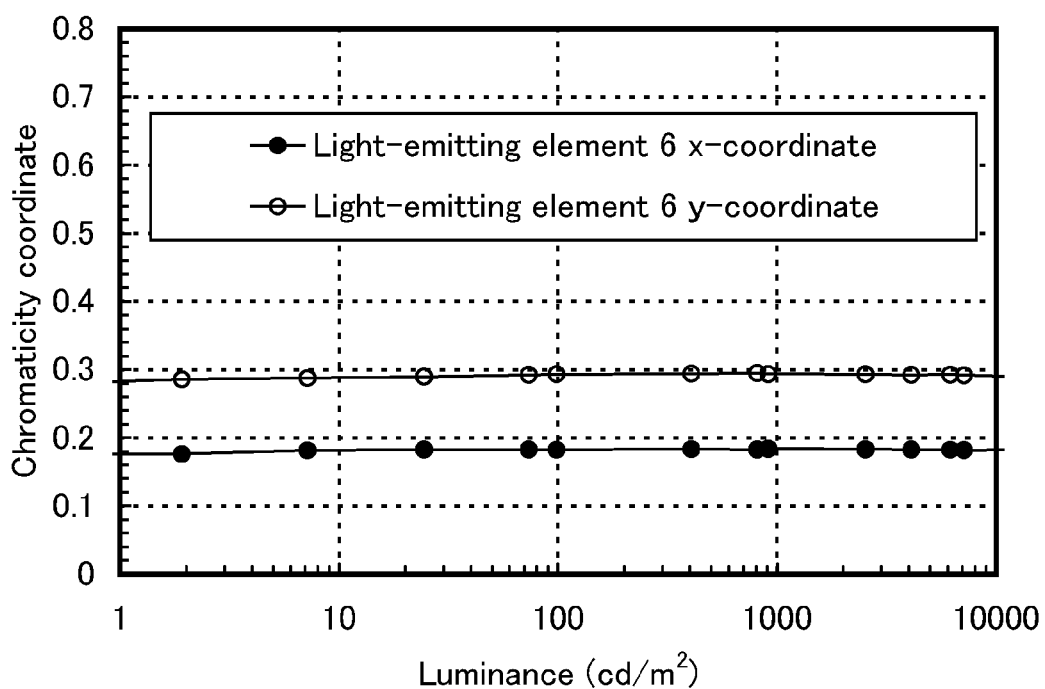
FIG. 27 shows luminance-chromaticity coordinate characteristics of the light-emitting element in Example 7.
Figure 28:
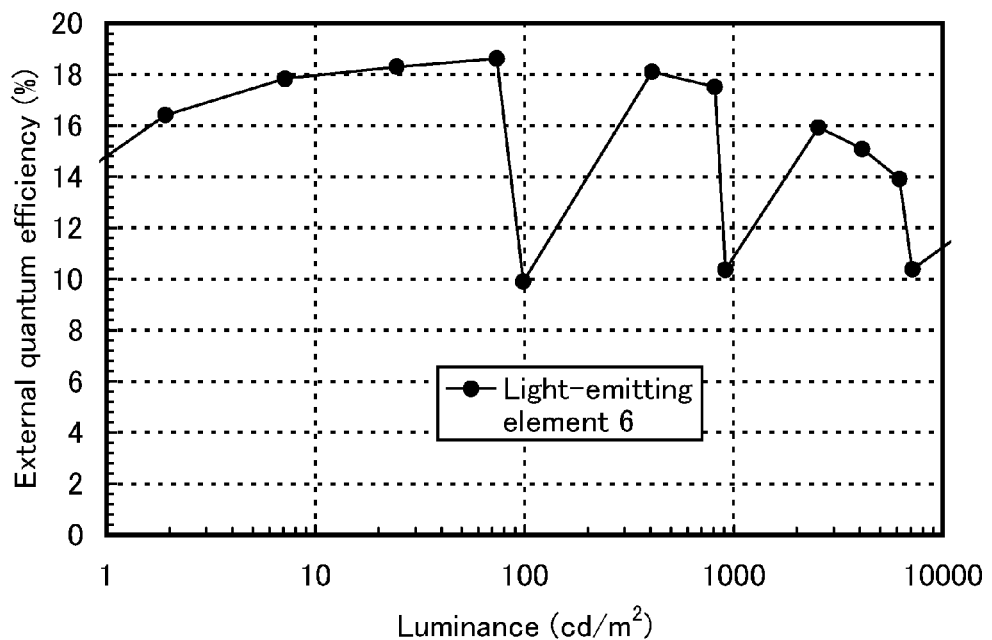
FIG. 28 shows luminance-external quantum efficiency characteristic of the light-emitting element in Example 7.
Figure 29:
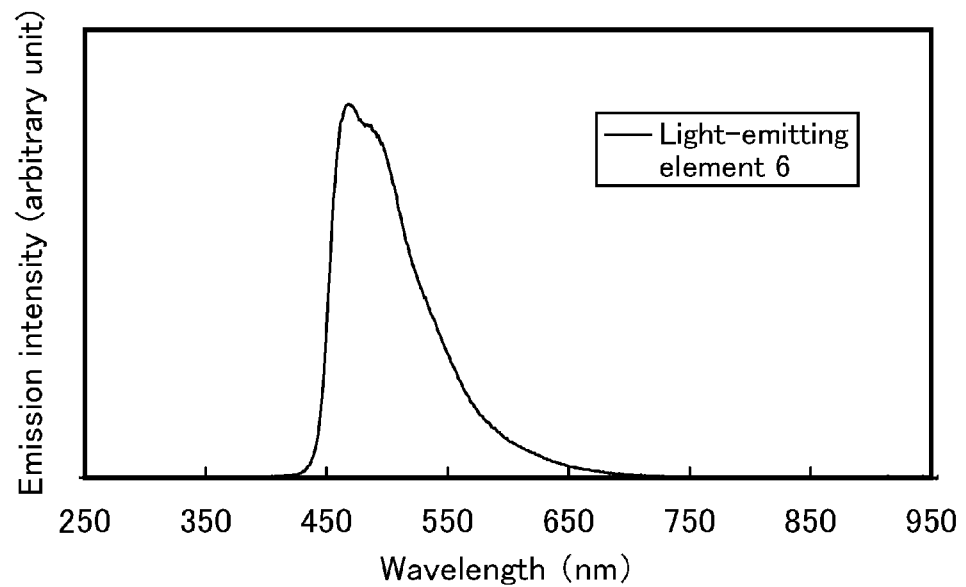
FIG. 29 shows an emission spectrum of the light-emitting element in Example 7.

FIG. 26 shows the luminance-current efficiency characteristics of the light-emitting element 6. In FIG. 26, the horizontal axis represents luminance (cd/m$^2$) and the vertical axis represents current efficiency (cd/A). FIG. 27 shows the luminance-chromaticity coordinate characteristics of the light-emitting element 6. In FIG. 27, the horizontal axis represents luminance (cd/m$^2$) and the vertical axis represents chromaticity coordinate (the x-coordinate and the y-coordinate). FIG. 28 shows the luminance-external quantum efficiency characteristics of the light-emitting element 6. In FIG. 28, the horizontal axis represents luminance (cd/m$^2$) and the vertical axis represents external quantum efficiency (%). FIG. 29 shows the emission spectrum of the light-emitting element 6. In FIG. 29, the horizontal axis represents wavelength (nm) and the vertical axis represents emission intensity (arbitrary unit). Table 9 shows the voltage (V), CIE chromaticity coordinate (x, y), current efficiency (cd/A), and external quantum efficiency (%) of the light-emitting element 6 at a luminance of 800 cd/m$^2$.

TABLE 9

| | Voltage (V) | Chromaticity (x, y) | Current efficiency (cd/A) | External quantum efficiency (%) |
|---|---|---|---|---|
| Light-emitting element 6 | 6.6 | (0.18, 0.29) | 35 | 18 |

The CIE chromaticity coordinate of the light-emitting element 6 at a luminance of 800 cd/m$^2$ is (x, y)=(0.18, 0.29). This result shows that blue light emission originating from [Ir(Mptz1-mp)$_3$] is obtained from the light-emitting element 6.

Further, mBP22 PSi was found to have a high T1 level and can be used as a host material in which a light-emitting material (guest material) which emits visible light (phosphorescence or fluorescence) is dispersed.

FIG. 26 and FIG. 28 show that the light-emitting element 6 has high emission efficiency.

FIG. 27 shows that almost no change in color is observed in the range of low luminance to high luminance in the light-emitting element 6. It can be said from this result that the light-emitting element 6 has excellent carrier balance.

Figure 30:
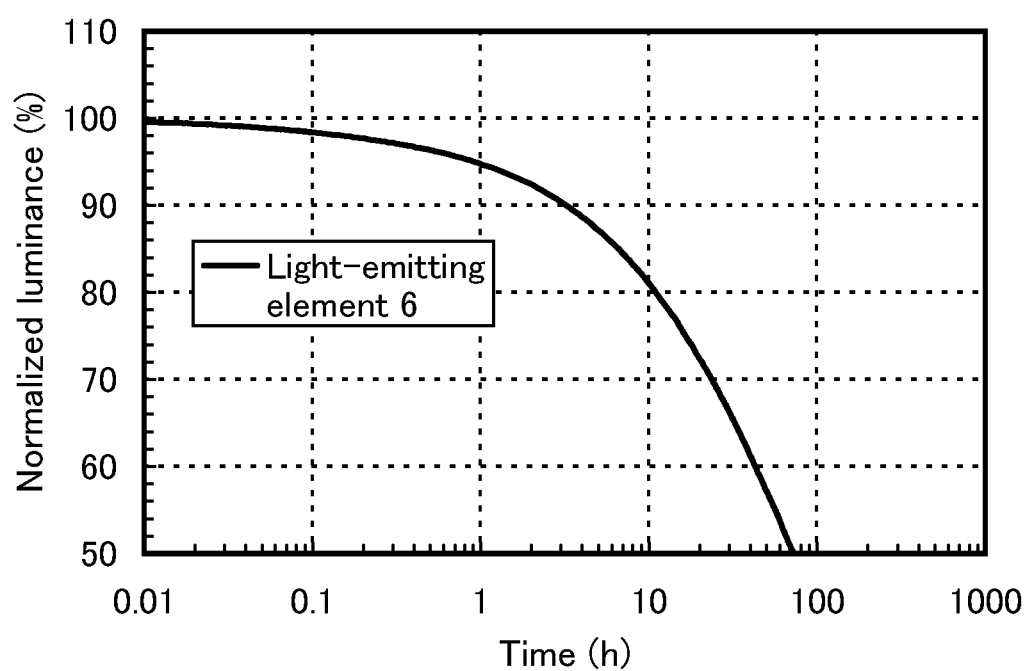
FIG. 30 shows results of a reliability test of the light-emitting element in Example 7.

Next, the light-emitting element 6 was subjected to a reliability test. FIG. 30 shows results of the reliability test. In FIG. 30, the vertical axis represents normalized luminance (%) on the assumption that the initial luminance is 100%, and the horizontal axis represents driving time (h) of the element.

In the reliability test, the light-emitting element of this example was driven under the conditions where the initial luminance was 300 cd/m$^2$ and the current density was constant.

According to FIG. 30, the light-emitting element 6 kept 50% of the initial luminance after 72-hour driving.

Since a phosphorescent substance which exhibits blue emission or a host material which is used together with the phosphorescent substance has a high T1 level, the phosphorescent substance or the host material is likely to have a wide band gap and a low HOMO level. Thus, it is difficult to inject holes to the light-emitting substance, and an increase in driving voltage or a reduction in lifetime easily occurs. The organic compound (here, mBP22 PSi) used for the composite material of one embodiment of the present invention has a low HOMO level. The use of the composite material of one embodiment of the present invention for a hole-injection layer makes it possible to efficiently inject holes into a hole-transport layer. In particular, when mBP22 PSi is used for a hole-injection layer (as an organic compound included in a composite material) and a hole-transport layer, and as a host material for a light-emitting layer, holes can be efficiently injected from the first electrode to the light-emitting layer. In addition, the same materials can be used in a plurality of layers; thus, an increase in synthesis cost can be suppressed. As described in this example, the composite material of one embodiment of the present invention can be suitably used for an element which emits blue phosphorescence. With the use of the composite material of one embodiment of the present invention, it is possible to achieve a light-emitting element in which an increase in driving voltage and a reduction in lifetime are suppressed.

Example 8

In this example, light-emitting elements each of which is one embodiment of the present invention will be described with reference to FIG. 18B. Shown below are structural formulae of materials used in this example. Note that the structural formulae of the materials used in the above example are omitted here.

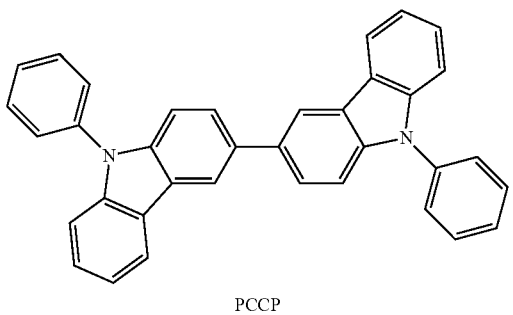

PCCP

Methods of manufacturing light-emitting elements 7 to 9 of this example will be described below.

(Light-Emitting Element 7)

The light-emitting element 7 was manufactured using the same materials and methods under the same conditions as the light-emitting element 6 of Example 7 except for a hole-transport layer 1112.

The hole-transport layer 1112 of the light-emitting element 7 was formed by forming a film of mCP to a thickness of 20 nm.

(Light-Emitting Element 8)

The light-emitting element 8 was manufactured using the same materials and methods under the same conditions as the light-emitting element 7 except for a first light-emitting layer 1113a.

The first light-emitting layer 1113a of the light-emitting element 8 was formed by co-evaporation of mBP22 PSi, 9-phenyl-9H-3-(9-phenyl-9H-carbazol-3-yl)carbazole (abbreviation: PCCP), and [Ir(Mptz1-mp)$_3$]. The mass ratio of mBP22 PSi to PCCP and [Ir(Mptz1-mp)$_3$] were adjusted to 1:0.25:0.06 (=mBP22 PSi: PCCP: [Ir(Mptz1-mp)$_3$]). The thickness of the first light-emitting layer 1113a was set to 30 nm.

(Light-Emitting Element 9)

The light-emitting element 9 was manufactured using the same materials and methods under the same conditions as the light-emitting element 8 except for an electron-transport layer 1114.

The electron-transport layer 1114 of the light-emitting element 9 was formed by forming a film of mDBTBIm-II to a thickness of 15 nm.

Table 10 shows the element structures of the light-emitting elements 7 to 9 obtained as described above.

In a glove box containing a nitrogen atmosphere, these light-emitting elements were sealed so as not to be exposed to the air. Then, operation characteristics of these light-emitting elements were measured. Note that the measurement was carried out at room temperature (in an atmosphere kept at 25° C.).

Figure 31:
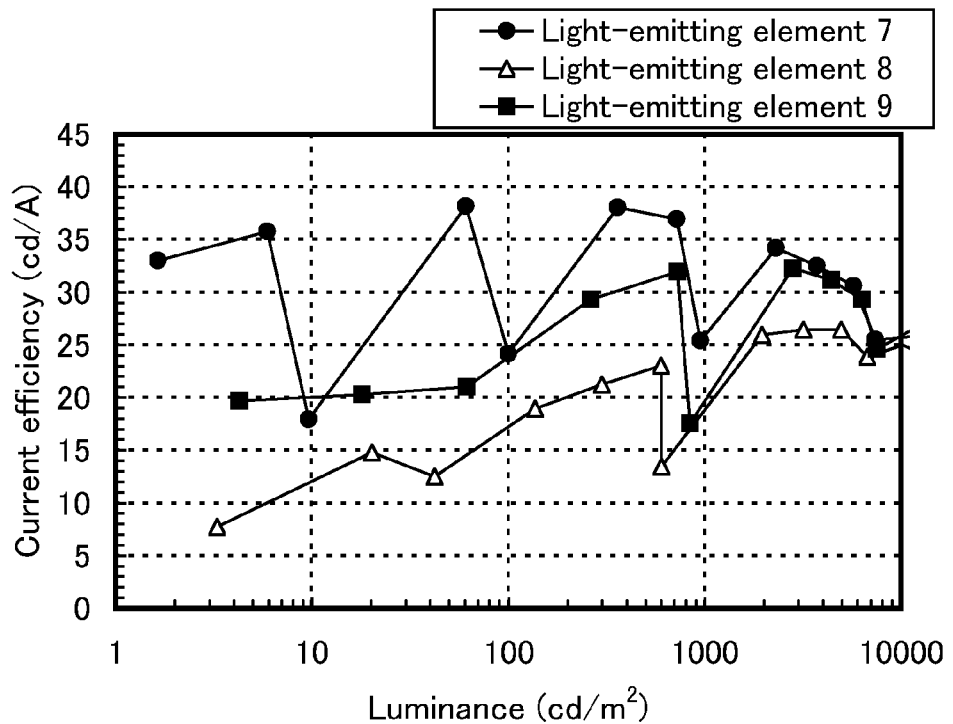
FIG. 31 shows luminance-current efficiency characteristics of light-emitting elements in Example 8.
Figure 32:
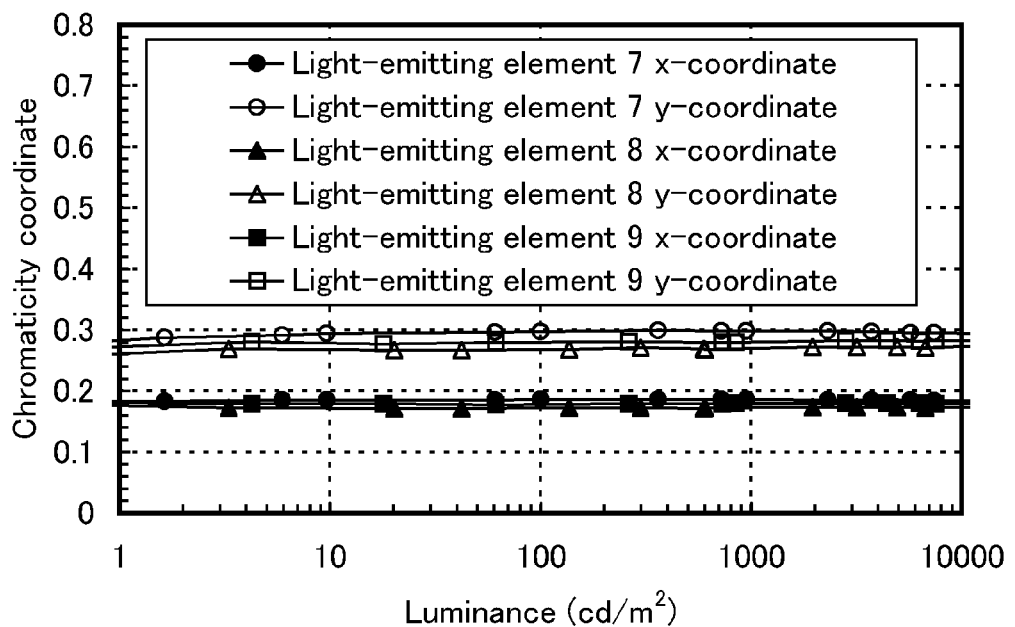
FIG. 32 shows luminance-chromaticity coordinate characteristics of the light-emitting elements in Example 8.
Figure 33:
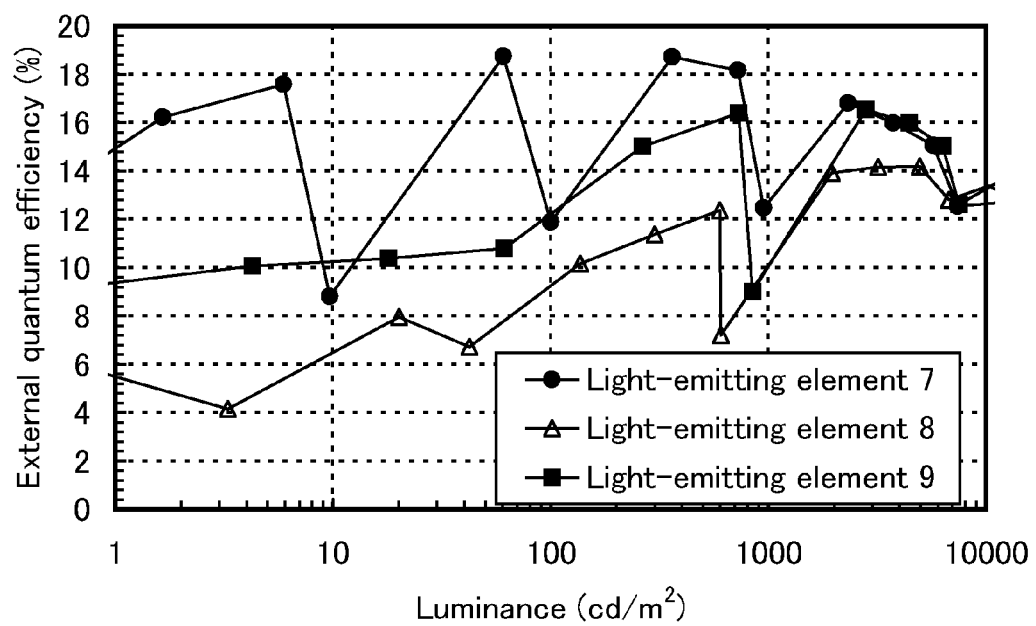
FIG. 33 shows luminance-external quantum efficiency characteristic of the light emitting elements in Example 8.
Figure 34:
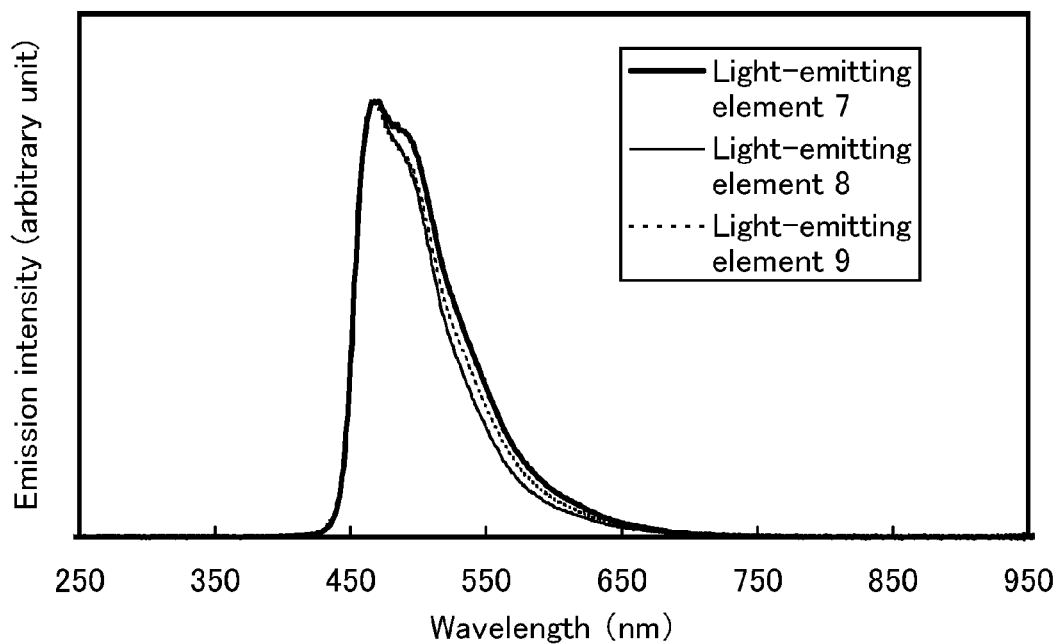
FIG. 34 shows emission spectra of the light-emitting elements in Example 8.

FIG. 31 shows the luminance-current efficiency characteristics of the light-emitting elements 7 to 9. In FIG. 31, the horizontal axis represents luminance (cd/m$^2$) and the vertical axis represents current efficiency (cd/A). FIG. 32 shows the luminance-chromaticity coordinate characteristics of the light-emitting elements 7 to 9. In FIG. 32, the horizontal axis represents luminance (cd/m$^2$) and the vertical axis represents chromaticity coordinate (the x-coordinate and the y-coordinate). FIG. 33 shows the luminance-external quantum efficiency characteristics of the light-emitting elements 7 to 9. In FIG. 33, the horizontal axis represents luminance (cd/m$^2$) and the vertical axis represents external quantum efficiency (%). FIG. 34 shows the emission spectra of the light-emitting elements 7 to 9. In FIG. 34, the horizontal axis represents wavelength (nm) and the vertical axis represents emission intensity (arbitrary unit). Table 11 shows the voltage (V), CIE chromaticity coordinate (x, y), current efficiency (cd/A), and external quantum efficiency (%) of each of the light-emitting elements 7 to 9 at a luminance of about 700 cd/m$^2$.

TABLE 11

|  | Voltage (V) | Chromaticity (x, y) | Current efficiency (cd/A) | External quantum efficiency (%) |
| --- | --- | --- | --- | --- |
| Light-emitting element 7 | 6.0 | (0.19, 0.30) | 37 | 18 |
| Light-emitting element 8 | 5.1 | (0.17, 0.27) | 23 | 12 |
| Light-emitting element 9 | 4.5 | (0.18, 0.28) | 32 | 16 |

The CIE chromaticity coordinates of the light-emitting element 7, the light-emitting element 8, and the light-emitting element 9 are, respectively, (x, y)=(0.19, 0.30), (x, y)=(0.17, 0.27), and (x, y)=(0.18, 0.28) at a luminance of about 700 cd/m$^2$. These results show that blue light emission originating from [Ir(Mptz1-mp)$_3$] is obtained from each of the light-emitting elements 7 to 9.

FIG. 31 and FIG. 33 show that the light-emitting elements 7 to 9 each have high emission efficiency.

TABLE 10

| | First electrode | Hole-injection layer | Hole-transport layer | First light-emitting layer | Second light-emitting layer | Electron-transport layer | Electron-injection layer | Second electrode |
| --- | --- | --- | --- | --- | --- | --- | --- | --- |
| Light-emitting element 7 | ITSO 110 nm | mBP22PSi:MoOx (=4:2) 60 nm | mCP 20 nm | mBP22PSi: [Ir(Mptz1-mp)$_3$] (=1:0.06) 30 nm | mDBTBIm-II: [Ir(Mptz1-mp)$_3$] (=1:0.06) 10 nm | BPhen 15 nm | LiF 1 nm | Al 200 nm |
| Light-emitting element 8 | ITSO 110 nm | mBP22PSi:MoOx (=4:2) 60 nm | mCP 20 nm | mBP22PSi:PCCP: [Ir(Mptz1-mp)$_3$] (=1:0.25:0.06) 30 nm | mDBTBIm-II: [Ir(Mptz1-mp)$_3$] (=1:0.06) 10 nm | BPhen 15 nm | LiF 1 nm | Al 200 nm |
| Light-emitting element 9 | ITSO 110 nm | mBP22PSi:MoOx (=4:2) 60 nm | mCP 20 nm | mBP22PSi:PCCP: [Ir(Mptz1-mp)$_3$] (=1:0.25:0.06) 30 nm | mDBTBIm-II: [Ir(Mptz1-mp)$_3$] (=1:0.06) 10 nm | mDBTBIm-II 15 nm | LiF 1 nm | Al 200 nm |

FIG. 32 shows that almost no change in color is observed in the range of low luminance to high luminance in each of the light-emitting elements 7 to 9. It can be said from this result that the light-emitting elements 7 to 9 each have excellent carrier balance.

Table 11 shows that the driving voltage of the light-emitting elements 8 and 9 is lower than that of the light-emitting element 7. This is probably because PCCP which has a high hole-transport property is contained in the first light-emitting layer of each of the light-emitting elements 8 and 9, so that holes are efficiently injected into the first light-emitting layer.

The organic compound (here, mBP22 PSi) used for the hole-injection layer is contained in the first light-emitting layer, so that holes can be efficiently injected from the first electrode to the first light-emitting layer. Further, when an auxiliary dopant material (here, PCCP) having a HOMO level which is relatively close to the HOMO level of a light-emitting material (guest material, here, [Ir(Mptz1-mp)$_3$]) and having a high hole-transport property is contained in the first light-emitting layer, so that a light-emitting element with low driving voltage can be achieved. Specifically, the difference in HOMO level between the guest material and the auxiliary dopant material is preferably within 0.2 eV.

Table 11 also shows that the current efficiency of the light-emitting element 7 is higher than those of the light-emitting elements 8 and 9. This is probably because the T1 level of mBP22 PSi that is the organic compound of one embodiment of the present invention is high and the excitation energy generated in the first light-emitting layer is efficiently transferred to [Ir(Mptz1-mp)$_3$]. Loss of carriers is suppressed and the probability of recombination is increased probably for the following reason: mBP22 PSi that is the organic compound of one embodiment of the present invention has a high LUMO level (the absolute value is small) and a low HOMO level (the absolute value is large); thus, carriers (holes and electrons) injected into the first light-emitting layer are trapped therein and efficiently transferred to [Ir(Mptz1-mp)$_3$].

Figure 35:
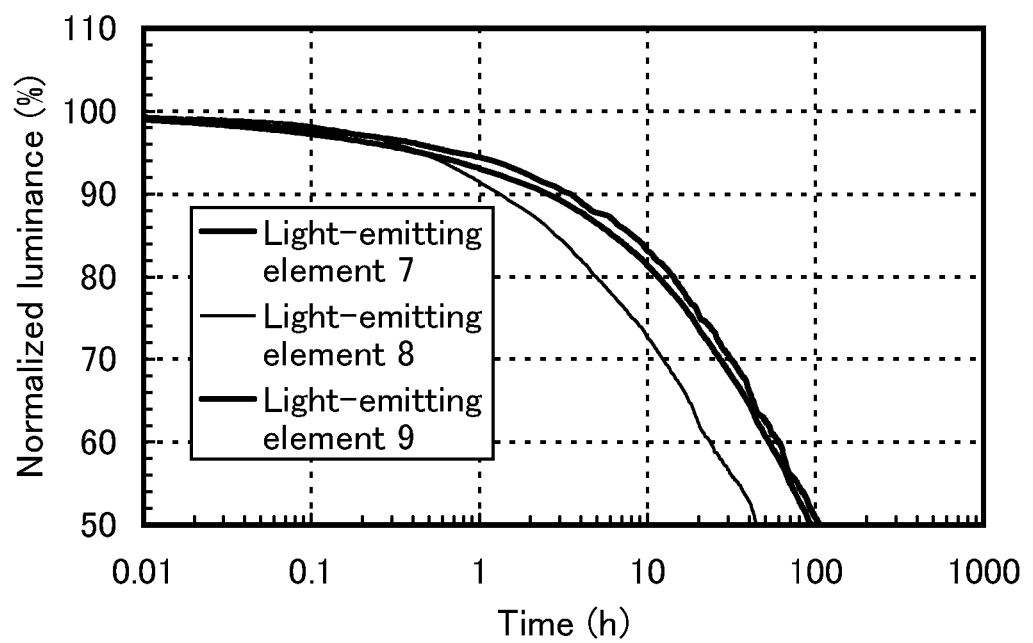
FIG. 35 shows results of reliability tests of the light-emitting elements in Example 8.

Next, the light-emitting elements 7 to 9 were subjected to reliability tests. FIG. 35 shows results of the reliability tests. In FIG. 35, the vertical axis represents normalized luminance (%) on the assumption that the initial luminance is 100%, and the horizontal axis represents driving time (h) of the light-emitting elements.

In the reliability tests, the light-emitting elements of this example were driven under the conditions where the initial luminance was 300 cd/m$^2$ and the current density was constant.

According to FIG. 35, the light-emitting element 7 kept 50% of the initial luminance after 93-hour driving, the light-emitting element 8 kept 50% of the initial luminance after 44-hour driving, and the light-emitting element 9 kept 50% of the initial luminance after 110-hour driving.

Since a phosphorescent substance which exhibits blue emission or a host material which is used together with the phosphorescent substance has a high T1 level, the phosphorescent substance or the host material is likely to have a wide band gap and a low HOMO level. Thus, it is difficult to inject holes to the light-emitting substance, and an increase in driving voltage or a reduction in lifetime easily occurs. The organic compound (here, mBP22 PSi) used for the composite material of one embodiment of the present invention has a low HOMO level. The use of the composite material of one embodiment of the present invention for a hole-injection layer makes it possible to efficiently inject holes into a hole-transport layer. In particular, when mBP22 PSi is used for a hole-injection layer (as an organic compound included in a composite material) and a hole-transport layer, and as a host material for a light-emitting layer, holes can be efficiently injected into the light-emitting layer. As described in this example, the composite material of one embodiment of the present invention can be used for an element which emits blue phosphorescence. With the use of the composite material of one embodiment of the present invention, it is possible to achieve a light-emitting element in which an increase in driving voltage and a reduction in lifetime are suppressed.

Example 9

In this example, a light-emitting element of one embodiment of the present invention will be described with reference to FIG. 18A. Shown below are structural formulae of materials used in this example. Note that the structural formulae of the materials used in the above examples are omitted here.

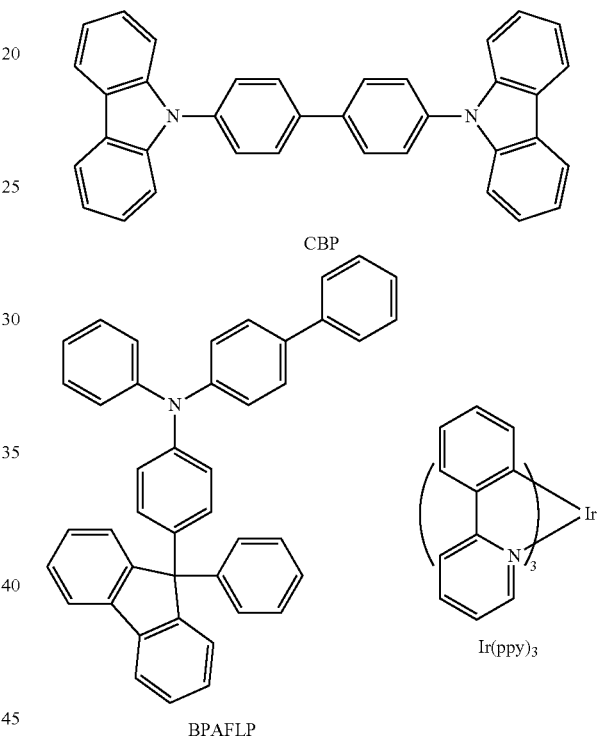

CBP

BPAFLP

Ir(ppy)$_3$

A method of manufacturing a light-emitting element 10 of this example will be described below.

(Light-Emitting Element 10)

First, a film of ITSO was formed over a glass substrate 1100 by a sputtering method to form a first electrode 1101 serving as an anode. The thickness of the first electrode 1101 was set to 110 nm, and the area thereof was set to 2 mm×2 mm.

In pretreatment for forming the light-emitting element on the substrate 1100, UV ozone treatment was performed for 370 seconds after washing of a surface of the substrate with water and baking performed at 200° C. for one hour.

After that, the substrate 1100 was transferred into a vacuum evaporation apparatus where the pressure had been reduced to approximately 10$^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed on a substrate holder in the vacuum evaporation apparatus so that a surface on which the first electrode 1101 was provided faced downward. The pressure in the vacuum evaporation apparatus was reduced to about $10^{-4}$ Pa. Then, 4,4'-di(N-carbazolyl)biphenyl (abbreviation: CBP) and molybdenum(VI) oxide were co-evaporated to form a hole-injection layer 1111 on the first electrode 1101. The thickness of the hole-injection layer 1111 was set to 60 nm. The mass ratio of CBP to molybdenum oxide was adjusted to 4:2 (=CBP: molybdenum oxide).

Next, a film of 4-phenyl-4'-(9-phenylfluoren-9-yl)triphenylamine (abbreviation: BPAFLP) was formed to a thickness of 20 nm on the hole-injection layer 1111 to form a hole-transport layer 1112.

Furthermore, on the hole-transport layer 1112, mBP22 PSi and tris(2-phenylpyridinato-N,C$^{2'}$)iridium(III) (abbreviation: [Ir(ppy)$_3$]) were co-evaporated to form a light-emitting layer 1113. Here, the mass ratio of mBP22 PSi to [Ir(ppy)$_3$] was adjusted to 1:0.06 (=mBP22 PSi: [Ir(ppy)$_3$]). The thickness of the light-emitting layer 1113 was set to 40 nm.

Next, on the light-emitting layer 1113, a film of mDBT-BIm-II was formed to a thickness of 15 nm to form a first electron-transport layer 1114a.

Then, on the first electron-transport layer 1114a, a film of BPhen was formed to a thickness of 20 nm to form a second electron-transport layer 1114b.

Furthermore, on the second electron-transport layer 1114b, a film of LiF was formed to a thickness of 1 nm by evaporation to form an electron-injection layer 1115.

Lastly, a film of aluminum was formed to a thickness of 200 nm by evaporation to form a second electrode 1103 serving as a cathode. Through the above steps, the light-emitting element 10 of this example was manufactured.

Note that in all the above evaporation steps, evaporation was performed by a resistance-heating method.

Table 12 shows the element structure of the light-emitting element 10 obtained as described above.

TABLE 12

| | First electrode | Hole-injection layer | Hole-transport layer | Light-emitting layer | First electron-transport layer | Second electron-transport layer | Electron-injection layer | Second electrode |
|---|---|---|---|---|---|---|---|---|
| Light-emitting element 10 | ITSO 110 nm | CBP:MoOx (=4:2) 60 nm | BPAFLP 20 nm | mBP22PSi: [Ir(ppy)$_3$] (=1:0.06) 40 nm | mDBTBIm-II 15 nm | BPhen 20 nm | LiF 1 nm | Al 200 nm |

In a glove box containing a nitrogen atmosphere, the light-emitting element 10 was sealed so as not to be exposed to the air. Then, operation characteristics of the light-emitting element 10 were measured. Note that the measurement was carried out at room temperature (in an atmosphere kept at 25° C.).

Figure 36:
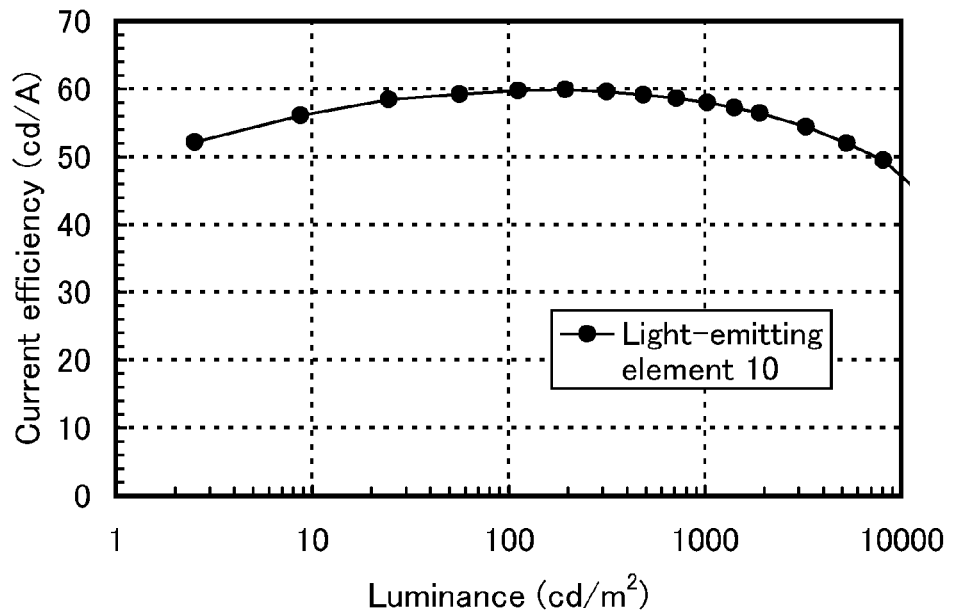
FIG. 36 shows luminance-current efficiency characteristics of a light-emitting element in Example 9.
Figure 37:
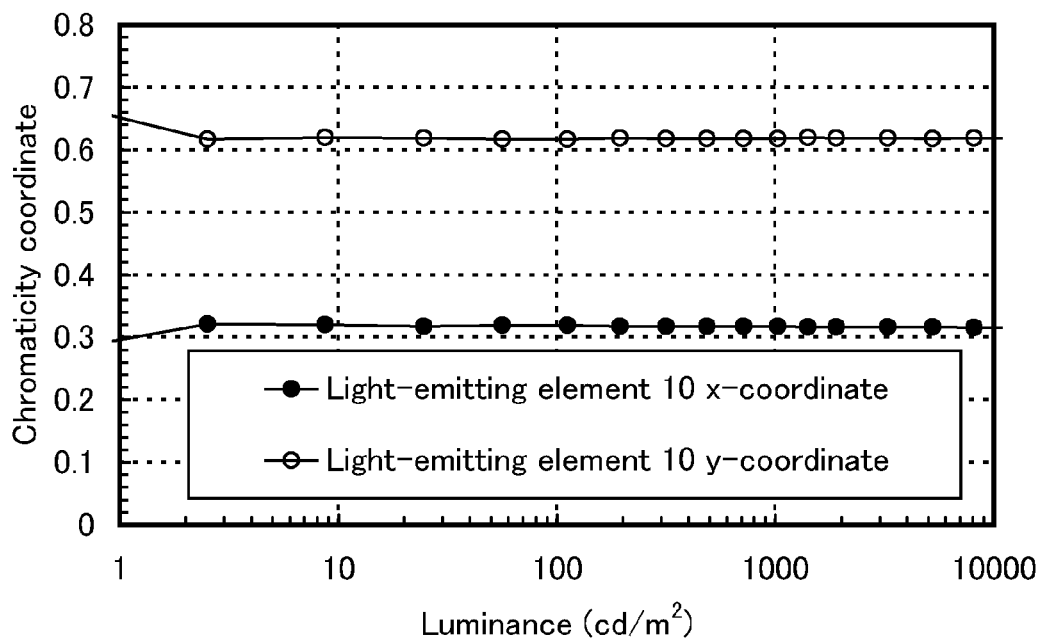
FIG. 37 shows luminance-chromaticity coordinate characteristics of the light-emitting element in Example 9.
Figure 38:
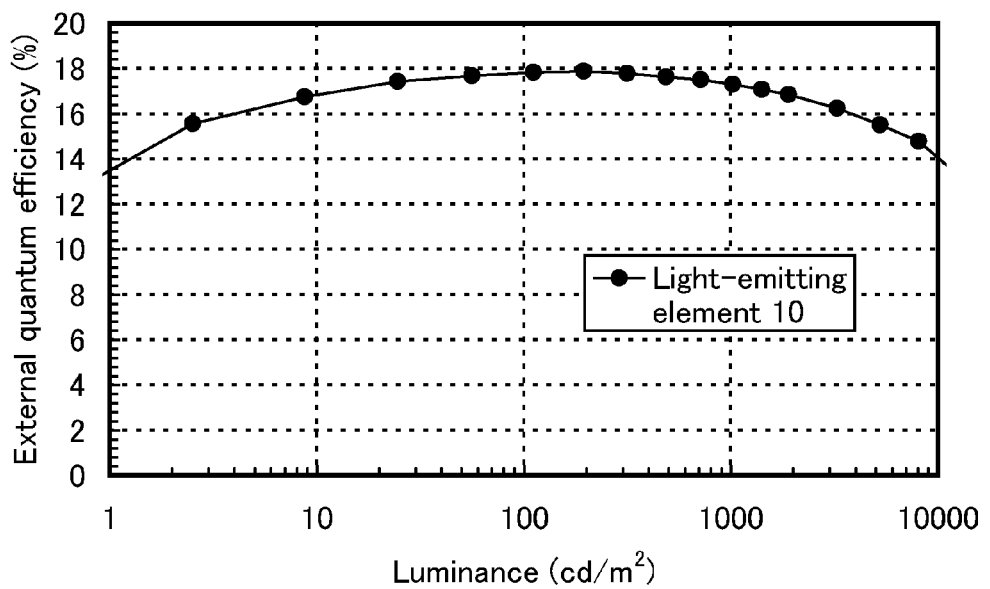
FIG. 38 shows luminance-external quantum efficiency characteristics of the light-emitting element in Example 9.
Figure 39:
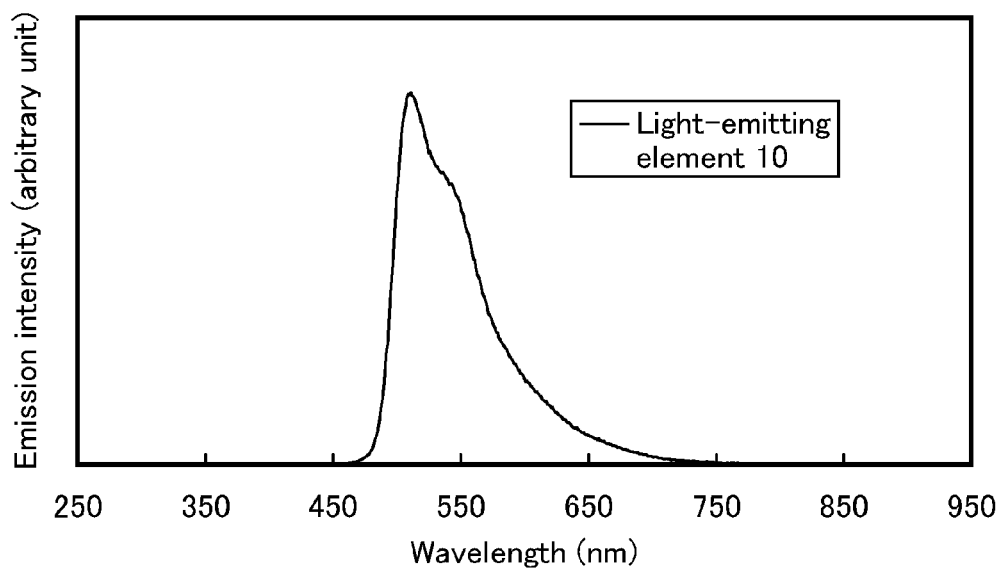
FIG. 39 shows an emission spectrum of the light-emitting element in Example 9.

FIG. 36 shows the luminance-current efficiency characteristics of the light-emitting element 10. In FIG. 36, the horizontal axis represents luminance (cd/m$^2$) and the vertical axis represents current efficiency (cd/A). FIG. 37 shows the luminance-chromaticity coordinate characteristics of the light-emitting element 10. In FIG. 37, the horizontal axis represents luminance (cd/m$^2$) and the vertical axis represents chromaticity coordinate (the x-coordinate and the y-coordinate). FIG. 38 shows the luminance-external quantum efficiency characteristics of the light-emitting element 10. In FIG. 38, the horizontal axis represents luminance (cd/m$^2$) and the vertical axis represents external quantum efficiency (%). FIG. 39 shows the emission spectrum of the light-emitting element 10. In FIG. 39, the horizontal axis represents wavelength (nm) and the vertical axis represents emission intensity (arbitrary unit). Further, Table 13 shows the voltage (V), CIE chromaticity coordinate (x, y), current efficiency (cd/A), and external quantum efficiency (%) of the light-emitting element 10 at a luminance of 1000 cd/m$^2$.

TABLE 13

| | Voltage (V) | Chromaticity (x, y) | Current efficiency (cd/A) | External quantum efficiency (%) |
|---|---|---|---|---|
| Light-emitting element 10 | 5.2 | (0.32, 0.62) | 58 | 17 |

As shown in Table 13, the CIE chromaticity coordinate of the light-emitting element 10 is (x, y)=(0.32, 0.62) at a luminance of 1000 cd/m$^2$. This result shows that green light emission originating from [Ir(ppy)$_3$] is obtained from the light-emitting element 10.

Further, mBP22 PSi was found to have a high T1 level and can be used as a host material in which a light-emitting material emitting phosphorescence with a longer wavelength than green light and a light-emitting material emitting fluorescence in the visible light region (guest material) are dispersed.

FIG. 36 and FIG. 38 show that the light-emitting element 10 has high emission efficiency.

FIG. 37 shows that almost no change in color is observed in the range of low luminance to high luminance in the light-emitting element 10. It can be said from this result that the light-emitting element 10 has excellent carrier balance.

Figure 40:
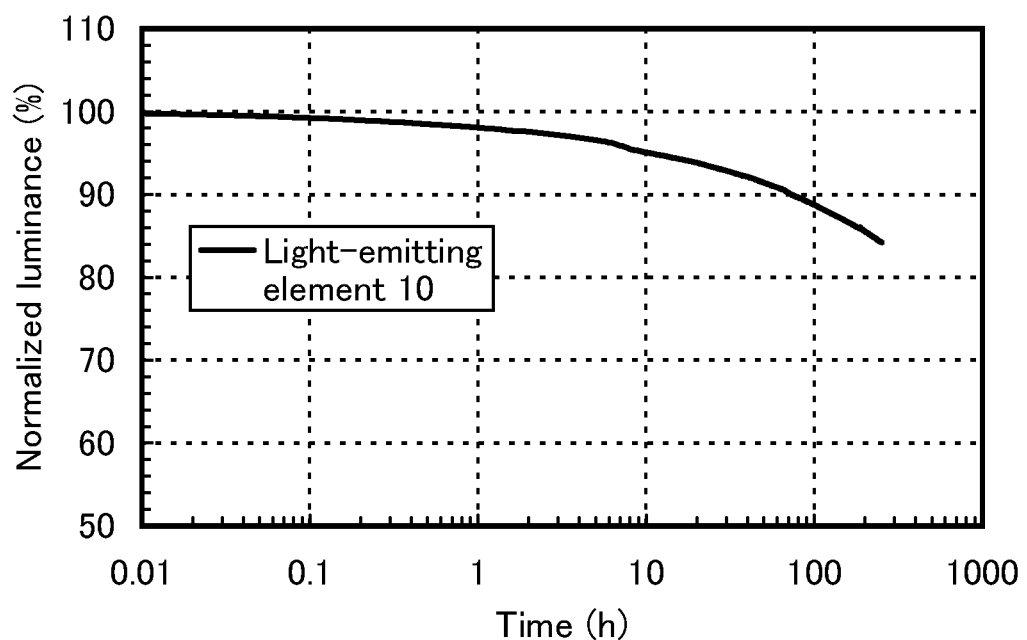
FIG. 40 shows results of a reliability test of the light-emitting element in Example 9.

Next, the light-emitting element 10 was subjected to a reliability test. FIG. 40 shows results of the reliability test. In FIG. 40, the vertical axis represents normalized luminance (%) on the assumption that the initial luminance is 100%, and the horizontal axis represents driving time (h) of the light-emitting element.

In the reliability test, the light-emitting element 10 was driven under the conditions where the initial luminance was 1000 cd/m$^2$ and the current density was constant.

FIG. 40 shows that the luminance of the light-emitting element 10 after 250-hour driving was 84% of the initial luminance.

The above results show that mBP22 PSi that is the organic compound of one embodiment of the present invention can be suitably used also as a host material for a light-emitting layer.

Reference Example 1

A synthesis example of tris[3-methyl-1-(2-methylphenyl)-5-phenyl-1H-1,2,4-tri azolato]iridium(III) (abbreviation: [Ir(Mptz1-mp)$_3$]), which was used in the above examples, will be described.

Step 1: Synthesis of N-(1-ethoxyethylidene)benzamide

First, into a 500-mL three-neck flask were put 15.5 g of ethyl acetimidate hydrochloride, 150 mL of toluene, and 31.9 g of triethylamine (Et₃N), and the mixture was stirred at room temperature for 10 minutes. With a 50-mL dropping funnel, a mixed solution of 17.7 g of benzoyl chloride and 30 mL of toluene were added dropwise to this mixture, and the mixture was stirred at room temperature for 24 hours. After a predetermined time elapsed, the reaction mixture was suction-filtered, and the solid was washed with toluene. The obtained filtrate was concentrated to give N-(1-ethoxyethylidene)benzamide (red oily substance, 82% yield). Shown below is the synthesis scheme of Step 1.

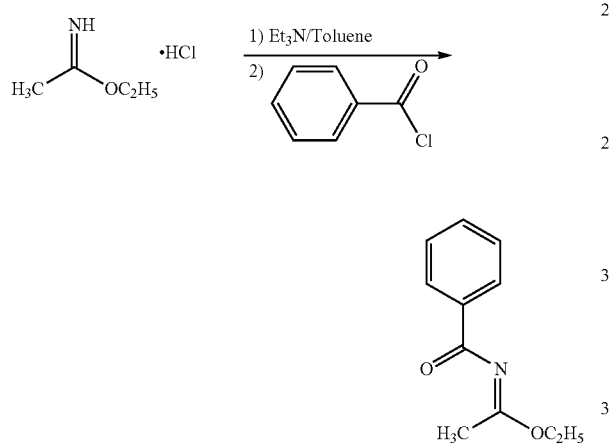

Step 2: Synthesis of 3-methyl-1-(2-methylphenyl)-5-phenyl-1H-1,2,4-triazole (Abbreviation: HMptz1-mp)

Next, in a 300-mL recovery flask were put 8.68 g of o-tolyl hydrazine hydrochloride, 100 mL of carbon tetrachloride, and 35 mL of triethylamine (Et₃N), and the mixture was stirred at room temperature for one hour. After a predetermined time elapsed, 8.72 g of N-(1-ethoxyethylidene)benzamide obtained in the above Step 1 was added to this mixture, and the mixture was stirred at room temperature for 24 hours. After a predetermined time elapsed, water was added to the reaction mixture, and organic substances were extracted from the aqueous layer with chloroform. The obtained solution of the extract and the organic layer were washed with saturated saline, and anhydrate magnesium sulfate was added thereto for drying. The obtained mixture was gravity-filtered, and the filtrate was condensed to give an oily substance. The given oily substance was purified by silica gel column chromatography. As a developing solvent, dichloromethane was used. The obtained fraction was concentrated to give 3-methyl-1-(2-methylphenyl)-5-phenyl-1H-1,2,4-triazole (abbreviation: HMptz1-mp) (orange oily substance, 84% yield). Shown below is the synthesis scheme of Step 2.

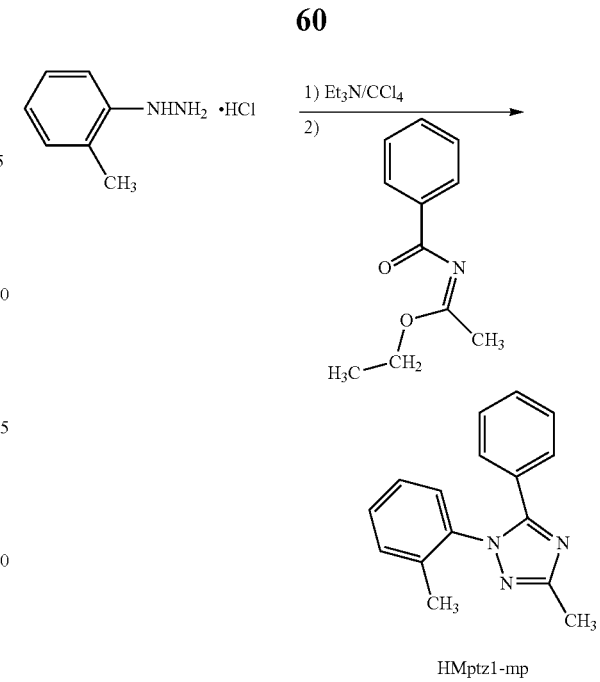

Step 3: tris[3-methyl-1-(2-methylphenyl)-5-phenyl-1H-1,2,4-triazolato]iridium(III) (Abbreviation: [Ir(Mptz1-mp)₃])

Next, 2.71 g of the ligand HMptz1-mp obtained in the above Step 2 and 1.06 g of tris(acetylacetonato)iridium(III) were put into a reaction container provided with a three-way cock. The atmosphere in the reaction container was replaced with argon, and the mixture was heated at 250° C. for 48 hours to be reacted. This reaction mixture was dissolved in dichloromethane and purified by silica gel column chromatography. As a developing solvent, dichloromethane was first used, and a mixed solvent of dichloromethane and ethyl acetate in a volume ratio of 10:1 was then used. The obtained fraction was concentrated to obtain a solid. This solid was washed with ethyl acetate, and recrystallized from a mixed solvent of dichloromethane and ethyl acetate to give an organometallic complex, [Ir(Mptz1-mp)₃], (yellow powder, 35% yield). Shown below is the synthesis scheme of Step 3.

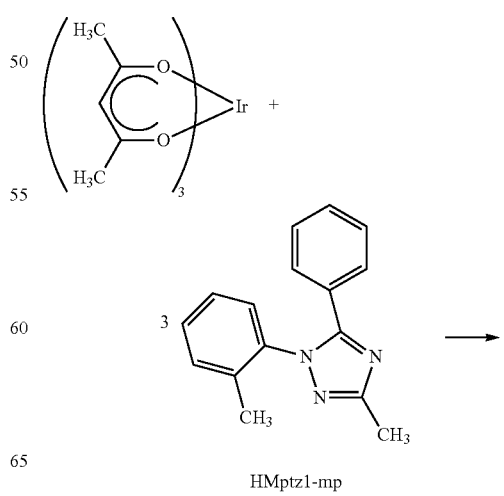

-continued

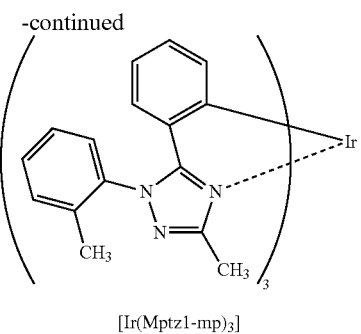

[Ir(Mptz1-mp)₃]

Analysis results by nuclear magnetic resonance spectroscopy ($^1$H NMR) of the yellow powder obtained in Step 3 are described below. The results show that [Ir(Mptz1-mp)₃] was obtained.

$^1$H NMR data of the obtained substance are as follows: $^1$H NMR. δ (CDCl₃): 1.94-2.21 (m, 18H), 6.47-6.76 (m, 12H), 7.29-7.52 (m, 12H).

This application is based on Japanese Patent Application serial no. 2011-151536 filed with Japan Patent Office on Jul. 8, 2011, the entire contents of which are hereby incorporated by reference.

What is claimed is:

1. A composite material comprising:
   an organic compound; and
   an inorganic compound exhibiting an electron-accepting property with respect to the organic compound,
   wherein rings of the organic compound are all benzene rings,
   wherein the number of the benzene rings of the organic compound is greater than or equal to 4 and less than or equal to 25,
   wherein the organic compound includes benzene rings cross-linked with silicon, and
   wherein at least two benzene rings of the benzene rings are linked by a single bond at an ortho position or a meta position.

2. The composite material according to claim 1, wherein the inorganic compound is a transition metal oxide.

3. The composite material according to claim 2, wherein the transition metal oxide is one or more selected from the group consisting of titanium oxide, vanadium oxide, tantalum oxide, molybdenum oxide, tungsten oxide, rhenium oxide, ruthenium oxide, chromium oxide, zirconium oxide, hafnium oxide, and silver oxide.

4. The composite material according to claim 1, wherein the organic compound includes an alkyl group having 1 to 6 carbon atoms as a substituent.

5. The composite material according to claim 1, wherein a measurement value of a highest occupied molecular orbital level of the organic compound by photoelectron spectroscopy is less than or equal to −5.7 eV.

6. A light-emitting element comprising:
   a pair of electrodes; and
   a layer containing the composite material according to claim 1 between the pair of electrodes.

7. The light-emitting element according to claim 6, wherein the layer is in contact with one of the pair of electrodes,
   wherein the layer is in contact with a second layer containing an organic compound whose rings are all benzene rings, and the number of the benzene rings is greater than or equal to 4 and less than or equal to 25, or
   wherein the layer is in contact with a light-emitting layer containing a first organic compound whose rings are all benzene rings and a second organic compound dispersed in the first organic compound, and the number of the benzene rings is greater than or equal to 4 and less than or equal to 25.

8. A light-emitting device comprising the light-emitting element according to claim 6 in a display portion or in a light-emitting portion.

9. A light-emitting element comprising:
   a layer between a pair of electrodes, wherein the layer comprises a first layer comprising a first light-emitting substance to an n-th layer comprising an n-th light-emitting substance (n is a natural number greater than or equal to 2); and
   a layer containing the composite material according to claim 1 between the k-th layer comprising the k-th light-emitting substance and the (k+1)-th layer comprising the (k+1)-th light-emitting substance (k is a natural number greater than or equal to 1 and less than n).

10. The composite material according to claim 1, wherein an absorption peak of a charge transfer interaction between the organic compound and the inorganic compound is not observed in a range from a visible light region to an infrared region.

11. A composite material comprising:
    an organic compound having a molecular weight greater than or equal to 350 and less than or equal to 2000; and
    an inorganic compound exhibiting an electron-accepting property with respect to the organic compound,
    wherein rings of the organic compound are all benzene rings,
    wherein the organic compound includes benzene rings cross-linked with silicon, and
    wherein at least two benzene rings of the benzene rings are linked by a single bond at an ortho position or a meta position.

12. The composite material according to claim 11, wherein the inorganic compound is a transition metal oxide.

13. The composite material according to claim 12, wherein the transition metal oxide is one or more selected from the group consisting of titanium oxide, vanadium oxide, tantalum oxide, molybdenum oxide, tungsten oxide, rhenium oxide, ruthenium oxide, chromium oxide, zirconium oxide, hafnium oxide, and silver oxide.

14. The composite material according to claim 11, wherein the organic compound includes an alkyl group having 1 to 6 carbon atoms as a substituent.

15. The composite material according to claim 11, wherein a measurement value of a highest occupied molecular orbital level of the organic compound by photoelectron spectroscopy is less than or equal to −5.7 eV.

16. A light-emitting element comprising:
    a pair of electrodes; and
    a layer containing the composite material according to claim 11 between the pair of electrodes.

17. The light-emitting element according to claim 16, wherein the layer is in contact with one of the pair of electrodes, wherein the layer is in contact with a second layer containing an organic compound whose rings are all benzene rings, and the number of the benzene rings is greater than or equal to 4 and less than or equal to 25, or wherein the layer is in contact with a light-emitting layer containing a first organic compound whose rings are all benzene rings and a second organic compound dispersed in the first organic compound, and the number of the benzene rings is greater than or equal to 4 and less than or equal to 25.

18. A light-emitting device comprising the light-emitting element according to claim 16 in a display portion or in a light-emitting portion.

19. A light-emitting element comprising:

a layer between a pair of electrodes, wherein the layer comprises a first layer comprising a first light-emitting substance to an n-th layer comprising an n-th light-emitting substance (n is a natural number greater than or equal to 2); and a layer containing the composite material according to claim 2 between the k-th layer comprising the k-th light-emitting substance and the (k+1)-th layer comprising the (k+1)-th light-emitting substance (k is a natural number greater than or equal to 1 and less than n).

20. The composite material according to claim 11, wherein an absorption peak of a charge transfer interaction between the organic compound and the inorganic compound is not observed in a range from a visible light region to an infrared region.

21. An organic compound represented by Formula (1):

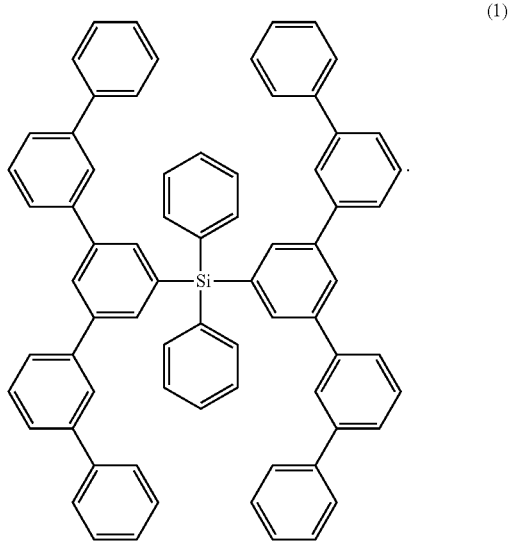 [SMILES: c1ccc(-c2cccc(-c3cc(-c4cccc(-c5ccccc5)c4)cc([Si](c4ccccc4)(c4ccccc4)c4cc(-c5cccc(-c6ccccc6)c5)cc(-c5cccc(-c6ccccc6)c5)c4)c3)c2)cc1]

(1)

22. A composite material comprising:

the organic compound according to claim 21, and an inorganic compound exhibiting an electron-accepting property with respect to the organic compound.

23. A light-emitting element comprising:

a layer containing the composite material according to claim 22.

24. A light-emitting device comprising the light-emitting element according to claim 23 in a display portion or in a light-emitting portion.

* * * * *